US010285617B2

(12) United States Patent
Toth et al.

(10) Patent No.: US 10,285,617 B2
(45) Date of Patent: May 14, 2019

(54) MODULAR PHYSIOLOGIC MONITORING SYSTEMS, KITS, AND METHODS

(71) Applicant: LifeLens Technologies, LLC, Doylestown, PA (US)

(72) Inventors: Landy Toth, Doylestown, PA (US); Robert Schwartz, Inver Grove Heights, MN (US); Chris Pulling, Dayton, MN (US); Roy Martin, Maple Grove, MN (US)

(73) Assignee: LifeLens Technologies, LLC, Ivyland, PA (US)

( * ) Notice: Subject to any disclaimer, the term of this patent is extended or adjusted under 35 U.S.C. 154(b) by 359 days.

(21) Appl. No.: 14/764,830

(22) PCT Filed: Jun. 6, 2014

(86) PCT No.: PCT/US2014/041339
§ 371 (c)(1),
(2) Date: Jul. 30, 2015

(87) PCT Pub. No.: WO2014/197822
PCT Pub. Date: Dec. 11, 2014

(65) Prior Publication Data
US 2015/0351690 A1    Dec. 10, 2015

Related U.S. Application Data

(60) Provisional application No. 61/832,131, filed on Jun. 6, 2013.

(51) Int. Cl.
*A61B 5/00*    (2006.01)
*A61B 5/145*    (2006.01)
(Continued)

(52) U.S. Cl.
CPC .......... *A61B 5/0496* (2013.01); *A61B 5/0024* (2013.01); *A61B 5/0478* (2013.01);
(Continued)

(58) Field of Classification Search
CPC ............ A61B 2562/164; A61B 5/6833; A61B 5/6839
See application file for complete search history.

(56) References Cited

U.S. PATENT DOCUMENTS

| | | |
|---|---|---|
| 2005/0154273 A1 | 7/2005 | Lee et al. |
| 2006/0085056 A1 | 4/2006 | Schouenborg |

(Continued)

FOREIGN PATENT DOCUMENTS

| | | |
|---|---|---|
| JP | H0630907 A | 2/1994 |
| JP | 2003520093 A | 7/2003 |

(Continued)

*Primary Examiner* — Scott Luan
(74) *Attorney, Agent, or Firm* — Ryan, Mason & Lewis, LLP

(57) ABSTRACT

Systems, devices, methods, and kits for monitoring one or more physiologic and/or physical signals from a subject are disclosed. A system including patches and corresponding modules for wirelessly monitoring physiologic and/or physical signals is disclosed. A service system for managing the collection of physiologic data from a customer is disclosed. An isolating patch for providing a barrier between a hand-held monitoring device with a plurality of contact pads and a subject is disclosed.

25 Claims, 10 Drawing Sheets

(51) Int. Cl.
*A61B 5/04* (2006.01)
*A61B 5/0496* (2006.01)
*A61B 5/0408* (2006.01)
*A61B 5/0478* (2006.01)
*A61B 5/0492* (2006.01)
*A61B 5/01* (2006.01)
*A61B 5/022* (2006.01)
*A61B 5/053* (2006.01)
*A61B 5/06* (2006.01)
*A61B 5/11* (2006.01)
*A61B 5/1455* (2006.01)
*A61B 5/22* (2006.01)

(52) U.S. Cl.
CPC ...... *A61B 5/04085* (2013.01); *A61B 5/04087* (2013.01); *A61B 5/0492* (2013.01); *A61B 5/14517* (2013.01); *A61B 5/14542* (2013.01); *A61B 5/6833* (2013.01); *A61B 5/6839* (2013.01); *A61B 5/0015* (2013.01); *A61B 5/01* (2013.01); *A61B 5/022* (2013.01); *A61B 5/04* (2013.01); *A61B 5/0533* (2013.01); *A61B 5/067* (2013.01); *A61B 5/112* (2013.01); *A61B 5/14551* (2013.01); *A61B 5/224* (2013.01); *A61B 5/4812* (2013.01); *A61B 5/4818* (2013.01); *A61B 5/4875* (2013.01); *A61B 2560/0223* (2013.01); *A61B 2560/0242* (2013.01); *A61B 2560/0443* (2013.01); *A61B 2562/0204* (2013.01); *A61B 2562/029* (2013.01); *A61B 2562/0219* (2013.01); *A61B 2562/0223* (2013.01); *A61B 2562/0247* (2013.01); *A61B 2562/0271* (2013.01); *A61B 2562/164* (2013.01); *A61B 2562/166* (2013.01); *A61B 2562/18* (2013.01)

(56) References Cited

U.S. PATENT DOCUMENTS

| | | |
|---|---|---|
| 2006/0122528 A1* | 6/2006 | Gal ...................... A61B 5/1135 600/534 |
| 2007/0027388 A1 | 2/2007 | Chou |
| 2007/0299325 A1* | 12/2007 | Farrell ................. A61B 5/0002 600/301 |
| 2008/0091089 A1 | 4/2008 | Guillory et al. |
| 2010/0317958 A1 | 12/2010 | Beck et al. |
| 2011/0098549 A1* | 4/2011 | Bar Hayim .......... A61B 5/1126 600/391 |
| 2011/0144470 A1 | 6/2011 | Mazar et al. |
| 2011/0190615 A1 | 8/2011 | Phillips et al. |
| 2011/0237922 A1 | 9/2011 | Parker, III et al. |
| 2012/0330126 A1* | 12/2012 | Hoppe ................. A61B 5/0002 600/391 |
| 2013/0041235 A1* | 2/2013 | Rogers ................ A61B 5/6867 600/306 |
| 2013/0102937 A1* | 4/2013 | Ehrenreich ............ A61H 1/00 601/47 |
| 2014/0046423 A1* | 2/2014 | Rajguru ............... A61N 1/0456 607/144 |
| 2014/0206977 A1* | 7/2014 | Bahney ................ A61B 5/6833 600/391 |

FOREIGN PATENT DOCUMENTS

| | | |
|---|---|---|
| JP | 2005193058 A | 7/2005 |
| JP | 2010511465 A | 4/2010 |
| JP | 2012511965 A | 5/2012 |
| WO | 03065926 A2 | 8/2003 |
| WO | 2011080262 A1 | 7/2011 |
| WO | 2012104657 A3 | 8/2012 |
| WO | 2012158748 A1 | 11/2012 |
| WO | PCT/US2014/041339 | 2/2015 |

* cited by examiner

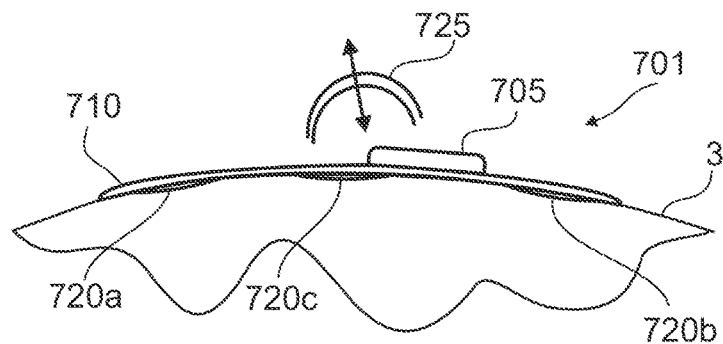
Fig 7
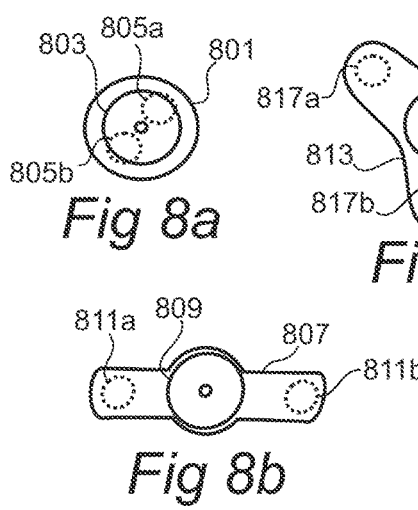
Fig 8a
Fig 8b
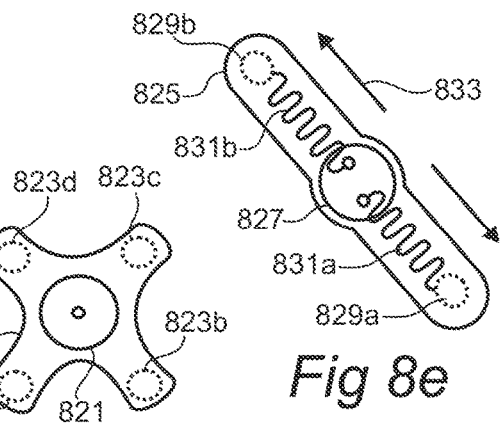
Fig 8c
Fig 8d
Fig 8e
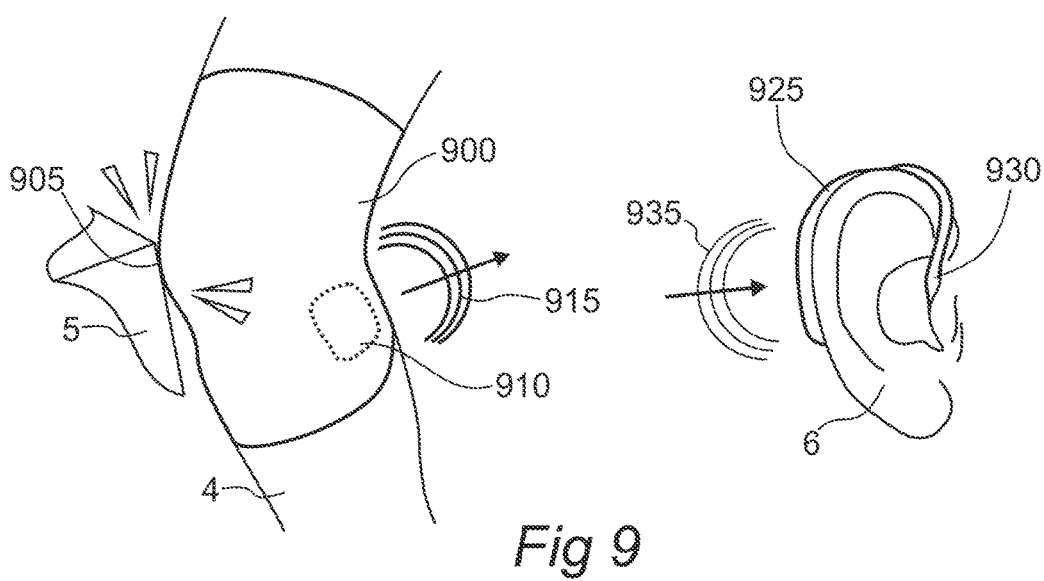
Fig 9

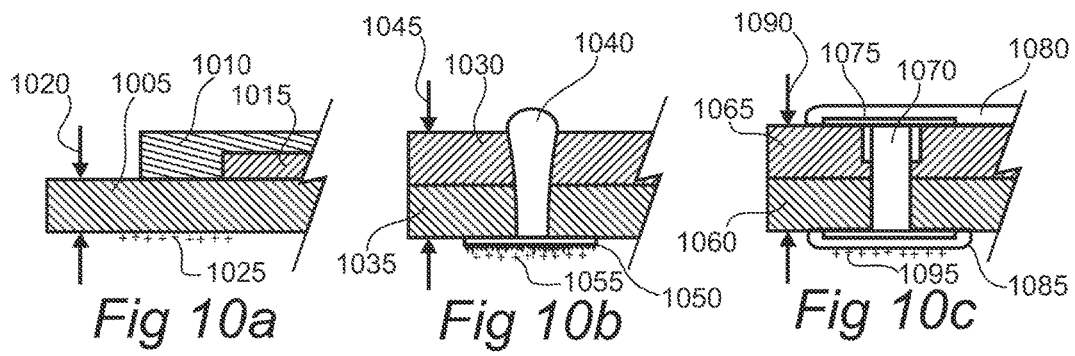
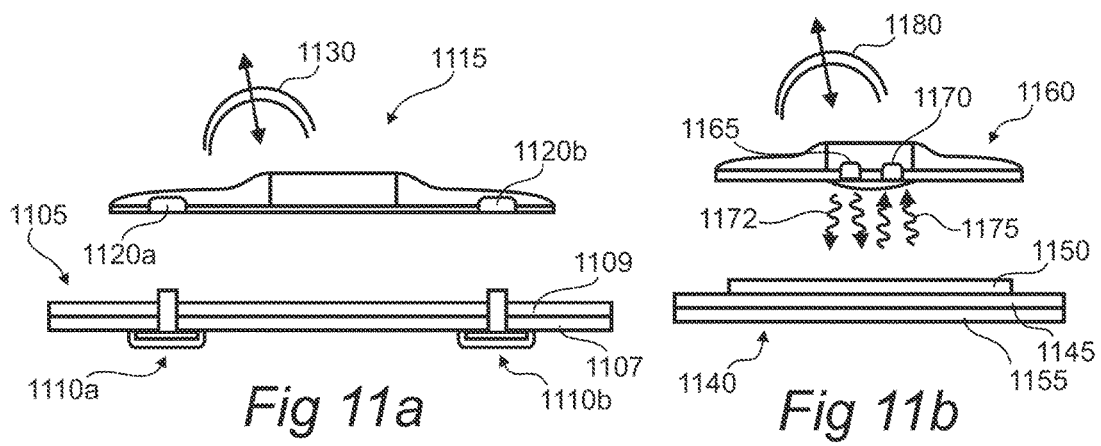
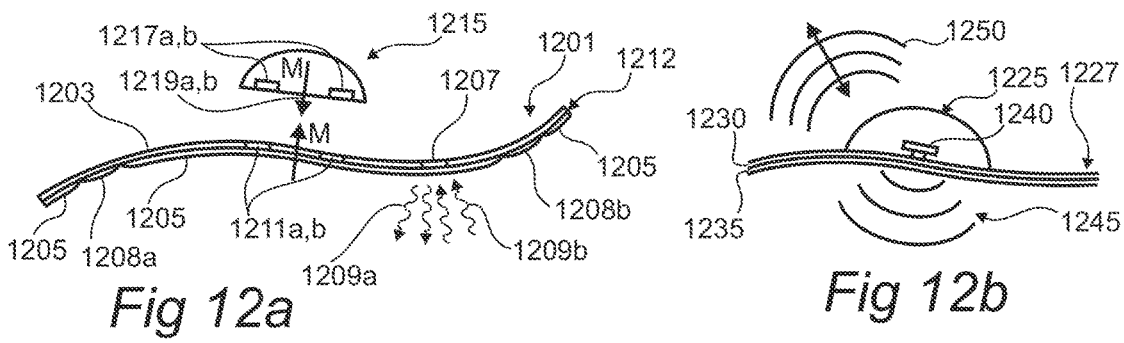
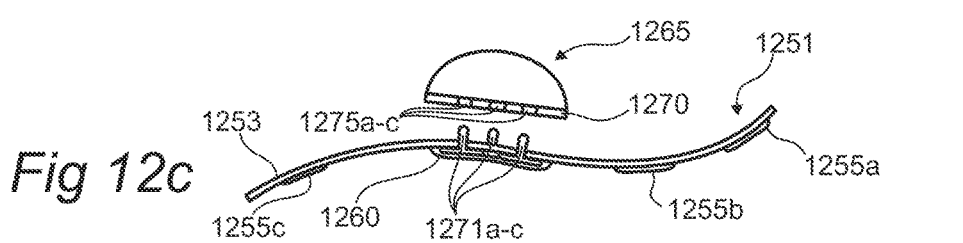

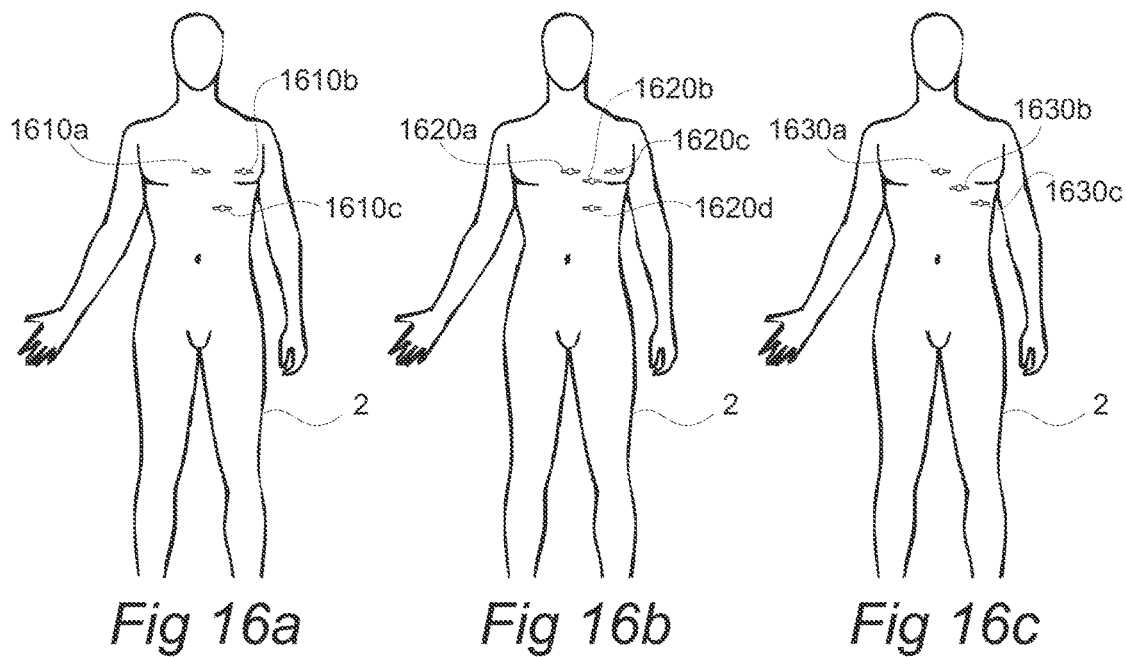
Fig 16a  Fig 16b  Fig 16c
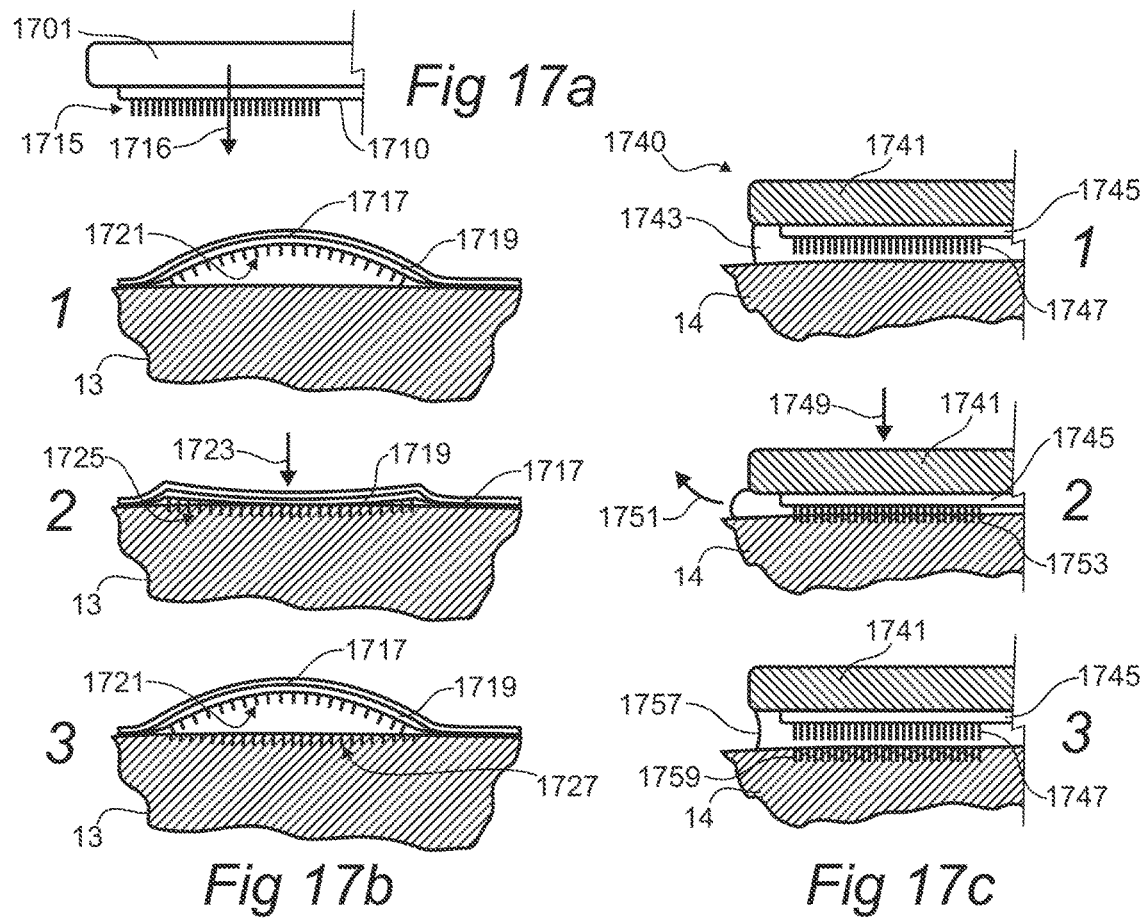
Fig 17a
Fig 17b  Fig 17c

MODULAR PHYSIOLOGIC MONITORING SYSTEMS, KITS, AND METHODS

CROSS REFERENCE TO RELATED APPLICATION

The present application is a national stage application of International Application PCT/US2014/041339 which claims benefit of and priority to U.S. Provisional Application Ser. No. 61/832,131, filed on Jun. 6, 2013, and entitled "Modular Physiological Monitoring Systems, Kits, and Methods," by Landy Toth et al., the entire contents of which is incorporated by reference herein for all purposes.

BACKGROUND

Technical Field

The present disclosure relates to the field of physiologic monitoring. The disclosure relates to systems and methods for reliable measurement of one or more physiologic parameters of a subject. In particular, the disclosure relates to aspects of systems and methods for unobtrusively monitoring electrophysiological activity and/or related information from an ambulatory subject in an uncontrolled setting.

Background

As chronic diseases continue to proliferate throughout the world, there is a heightened need to treat such conditions in a cost effective manner. Remote monitoring of patients with cardiovascular diseases (heart failure, post stroke, etc.), diabetes, kidney failure, COPD, obesity, neurological disorders (depression, Alzheimer's disease, migraines, stress disorders, etc.), arthritis, among other ailments, for purposes of treatment or prevention of such diseases may substantially improve patient outcomes.

Although physiologic monitoring is performed today for a range of purposes, existing technologies are not without shortcomings.

There is a need to measure physiologic parameters of subjects, reliably, simply, and without cables. As the proliferation of mobile and remote medicine increases, simplified and unobtrusive means for monitoring the physiologic parameters of a patient become more important.

Patient compliance is critical to the success of such systems and is often directly correlated to the ease of use and unobtrusiveness of the monitoring solution used.

Existing monitoring systems are often prone to false alarms, usage related failures, unreliable user interfaces, cumbersome interfaces, artifact or electromagnetic interference (EMI) related interference, etc. Such problems decrease productivity of using these systems, can result in lost data, and lead to dissatisfaction on the part of both the subject being monitored and the practitioners monitoring the subject. In the case of a hospital setting, the continual drone of alarms can lead to alarm fatigue and decreased productivity.

Long term compliance of subjects may suffer due to uncomfortable interfaces with monitoring devices, involved maintenance or change-over of disposables, painful or itchy reactions to materials in the devices, and the like.

More reliable, redundant, and user friendly systems are needed that can provide valuable patient data even when operating with limited supervision, expert input, or user manipulation.

SUMMARY

One illustrative, non-limiting objective of this disclosure is to provide systems, devices, methods, and kits for monitoring physiologic and/or physical signals from a subject. Another illustrative, non-limiting objective is to provide simplified systems for monitoring subjects. Another illustrative, non-limiting objective is to provide comfortable long term wearable systems for monitoring subjects. Yet another illustrative, non-limiting objective is to provide systems for facilitating interaction between a user and a subject with regard to physiologic monitoring of the subject.

The above illustrative, non-limiting objectives are wholly or partially met by devices, systems, and methods according to the appended claims in accordance with the present disclosure. Features and aspects are set forth in the appended claims, in the following description, and in the annexed drawings in accordance with the present disclosure.

According to a first aspect there is provided a system for monitoring one or more physiologic and/or physical signals from a subject including one or more patches each in accordance with the present disclosure configured for attachment to the subject, and one or more modules each in accordance with the present disclosure configured and dimensioned to mate with a corresponding patch, and to interface with the subject there through. In aspects, one or more of the modules may be configured to convey and/or store one or more physiologic and/or physical signals, a signal derived therefrom, and/or a metric derived therefrom obtained via the interface with the subject.

In aspects, the system may include or interface with a host device in accordance with the present disclosure coupled in wireless communication with one or more of the modules configured to receive one or more of the signals and/or metrics therefrom. In aspects, the host device may include features for recharging and/or performing diagnostic tests on one or more of the modules.

According to aspects there is provided, use of a system in accordance with the present disclosure to monitor a subject, to monitor an electrocardiogram of a subject, to perform one or more tasks in accordance with the present disclosure, etc.

According to aspects there is provided an interface (i.e. a patch in accordance with the present disclosure) for monitoring a physiologic and/or physical signal from a subject, including a substrate, an adhesive coupled to the substrate formulated for attachment to the skin of a subject, and one or more sensors and/or electrodes each in accordance with the present disclosure coupled to the substrate, arranged, configured, and dimensioned to interface with the subject.

In aspects, the substrate may be formed from an elastic or polymeric material and the patch is configured to maintain operation when stretched to more than 25%, more than 50%, or more than 80%.

In aspects, the interface (i.e. the patch) may be configured with a moisture vapor transmission rate of between 200 grams/square meter $(g/m^2)/24$ hours (hrs) and 20,000 $g/m^2/24$ hrs, between 500 $g/m^2/24$ hrs and 12,000 $g/m^2/24$ hrs, or between 2,000 $g/m^2/24$ hrs and 8,000 $g/m^2/24$ hrs, etc.

In aspects, the interface may be used for a range of applications, some non-limiting examples of which include electrocardiography, sleep assessment, bruxism assessment, sleep apnea, traumatic brain injury, black box event based monitoring (e.g. for syncope, atrial fibrillation, etc.), biofeedback, stress management, relaxation, physiotherapy, stroke or surgical recovery, or the like. Additional uses and details thereof are described throughout the present disclosure.

According to aspects there is provided a device (i.e. a module in accordance with the present disclosure) for monitoring a physiologic, physical, and/or electrophysiological signal from a subject including, a housing, a printed circuit board (PCB) including one or more microcircuits, and an interconnect configured for placement of the device onto a subject interface (i.e. a patch in accordance with the present disclosure).

In aspects, the printed circuit board may constitute at least a portion of the housing.

In aspects, the device may include a three dimensional antenna coupled to the microcircuits (i.e. coupled with a transceiver, transmitter, radio, etc. included within the microcircuits). In aspects, the antenna may be printed onto or embedded into the housing.

According to aspects there is provided a kit for monitoring a physiologic, physical, and/or electrophysiological signal from a subject, including one or more patches in accordance with the present disclosure, one or more modules in accordance with the present disclosure; a recharging bay in accordance with the present disclosure, and one or more accessories in accordance with the present disclosure.

In aspects, one or more of the accessories may include an adhesive removing agent configured to facilitate substantially pain free removal of one or more of the patches from a subject.

According to aspects there is provided, a service system for managing the collection of physiologic data from a customer, including a customer data management service, configure to generate and/or store the customer profile referencing customer preferences, data sets, and/or monitoring sessions, an automated product delivery service configured to provide the customer with one or more monitoring products or supplies in accordance with the present disclosure, and a datacenter configured to store, analyze, and/or manage the data obtained from the customer during one or more monitoring sessions.

In aspects, the service system may include a report generating service configured to generate one or more monitoring reports based upon the data obtained during one or more monitoring sessions, a report generating service coupled to the datacenter configured to generate one or more monitoring reports based upon the data obtained during one or more monitoring sessions, and/or a recurrent billing system configured to bill the customer based upon the number or patches consumed, the data stored, and/or the reports generated throughout the course of one or more monitoring session.

According to aspects there is provided a method for monitoring a physiologic, physical, and/or electrophysiological signal from a subject, including one or more steps in accordance with the present disclosure.

In aspects, one or more of the steps may be performed at least in part by a system in accordance with the present disclosure.

According to aspects there is provided, an isolating patch for providing a barrier between a handheld monitoring device with a plurality of contact pads and a subject, including a flexible substrate with two surfaces, a patient facing surface and an opposing surface, and an electrically and/or ionically conducting adhesive coupled to at least a portion of the patient facing surface configured so as to electrically and mechanically couple with the subject when placed thereupon, wherein the conducting adhesive is exposed within one or more regions of the opposing surface of the substrate, the regions patterned so as to substantially match the dimensions and layout of the contact pads.

In aspects, the conducting adhesive may include an anisotropically conducting adhesive, with the direction of conduction oriented substantially normal to the surfaces of the substrate.

According to aspects there is provided, a patch interface (i.e. a patch in accordance with the present disclosure) for monitoring one or more physiologic and/or electrophysiological signals from a subject, including a substrate, an adhesive coupled to the substrate formulated for attachment to the skin of a subject, an interconnect embedded into the substrate for attachment of the patch to a microcircuit, and one or more sensors and/or electrodes attached to or embedded onto the surface of the substrate, the sensors and/or electrodes arranged, configured, and dimensioned to interface with the subject when the adhesive is attached thereto.

In aspects, the adhesive may be patterned onto the substrate so as to form one or more exposed regions of the substrate, one or more of the sensors and/or electrodes arranged within the exposed regions. One or more of the electrodes may include an inherently or ionically conducting gel adhesive.

In aspects, one or more of the electrode may include an electrode feature arranged so as to improve the electrical connection between the electrode and the skin upon placement on a subject. In aspects, the improved electrical connection may be achieved after pressure is applied to the electrode (i.e. after the patch is secured to the subject and then a pressure is applied to the electrode). The electrode feature may include one or more microfibers, barbs, microneedles, or spikes to penetrate into a stratum corneum of the skin. The electrode feature may be configured to penetrate less than 2 mm into the skin, less than 1 mm, less than 0.5 mm, less than 0.2 mm, or the like during engagement therewith. In aspects, a gel adhesive in accordance with the present disclosure located adjacent to the electrode features (i.e. between the features and the skin) may be configured to maintain the improved electrical connection to the skin for more than 1 hr, more than 1 day, or more than 3 days after the electrode contacts the skin or pressure is applied to the electrode.

In aspects, a patch interface in accordance with the present disclosure may include one or more stretchable electrically conducting traces attached to the substrate, arranged so as to coupled one or more of the sensors and/or electrodes with one or more of the interconnects.

In aspects, the interconnect may include a plurality of connectors, the connectors physically connected to each other through the substrate. The patch may include an isolating region arranged so as to isolate one or more of the connectors from the skin while the patch is engaged therewith.

In aspects, the patch interface may be sufficiently physically frail such that it cannot retain a predetermined shape in a free standing state. The patch interface may include a temporary stiffening member attached to the substrate, the temporary stiffening member configured to provide retention of the shape of the patch interface prior to attachment to the subject, the stiffening member being removable from the substrate after attachment to the subject. In aspects, after removal of the stiffening member, the retention of the shape of the patch interface may be provided by the skin of the subject. Removal of the patch interface from the skin of the subject may result in a permanent loss in shape of the patch interface without tearing of the patch interface. In aspects, the interconnect may be sufficiently frail such that removal of the patch interface from the skin of the subject may result in a permanent loss of shape of the interconnect.

In aspects, an adhesive in accordance with the present disclosure may have a peel tack to mammalian skin of greater than 0.02 Newton/millimeter (N/mm), greater than 0.1 N/mm, greater than 0.25 N/mm, greater than 0.50 N/mm, greater than 0.75 N/mm, or the like. The patch interface may have a tear strength of greater than 0.5 N/mm, greater than 1 N/mm, greater than 2 N/mm, greater than 8 N/mm, or the like.

In aspects, a patch interface in accordance with the present disclosure may have a ratio between the tear strength of the patch and the peel tack of the adhesive to mammalian skin is greater than 8:1, greater than 4:1, greater than 2:1, or the like. In aspects, the substrate may be formed from a soft pseudo-elastic material and the patch interface may be configured to maintain operation when stretched to more than 25%, more than 50%, more than 80%, or the like. In aspects, the patch interface may be configured with a moisture vapor transmission rate of between 200 $g/m^2/24$ hrs and 20,000 $g/m^2/24$ hrs, between 500 $g/m^2/24$ hrs and 12,000 $g/m^2/24$ hrs, between 1,000 $g/m^2/24$ hrs and 8,000 $g/m^2/24$ hrs, or the like.

According to aspects, there is provided a module for monitoring one or more physiologic and/or electrophysiological signals from a subject, including a housing, a circuit board including one or more microcircuits, and a module interconnect coupled to one or more of the microcircuits configured for placement and coupling of the device onto a patch interface in accordance with the present disclosure.

In aspects, the module interconnect may be embedded into the circuit board, and/or the circuit board may constitute at least a portion of the housing. The module may include a three dimensional antenna in accordance with the present disclosure, the antenna coupled to one or more of the microcircuits, the microcircuits including a transceiver or transmitter coupled to the antenna. In aspects, the antenna may be printed on an interior wall of or embedded into the housing, the circuit board providing a ground plane for the antenna. In aspects, the housing may be shaped like a dome and the antenna may be patterned into a spiraling helix centered within the dome.

In aspects, a module in accordance with the present disclosure may include a sensor coupled with one or more of the microcircuits, the sensor configured to interface with the subject upon attachment of the module to the patch interface. The module may include a sensor and/or microelectronics configured to interface with a sensor included on a corresponding patch interface. In aspects, one or more of the sensors may include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, a combination thereof, or the like.

In aspects, the module may be hermetically sealed. The module and/or patch interface may include a gasket coupled to the circuit board or the substrate, the gasket formed so as to isolate the region formed by the module interconnect and the patch from a surrounding environment, when the module is coupled with the patch.

According to aspects there is provided, a device for monitoring one or more physiologic and/or electrophysiologic signals from a subject including a patch interface in accordance with the present disclosure; and a module in accordance with the present disclosure. In aspects, the module interconnect included within the module may be sized and dimensioned to interface with a corresponding interconnect included within the patch interface, wherein to form an operable interconnection between the patch interface and the module, the patch interface may first be coupled to the subject (i.e. so as to maintain the shape thereof during the process of coupling the patch interface to a corresponding module).

In aspects, the module interconnect may include an electrically conducting magnetic element, and the patch interface may include one or more ferromagnetic regions coupled to the substrate, the magnetic elements arranged so as to physically and/or electrically couple the module to the patch interface when the magnetic elements are aligned with the ferromagnetic regions. In aspects, the ferromagnetic regions may be formed from stretchable pseudo elastic material and/or may be printed onto the substrate. In aspects, the module and/or the patch interface may include one or more fiducial markings to visually assist with the alignment of the module to the patch during coupling thereof.

According to aspects there is provided, a system for monitoring one or more physiologic and/or electrophysiological signals from a subject including a patch interface in accordance with the present disclosure configured for attachment to the subject, and a module in accordance with the present disclosure configured and dimensioned to mate with the patch, and to interface with the subject there through, the module configured to convey and/or store one or more physiologic, electrophysiological, and/or physical signals, a signal derived therefrom, and/or a metric derived therefrom obtained via the interface with the subject.

In aspects, the system may include a host device coupled in wireless communication or physical communication with the module, configured to receive one or more of the signals and/or metrics therefrom. In aspects, the host device may include one or more features for recharging and/or performing diagnostic tests on one or more of the modules. In aspects, the system may include a plurality of modules, the modules being hot swappable with the patch interface, so as to maintain a nearly continuous or continuous operation thereof.

In aspects, the system may include a plurality of modules and associated patch interfaces for placement onto a signal subject, the host device, and/or one or more of the modules configured to coordinate synchronous monitoring of the signals amongst the modules on the subject. In aspects, a host device in accordance with the present disclosure may be integrated into a bedside alarm clock, housed in an accessory, within a purse, a backpack, a wallet, is or is included in a mobile computing device, a smartphone, a tablet computer, a pager, a laptop, a local router, a data recorder, a network hub, a server, a secondary mobile computing device, a repeater, a combination thereof, or the like.

According to aspects there is provided, use of a device, a module, a patch, and/or a system each in accordance with the present disclosure to monitor an electrocardiogram of a subject.

According to aspects there is provided, a method for monitoring one or more physiologic and/or electrophysiological signals from a subject, including attaching one or more soft breathable and hypoallergenic devices to one or more sites on the subject, obtaining one or more local physiologic and/or electrophysiological signals each of the devices, and analyzing the signals obtained from each of the devices to generate a metric, diagnostic, report, and/or additional signals therefrom.

In aspects, the method may include hot swapping one or more of the devices without interrupting the step of obtaining, and/or calibrating one or more of the devices while on the subject. In aspects, the step of calibrating may be performed with an additional medical device (e.g. a blood pressure cuff, a thermometer, a pulse oximeter, a cardiopulmonary assessment system, a clinical grade electrocardiogram (EKG) diagnostic system, etc.).

In aspects, the method may include determining the position and/or orientation of one or more of the devices on the subject, and/or determining the position and/or orientation from a photograph, a video, or a surveillance video.

In aspects, one or more steps of a method in accordance with the present disclosure may be performed at least in part by a device, patch interface, module, and/or system each in accordance with the present disclosure.

According to aspects there is provided, an isolating patch for providing a barrier between a handheld monitoring device with a plurality of contact pads and a subject, including a flexible substrate with two surfaces, a patient facing surface and an opposing surface, and an electrically and/or ionically conducting adhesive coupled to at least a portion of the patient facing surface configured so as to electrically and mechanically couple with the subject when placed thereupon, wherein the conducting adhesive is exposed within one or more regions of the opposing surface of the substrate, the regions patterned so as to substantially match the dimensions and layout of the contact pads.

In aspects, the conducting adhesive may include an anisotropically conducting adhesive, with the direction of conduction oriented substantially normal to the surfaces of the substrate.

According to aspects there is provided, a system for measuring blood pressure of a subject in an ambulatory setting including an EKG device in accordance with the present disclosure (i.e. a patch/module pair in accordance with the present disclosure configured to measure local electrophysiological signals in adjacent tissues), configured for placement onto a torso of the subject, the EKG device configured to measure an electrocardiographic signal from the torso of the subject so as to produce an EKG signal, one or more pulse devices (i.e. patch/module pairs in accordance with the present disclosure configured to measure local blood flow in adjacent tissues) each in accordance with the present disclosure, configured for placement onto one or more sites on one or more extremities of the subject, each of the pulse devices configured to measure a local pulse at the placement site so as to produce one or more pulse signals; and a processor included in or coupled to one or more of the EKG device and the pulse devices, the processor configured to receive the EKG signal, the pulse signals, and/or signals generated therefrom, the processor including an algorithm, the algorithm configured to analyze one or more temporal metrics from the signals in combination with one or more calibration parameters, to determine the blood pressure of the subject.

In aspects, the system for monitoring blood pressure of a subject may include a blood pressure cuff configured to produce a calibration signal, the processor configured to generate one or more of the calibration parameters, from the calibration signal in combination with the EKG signal, and pulse signals.

In aspects, one or more of the devices may include an orientation sensor, the orientation sensor configured to obtain an orientation signal, the processor configured to receive the orientation signal or a signal generated therefrom, and to incorporate the orientation signal into the analysis. Some non-limiting examples of orientation sensors include one or more of an altimeter, a barometer, a tilt sensor, a gyroscope, combinations thereof, or the like.

A system for measuring the effect of an impact on physiologic state of a subject including an electroencephalogram (EEG) device (i.e. a patch/module pair in accordance with the present disclosure configured to measure local electrophysiological signals associated with brain activity in adjacent tissues) in accordance with the present disclosure, configured for placement behind an ear, on the forehead, near a temple, onto the neck of the subject, or the like, the EEG device configured to measure an electroencephalographic signal from the head of the subject so as to produce an EEG signal, and configured to measure one or more kinetic and/or kinematic signals from the head of the subject so as to produce an impact signal, and a processor included in or coupled to the EEG device, the processor configured to receive the EEG signal, the impact signals, and/or signals generated therefrom, the processor including an algorithm, the algorithm configured to analyze the impact signals to determine if the subject has suffered an impact, to separate the signals into pre impact and post impact portions and to compare the pre and post impact portions of the EEG signal, to determine the effect of the impact on the subject.

In aspects, the EEG device may include additional sensors such as a temperature sensor configured to generate a temperature signal from the subject or a signal generated therefrom, the processor configured to receive the temperature signal and to assess a thermal state of the subject therefrom. In aspects, the EEG device may include a hydration sensor configured to generate a fluid level signal from the subject, the processor configured to receive the fluid level signal or a signal generated therefrom, and to assess the hydration state of the subject therefrom.

In aspects, the EEG device and/or the processor may include or be coupled to a memory element, the memory element including sufficiently large space to store the signals for a period of 3 minutes, 10 minutes, 30 minutes, or 1 hr.

In aspects, the system for measuring the effect of an impact on physiologic state of a subject may include an EKG device (i.e. a patch/module pair in accordance with the present disclosure configured to measure local electrophysiological signals in adjacent tissues) in accordance with the present disclosure, the EKG device configured for placement onto the torso or neck of the subject, the EKG device configured to measure an electrophysiological signal pertaining to cardiac function of the subject so as to produce an EKG signal, the processor configured to receive the EKG signal or a signal generated therefrom, the algorithm configured so as to incorporate the EKG signal into the assessment. In aspects, the processor may be configured to extract a heart rate variability (HRV) signal from the EKG signal, a pre impact and post impact portion of the HRV signal compared to determine at least a portion of the effect of the impact.

According to aspects there is provided, a system for assessing a sleep state of a subject including an electromyography (EMG)/electrooculography (EOG) device (i.e. a patch/module pair in accordance with the present disclosure configured to measure local electromyographic and/or electrooculographic signals from adjacent tissues), in accordance with the present disclosure, configured for placement behind an ear, on a forehead, substantially around an eye, near a temple, or onto a neck of the subject, the EMG/EOG device configured to measure one or more electromyographic and/or electrooculographic signals from the head or neck of the subject so as to produce an EMG/EOG signal, and a processor included in or coupled to the EMG/EOG device, the processor configured to receive the EMG/EOG signal, and/or signals generated therefrom, the processor including an algorithm, the algorithm configured to analyze EMG/EOG signal, to determine the sleep state of the subject.

In aspects, the EMG/EOG device may include a microphone, the microphone configured to obtain an acoustic signal from the subject, the processor configured to receive the acoustic signal or a signal generated therefrom, the algorithm configured so as to incorporate the acoustic signal into the assessment.

In aspects, the system may include a sensor for evaluating oxygen saturation (sPO2) at one or more sites on the subject to obtain an oxygen saturation signal from the subject, the processor configured to receive the oxygen saturation signal or a signal generated therefrom, the algorithm configured so as to incorporate the oxygen saturation signal into the assessment.

In aspects, the processor may include a signal analysis function, the signal analysis function configured to analyze the EMG/EOG signals, the acoustic signal, and/or the oxygen saturation signal to determine the sleep state of the subject, identify snoring, identify a sleep apnea event, identify a bruxism event, identify a rapid eye movement (REM) sleep state, identify a sleep walking state, a sleep talking state, a nightmare, or identify a waking event. In aspects, the system may include a feedback mechanism, configured to interact with the subject, a user, a doctor, a nurse, a partner, a combination thereof, or the like. The processor may be configured to provide a feedback signal to the feedback mechanism based upon the analysis of the sleep state of the subject. The feedback mechanism may include a transducer, a loudspeaker, tactile actuator, a visual feedback means, a light source, a buzzer, a combination thereof, or the like to interact with the subject, the user, the doctor, the nurse, the partner, or the like.

According to aspects there is provided, a system for assessing a gait and/or a muscle movement of a subject including an EMG device (i.e. a patch/module pair in accordance with the present disclosure configured to measure local electromyographic signals from adjacent tissues) in accordance with the present disclosure, configured for placement over a muscle group on the subject, the EMG device configured to measure one or more electromyographic signals from the muscle group of the subject so as to produce an EMG signal, and a processor included in or coupled to the EMG device, the processor configured to receive the EMG signal, and/or signals generated therefrom, the processor including an algorithm, the algorithm configured to analyze EMG signal to determine at least a portion of the gait and/or the muscle movement of the subject.

In aspects, the system may include a plurality of EMG devices, each EMG device configured to monitor a separate muscle group on the subject, the processor configured to synchronize and analyze the EMG signals received from each EMG device to determine at least a portion of the gait and/or the muscle movement of the subject.

In aspects, one or more of the EMG devices may include an orientation, kinetic, kinematic, and/or proprioception sensor each in accordance with the present disclosure, configured so as to generate a kinematic signal, the processor configured to incorporate the kinematic signal into the analysis. In aspects, the processor may be configured to analyze one or more of the EMG signals to generate a muscle exertion metric.

BRIEF DESCRIPTION OF THE DRAWINGS

Several aspects of the disclosure can be better understood with reference to the following drawings. In the drawings, like reference numerals designate corresponding parts throughout the several views.

FIG. 7 shows a schematic of a patch/module pair attached to a subject in accordance with the present disclosure.

FIGS. 8a-e show aspects of patch layouts in accordance with the present disclosure.

FIG. 9 shows aspects of an impact sensing patch and a feedback component in accordance with the present disclosure.

FIGS. 10a-c show aspects of a patch in accordance with the present disclosure.

FIGS. 11a-b show aspects of patches and modules in accordance with the present disclosure.

FIGS. 12a-c show aspects of patches and modules in accordance with the present disclosure.

FIGS. 16a-c show arrangements of patches on a subject for generating an EKG in accordance with the present disclosure.

FIGS. 17a-c show aspects of electrode features and methods for engaging such features with skin in accordance with the present disclosure.

DETAILED DESCRIPTION

Figure 1A:
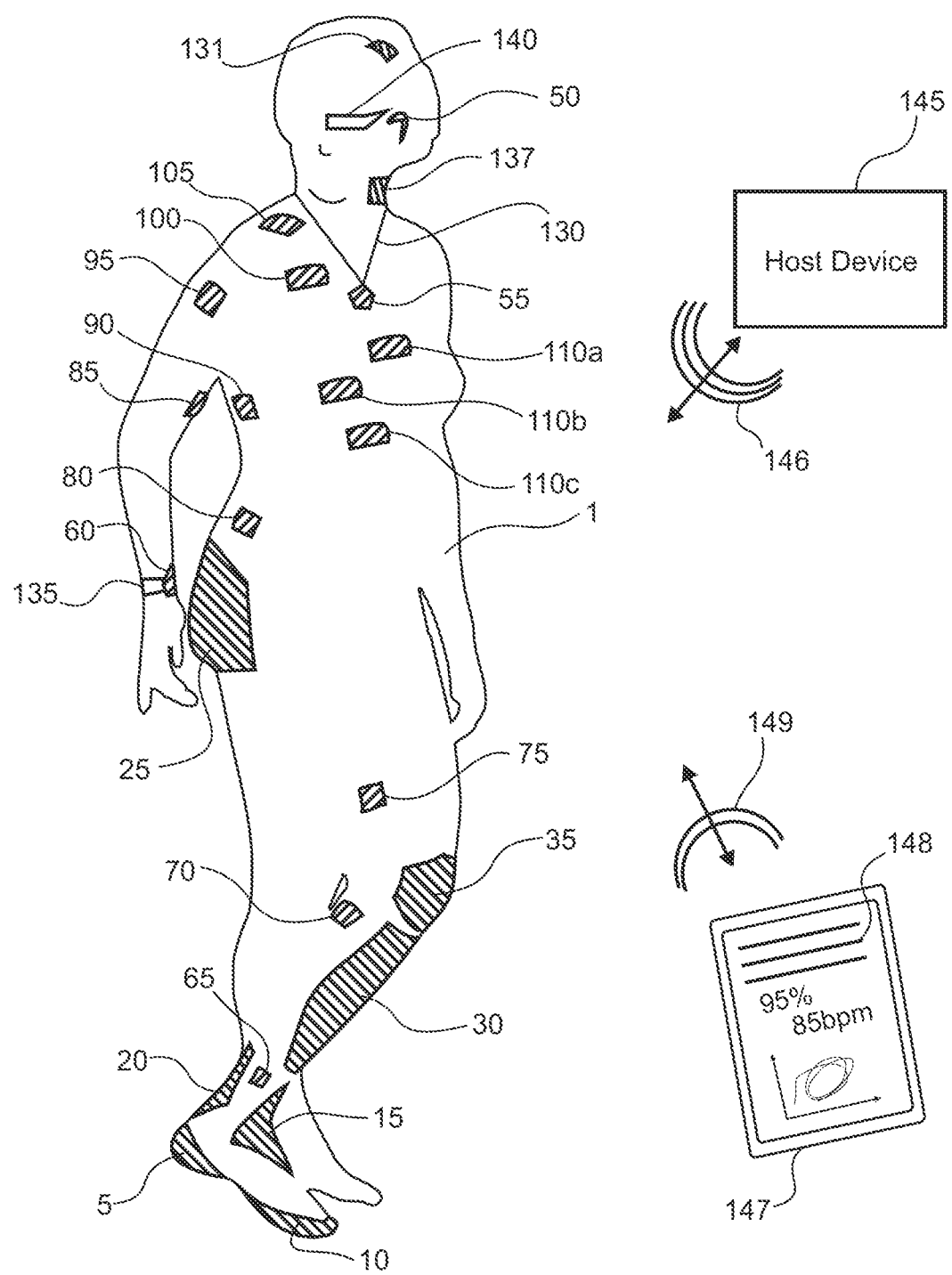
FIGS. 1a-d show aspects of modular physiologic monitoring systems in accordance with the present disclosure.

Particular embodiments of the present disclosure are described herein below with reference to the accompanying drawings; however, the disclosed embodiments are merely examples of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

A modular physiologic monitoring system in accordance with the present disclosure for assessing one or more physiologic parameters of a subject (e.g. a human subject, a patient, an athlete, a trainer, an animal, such as equine, canine, porcine, bovine, etc.) with a body may include one or more patches, each patch adapted for attachment to the body of the subject (e.g. attachable to the skin thereof, reversibly attachable, adhesively attachable, with a disposable interface and a reusable module, etc.). In aspects, the physiologic monitoring system may include one or more modules, each module may include a power source (e.g. a battery, a rechargeable battery, an energy harvesting transducer, microcircuit, and an energy reservoir, a thermal gradient harvesting transducer, a kinetic energy harvesting transducer, a radio frequency energy harvesting transducer, a fuel cell, a biofuel cell, etc.), signal conditioning circuitry, communication circuitry, one or more sensors, or the like, configured to generate one or more signals (i.e. physiologic and/or physical signals).

One or more of the patches may include one or more interconnects, configured and dimensioned so as to couple with one or more of the modules, said modules including a complimentary interconnect configured and dimensioned to couple with the corresponding patch. The patch may include a bioadhesive interface for attachment to the subject, the module retainable against the subject via interconnection with the patch.

In aspects, the patch may be configured so as to be single use (i.e. disposable). The patch may include a thin, breathable, stretchable laminate. In aspects, the laminate may include a substrate, a bioadhesive, one or more sensing elements in accordance with the present disclosure, and one or more interconnects for coupling one or more of the sensing elements with a corresponding module.

In aspects, to retain a high degree of comfort and long term wear-ability of the patch on a subject, to limit interference with normal body function, to limit interference with joint movement, or the like, the patch may be sufficiently thin and frail, such that it may not substantially retain a predetermined shape while free standing. Such a definition is described in further detail below. The patch may be provided with a temporary stiffening film to retain the shape thereof prior to placement of the patch onto the body of a subject. Once adhered to the subject, the temporary stiffening film may be removed from the patch. While the patch is adhered to the subject, the shape and functionality of the patch may be substantially retained. Upon removal of the patch from the subject, the, now freestanding patch is sufficiently frail such that the patch can no-longer substantially retain the predetermined shape (i.e. sufficiently frail such that the patch will not survive in a free standing state). In aspects, stretch applied to the patch while removing the patch from the subject may result in snap back once the patch is in a freestanding state that renders such a patch to crumple into a ball and no longer function.

In aspects, the patch may include a film (e.g. a substrate), with sufficiently high tear strength, such that, as the patch is peeled from the skin of a subject, the patch does not tear. In aspects, the ratio between the tear strength of the patch and the peel adhesion strength of the patch to skin (i.e. tear strength: peel adhesion strength), is greater than 8:1, greater than 4:1, greater than 2:1, or the like. Such a configuration may be advantageous so as to ensure the patch may be easily and reliably removed from the subject after use without tearing.

In aspects, the patch may include a bioadhesive with peel tack to mammalian skin of greater than 0.02 N/mm, greater than 0.1 N/mm, greater than 0.25 N/mm, greater than 0.50 N/mm, greater than 0.75 N/mm, or the like. Such peel tack may be approximately determined using an American Society for Testing and Materials (ASTM) standard test, ASTM D3330: Standard test method for peel adhesion of pressure-sensitive tape.

In aspects, the patch may exhibit a tear strength of greater than 0.5 N/mm, greater than 1 N/mm, greater than 2 N/mm, greater than 8 N/mm, or the like. Such tear strength may be approximately determined using an ASTM standard test, ASTM D624: Standard test method for tear strength of conventional vulcanized rubber and thermoplastic elastomers.

In aspects, the patch may be provided with a characteristic thickness, of less than 50 micrometer (um), less than 25 um, less than 12 um, less than 8 um, less than 4 um, or the like. Yet, in aspects, a balance between the thickness, stiffness, and tear strength may be obtained so as to maintain sufficiently high comfort levels for a subject, minimizing skin stresses during use (i e minimizing skin stretch related discomfort and extraneous signals as the body moves locally around the patch during use), minimizing impact on skin health, minimizing risk of nicking during use, and minimizing risk of maceration to the skin of a subject, while limiting risk of tearing of the patch during removal from a subject, etc.

In aspects, the properties of the patch may be further altered so as to balance the hydration levels of one or more hydrophilic or amphiphilic components of the patch while attached to a subject. Such adjustment may be advantageous to prevent over hydration or drying of an ionically conducting component of the patch, to manage heat transfer coefficients within one or more elements of the patch, to manage salt retention into a reservoir in accordance with the present disclosure, and/or migration during exercise, to prevent pooling of exudates, sweat, or the like into a fluid measuring sensor incorporated into the patch or associated module, etc. In aspects, the patch or a rate determining component thereof may be configured with a moisture vapor transmission rate of between 200 $g/m^2/24$ hrs and 20,000 $g/m^2/24$ hrs, between 500 $g/m^2/24$ hrs and 12,000 $g/m^2/24$ hrs, between 2,000 $g/m^2/24$ hrs and 8,000 $g/m^2/24$ hrs, or the like.

Such a configuration may be advantageous for providing a comfortable wearable physiologic monitor for a subject, while reducing on material waste, cost of goods, preventing contamination or disease spread through uncontrolled re-use, and the like.

In aspects, one or more patches and/or modules may be configured for electrically conducting interconnection, inductively coupled interconnection, capacitively coupled interconnection, with each other. In the case of an electrically conducting interconnect, each patch and module interconnect may include complimentary electrically conducting connectors, configured and dimensioned so as to mate together upon attachment. In the case of an inductively or capacitively coupled interconnect, the patch and module may include complimentary coils or electrodes respectively, configured and dimensioned so as to mate together upon attachment.

Each patch or patch/module pair may be configured to monitor one or more local physiologic and/or physical parameters of the attached subject (e.g. local to the site of attachment, etc.), local environment, combinations thereof, or the like, and to relay such information in the form of signals to a host device (e.g. via a wireless connection, via a body area network connection, or the like), one or more patches or modules on the subject, or the like.

In aspects, the host device may be configured to coordinate information exchange to/from each module and/or patch, and to generate one or more physiologic signals, physical signals, environmental signals, kinetic signals, diagnostic signals, alerts, reports, recommendation signals, commands, combinations thereof, or the like for the subject, a user, a network, an electronic health record (EHR), a database (e.g. as part of a data management center, an EHR, a social network, etc.), a processor, combinations thereof, or the like.

In aspects, a system in accordance with the present disclosure may include a plurality of substantially similar modules (i.e. generally interchangeable modules, but with unique identifiers), for coupling with a plurality of patches, each patch, optionally different from the other patches in the system (e.g. potentially including alternative sensors, sensor types, sensor configurations, electrodes, electrode configurations, etc.). Each patch may include an interconnect suitable for attachment to an associated module. Upon attachment of a module to a corresponding patch, the module may validate the type and operation of the patch to which it has been mated. In aspects, the module may then initiate monitoring operations on the subject via the attached patch, communicate with one or more patches on the subject, a hub, etc. The data collection from each module may be coordinated through one or more modules and/or with a host device in accordance with the present disclosure. The modules may report a time stamp along with the data in order to synchronize data collection across multiple patch/module pairs on the subject, between subjects, etc. Thus, if a module is to be replaced, a hot swappable replacement (i.e. replacement during a monitoring procedure) can be carried out easily by the subject, a caregiver, practitioner, etc. during the monitoring process. Such a configuration may be advantageous for performing redundant, continuous monitoring of a subject, and/or to obtain spatially relevant information from a plurality of locations on the subject during use.

In aspects, the modules and/or patches may include corresponding interconnects for coupling with each other during use. The interconnects may include one or more connectors, configured such that the modules and patches may only couple in a single unique orientation with respect to each other. In aspects, the modules may be color coded by function. A temporary stiffening element attached to a patch may include instructions, corresponding color coding, etc. so as to assist a user or subject with simplifying the process of monitoring.

The following overviews aspects described herein which may be generally applied to the appended Figures where applicable.

Modular Monitoring Aspects

In aspects, a system in accordance with the present disclosure may include a plurality of patches or patch/module pairs to generate higher level function and/or increased clinically relevant data than may be obtained from a single site on the body. Some non-limiting examples of such applications include multi-electrode electrocardiograms, traumatic brain injury assessment, touch restoration, gait analysis, cardiorespiratory assessment, metabolic assessment, breath/gait synchronization, blood pressure monitoring, combined reading analysis (i.e. combining a first function such as EEG, with another such as HRV to elucidate deeper understanding of the state of a subject or the extend of a condition or disease state).

In one non-limiting example, a high level of cardiovascular information may be evaluated from a multi-site EKG diagnostic system (i.e. a 12 lead EKG collected from several individual patches or patch/module pairs). In an application relating to the capture of diagnostic grade EKG data, a plurality of patch/modules each in accordance with the present disclosure may be attached to a subject. A calibration step may be performed to determine the general location of the patch/modules on the body or the relationship between patch/modules on the body during the usage case. In one non-limiting example, an image of the arrangement may be acquired (e.g. by a smartphone camera, a host device, etc.) and analyzed so as to establish the physical layout of patch/modules on the subject. Such an analysis may be performed by comparing the location of each patch/module to each other, and/or to one or more body features (e.g. head, chest, shoulders, waist, etc.), collected from the acquired image.

In aspects wherein one or more patch/module pairs are equipped with a pulse generator and one or more electrodes suitable for emitting one or more pulses into the subject, a calibration step may include emitting one or more pulses from one or more patch/module pairs and monitoring for evoked potentials at one or more of the additional patch/module pairs. A combination of the timing delay, polarity, and/or amplitude of the received pulses as recorded collectively by the additional patch/module pairs may be used to generate a location metric. The location metric may be used to estimate the location of one or more patch/module pairs on the body of the subject.

In aspects wherein one or more patch/module pairs are equipped with a plurality of electrophysiological sensing electrodes, a plurality of patch/module pairs may collect electrophysiological information synchronously. A plurality of metrics as collected from the different sites: amplitude, time delay, polarity, ratio between wave components of the signal, movement artifacts, breathing artifacts, etc. may be used to generate a series of location metrics. Such information may be compared against previously collected maps (e.g. generated from studies with correlated camera images and electrophysiologically collected signals, etc.) and compared against the data collected during a calibration test to determine the location of one or more patch/module pairs.

In aspects, additional kinematic information may be used to determine and/or refine the location determining aspects of a calibration procedure. One or more patch/module pairs may be equipped with one or more orientation determining sensors, such as one or more accelerometers, barometers, tilt sensors, gyroscopes, combinations thereof, etc. Information gleaned from one or more of such orientation determining sensors may be used in combination with one or more methods in accordance with the present disclosure to determine, enhance, confirm, etc. placement of the patch/module pairs on the subject.

The analysis may provide suitable information from which relationships between EKG data collected from each patch/module may be coordinated to form a higher level diagnostic function (e.g. such as to reconstruct a 12-lead EKG, etc.). Such a configuration may be advantageous for providing detailed diagnostic information from a subject without requiring precise electrode layout, application of a wired Holter monitor, etc.

In aspects, a system in accordance with the present disclosure may include a plurality of patches configured to coordinate simultaneous multi-site electrocardiographic signal capture on a subject. Such signal capture may include redundant monitoring of heart rate, regularity of heartbeats, synchronization of heart rhythm with other phenomena, detection of myocardial contraction, detection of P-waves, QRS complexes, ST-segments, and T-wave configurations, calculating/showing/displaying/analyzing the standard electrocardiogram (ECG) lead configurations (Limb leads I, II, III, AVR, AVL, AVF) and precordial leads (V1-V6), combinations thereof, and the like.

In aspects, a system in accordance with the present disclosure may include a plurality of patches, each patch including one or more electrodes. In aspects, such electrode arrangements may be bipolar, tripolar, quadripolar, or otherwise multi-polar. In one non-limiting example, a single patch may contain one or more electrodes, the one or more electrodes arranged so as to establish a (virtual) reference for the system. During operation, the system may simultaneously monitor signals from the plurality of electrodes (i.e. via each patch/module pair), possibly in conjunction with the virtual reference. Within a patch/module pair a plurality of such electrodes may be coupled directly through a corresponding bioamplifier (i.e. such as may be located onboard the corresponding module). During a monitoring session, the patch/module pair, a hub, a coordinating module, or the like may be configured to extract multipolar signals, to detect, to amplify, and/or to algebraically combine such signals with one or more other multipolar signals monitored at sites located elsewhere on the body of the subject. In this manner, standard and/or higher level EKG lead configurations may be derived from multipolar signals obtained from a plurality of patch/module pairs on a subject.

In another non-limiting example, patch/module pairs including bipolar or multipolar electrode configurations may be placed on a body at standard EKG locations (limb or precordial sites), but not physically connected to one another. One or more electrode sites within the arrangement may be automatically designated as 'references' for the purposes of intra patch signal comparison. In aspects, the system may be configured to designate creation of a 'virtual' reference, and 'virtual' (i.e. calculated) standard leads (limb and precordial) equivalent recordings, performed using mathematics/signal processing techniques (e.g. algebraic transformations based upon one or more of the monitored signals, an image of the patch arrangement on the subject, a network topology of the patches, etc.).

Such a configuration may be advantageous for partially or completely eliminating the necessity of physical interconnection of electrodes via direct wire leads. Thus, a system in accordance with the present disclosure may include a function for the mathematical combination of signals and/or supplemental data (e.g. orientation based images, orientation based sensor data, etc.) to derive a clinically recognizable EKG signal (e.g. a standard EKG signal that would include lead I, II, III, aVR, aVL, aVF, or the epicardial leads V1, V2, V3, V4, V5 or V6, etc.).

In aspects, one or more parameters for a signal transformation between patches, may be calculated from an image of the patches on the subject. Each patch may be given a coordinate vector determine from the position and orientation of the patch on the subject (i.e. optionally with respect to one or more standard lead application sites). The coordinate vector may be used in such calculations to calculate a standard lead configuration from a collection of patch/module pairs on the subject.

In aspects, an ad hoc arrangement of patch/module pairs may be used in harmony to provide redundant monitoring of physiologic parameters from the subject. Sensor fusion of such redundant signals may be used to substantially remove movement artifacts, reduce movement noise, determine a faulty connection on one or more modules, eliminate false alarms caused by movement or other physiologic processes (e.g. brushing teeth, eating, a physiological event, a seizure, an epileptic seizure, an asthma attack, a pulmonary event, wheezing, or the like).

In aspects, one or more signals, with the assistance of one or more parameters, maybe transformed from the signal as monitored, to a clinically recognizable signal. Such transforms may include a linear algebraic operation, a sum of waveforms, a difference of waveforms, and other more sophisticated signal processing methods such as frequency domain analysis, complex vector representation (amplitude and phase at the multiple sites), vector transformations, convolution or another signal processing technique.

In aspects, vector (complex real and imaginary components) combination of lead signals may be performed by an operably system in the time domain, or frequency domain for the purpose of transforming one or more signals into a clinically relevant equivalent, etc.

In aspects, a system in accordance with the present disclosure may include a plurality of patches or patch/module pairs to form a redundant (i.e. for reliable recording, to extract higher level coordination of data from various sites on a subject) physiologic monitor. Such a system may be configured to implement one or more algorithms to coordinate information from each pair to determine higher level functions, maintain operation when a component fails, maintain operation when one or more signals are corrupted (e.g. by movement, stretch artifacts, a poor body connection, etc.), identify components in the network, identify and/or indicate when a component needs to be swapped (i.e. hot swapping for continuous monitoring from the subject), combinations thereof, or the like.

In aspects, such modular monitoring solutions may be applied to a wide range of monitoring situations. Some non-limiting examples of such applications include hospital based monitoring of patients, remote monitoring of patients, heart-rate monitoring, electrocardiographic monitoring of fitness, athletic, aerobic activities, yoga, stress management, biomechanics and biometric monitoring systems (e.g. so as to monitor EMG, proprioceptive inputs, etc.), heart-rate variability training, heart-rate variability assessment, traumatic brain injury assessment, muscle tension assessment, tissue assessment (e.g. determination of fat content in tissues around the body, changes in fat content during workout, etc.), sleep studies, sleep monitoring, sleep apnea assessment, physiologic assessment of sleep state, sleep biofeedback, snoring analysis, bruxism monitoring, physiotherapy, event response (e.g. stroke capture and response, heart attack, heart attack prediction, atrial fibrillation, syncope, ST-segment depression or elevation, onset of myocardial ischemia, p-wave analysis, onset of snoring, night terrors, sleep walking, etc.), hydration and fluid management, long-term monitoring, gaming or computer input devices, product testing, marketing analysis, virtualization of emotional experiences, physiotherapy, combinations thereof, or the like.

In aspects, a system in accordance with the present disclosure may include one or more feedback components (e.g. a device with audible feedback, tactile feedback, visual feedback, combinations thereof, etc.), to provide a subject, coach, practitioner, caregiver, partner, or the like with information, commands, or prompts, pertaining to the physiologic and/or physical signals captured by one or more patch/modules arranged upon the subject. In aspects, such feedback may be used to enhance the sleep state of a subject, interrupt a sleep event to return a subject to a safe or comfortable sleeping state (e.g. interrupt a sleep walking event, a snoring event, a sleep apnea event, night terrors, nightmares, etc.). In aspects, such feedback may be analyzed in combination with the electrophysiological and/or physiologic signals to alter the state of the subject (e.g. the mood, the sleep pattern, the state of sleep, to prevent wake-up, to initiate wake-up, etc.).

In aspects, a feedback component in accordance with the present disclosure may include or be included in a wristwatch (e.g. a biometric watch, a smart watch, etc.). Such a wristwatch may include a display, a touch screen, or user input device, a tactile (i.e. vibrating) aspect, an audible feedback aspect or the like. Such feedback components may be used to convey signals, or metrics relating to the physiologic and/or physical signals to the wearer (e.g. the subject, a coach, a physician, a caregiver, a partner, etc.).

In aspects, a feedback component in accordance with the present disclosure may include a heads-up-display (HUD), such as may be provided by a pair of HUD ready glasses, Google Glass™, or the like. In aspects, the HUD may include visual representation of the physiologic and/or physical signals for a wearer (e.g. the subject, a coach, a caregiver, etc.), and/or signals or metrics related thereto or derived therefrom. In aspects, a plurality of such feedback mechanisms may be used to enhance the user experience, such as a combination of audible feedback (i.e. via a loudspeaker), and visual feedback (e.g. on a HUD, via a light emitting diode (LED), etc.).

In aspects, an augmented reality application may be envisaged using a pair of HUD ready glasses, or via a handheld device with both display and camera functionality (e.g. a tablet, etc.). In aspects, aspects associated with muscle exertion, electrocardiographic data, etc. may be superimposed onto movements associated with the monitoring site so as to highlight such activities to an observer. In one non-limiting example, heart-rate data may be translated into an amplitude parameter for pixel movements and overlaid onto the display or HUD over top of the torso of the subject as displayed in the image. In such an example, a physiotherapist may be able to visualize "exertion" of a muscle group of a subject as it is overlaid onto that particular muscle group during a monitoring session. The exertion may be compared against previous bests, in the context of physiotherapy, may be compared against capabilities (i.e. from previously collected history) and compared against maximal exertion levels, etc. so as to avert injury, optimize an exercise for a subject, maximize the exertion of a local muscle group within a safety window, monitor muscle fatigue during exercise, or the like. Such a system may be advantageous for allowing a user (e.g. the subject, a physiotherapist, a physician, a nurse, etc.) to assess one or more physiologic parameters of the subject while observing the subject or aspects thereof in a display (i.e. without taking attention away from the subject).

In aspects, one or patch/modules may include a vibrating actuator (e.g. an eccentric motor, an electroactive material actuator, etc.) configured so as to provide a local tactile sensation to the subject. The tactile sensation may be driven by one or more of the physiologic and/or physical signals, by an input from a coach, a caregiver, or the like. In aspects, a system in accordance with the present disclosure may be used to transfer touch sensation from a site without adequate feedback (e.g. a foot, a shin, a knee, a site of neuropathy, an injured region of the body, etc.), to an alternative site on the body, which still has functioning touch feedback. In aspects, a system in accordance with the present disclosure may be used to convey touch sensation between remotely located subjects, to convey haptic touch information from an object (e.g. a portion of a wheelchair, a bumper, etc.) to a site on the body of the subject.

In aspects, a patch/module worn by an alternative subject (i.e. a second subject) may be configured so as to provide tactile feedback related to the actions of the first subject (i.e. feedback based upon the physiologic and/or physical signals), so as to convey a sense to the alternative subject of such signals.

In aspects, a physiotherapist may wear one or more patch/modules corresponding to patches worn by the subject (i.e. a patient). The system may be configured such that physiologic signals and/or physical signals measured on the patient (e.g. electromyographic signals relating to muscle activity, kinetic data, respiration rate, edema level, exertion parameters, etc.) may be "felt" by the physiotherapist via one or more patch/modules worn thereupon. Such a configuration may be advantageous for improving the data available to a physiotherapist during a training session with a patient.

In aspects, a physiotherapist may wear a HUD ready glasses, Google Glass™, or the like, to which information relating to the physiologic and/or physical signals measured on the patient may be conveyed (i.e. in the form of audio and/or visual feedback). In aspects, the HUD ready glasses may include one or more tactile feedback elements, so as to provide the wearer with further sensations related to the signals.

In aspects, an application linking an instructor to a student is described herein. In aspects, the instructor may interact with one or more feedback devices (e.g. visual display, HUD ready glasses, tactile feedback device, audio feedback device, etc.) and the student may be coupled to one or more patch/modules in accordance with the present disclosure. In aspects, the instructor may obtain feedback from one or more of the patch/modules on the student pertaining to the physiologic and/or physical signals measured thereby. Such a configuration may provide the instructor with more detailed information that may be unavailable otherwise (such as being able to quantify exertion levels of a student, visualize one or more physiologic parameters of the student, capture information relating to fatigue, cardiopulmonary changes in the student, etc.).

In aspects, an application linking two or more partners is envisaged. In aspects, one or more partners may be fashioned with one or more patch/modules in accordance with the present disclosure and one or more feedback devices in accordance with the present disclosure. In aspects, the exchange of physiologic data from patch/module to feedback device may be used to enhance interactions between the partners, remotely link the partners (perhaps in real-time, pseudo real-time, etc.).

In aspects, a system in accordance with the present disclosure may include a plurality of patch/modules each in accordance with the present disclosure. The plurality of patch/modules may be configured to form at least part of a body area network (BAN). In aspects, the patch/modules may be wirelessly connected to a host device and/or to each other for purpose of communicating physiologic and/or physical signals, network configuration data, time stamps, patch/module configuration data, patch/module IDs, etc. In aspects, the patch/modules may form at least part of a star, line, mesh, tree, spanning tree, network topology to provide such communication.

In aspects, component operation on and data communication over the network may be coordinated through addition of a time stamp. The time stamp may be used by an associated processor to temporally compare data collected by a plurality of patches on a subject, between a patch on a subject and another recording device located in the environment, etc. One or more patch/module pairs may include a clock, an ultra-low power clock, for generation of the time stamp.

In aspects, each patch/module may be allocated a temporal window (i.e. temporally multiplexed) within which to broadcast a signal to the host and/or a commanding patch/module in the network. Such a configuration may be advantageous to coordinate significant amounts of data on a network within a limited number of channels.

In aspects, a system in accordance with the present disclosure may be applied to a stress monitoring application. Such a system may include one or more patches or patch/modules each in accordance with the present disclosure, attached to a subject. The system may be configured to measure one or more physiologic parameters from the subject (e.g. heart rate variability, sympathetic tone, muscular sympathetic nerve activity, galvanic skin response, skin sympathetic tone, electromyographic activity, respiration rate, etc.). Such information may be combined to form a metric relating to the stress state of the subject. Such a stress state may be represented by a feedback component in accordance with the present disclosure, as part of a biofeedback loop (e.g. a centering algorithm, a calming algorithm, etc.), provided in conjunction with a light and sound show, provided as an "emotional" input to a light and sound show, etc.

In aspects, the stress state may be used in conjunction with a biofeedback algorithm to help a subject lower the stress state during a monitoring session. Such a system may be advantageous for helping subjects reduce anxiety, reach a meditative state, realize when their stress state is elevated, help adjust respiratory rate, enter into a meditative state, etc.

In aspects, one or more patches and/or patch/module pairs may include one or more sensors configured to monitor one or more physiologic, environmental, and/or physical parameter locally on the subject. Some non-limiting examples of such sensors include electrophysiologic sensors (e.g. EKG, EMG, EEG, electroretinogram (ERG), EOG, respiration, bioimpedance, activity, etc.), temperature sensor (e.g. near to the skin, within a module, ambient [environmental], etc.), thermal gradient sensor (i.e. so as to calculate a heat transfer vector locally on the body of the subject, to estimate a core temperature), barometer, altimeter, accelerometer, gyroscope, humidity sensor, magnetometer, inclinometer, oximeter, colorimetric monitor (e.g. color change analysis of underlying tissue, for respiration, blood flow, pulse, etc.), sweat analyte sensor (e.g. so as to measure sweat constituents, salt content, etc.), galvanic skin response, neural activity (e.g. skin sympathetic activity), interfacial pressure sensors (e.g. for contact assessment, compliance measurement, blood pressure, etc.), flow sensor (e.g. airflow over a module, or the like), surface strain sensor (e.g. via integration of stretch sensors into the patch, evaluation of stretch along one or more electrical interconnect within the patch, integrated capacitive stretch sensors, etc.), a microphone, combinations thereof, and the like.

One or more patches and/or patch/module pairs may be configured so as to harvest power from a nearby power source (e.g. via inductive coupling, optical radiation, radio frequency waves, thermal gradients, kinetic energy, or the like). In aspects, one or more patches and/or patch/module pairs may include an antenna configured to communicate inductively with a nearby radio frequency power source. Such a configuration may be advantageous to work towards minimization of size and weight of the patch or patch/module pair, to reduce costs, recharge the modules without the need for physical connections, etc.

In aspects, an application for providing a physiologic input tool is envisaged. A system in accordance with the present disclosure may include one or more patches and/or patch/module pairs configured and arranged upon a subject so as to monitor one or more proprioceptive and/or electromyographic signals therefrom (e.g. such as from a muscle group, a bicep, a forearm, a finger, etc.). Such information may be coupled to a software program, such as a music generation program, a toy, a training program, etc. In aspects, the effort with which a muscle group, and/or appendage is moved may be used as an input to the software. In aspects, such input may be attributed to a musical note, an instrument, an avatar of the subject, etc. In aspects, such notes, instruments, etc. may be attributed to a particular patch and/or module, thus an orchestrated score may be generated from measurements made synchronously by a plurality of such patch/modules (e.g. with instruments, tones, etc. being emulated by a particular muscle group, etc.). Such a system may be advantageous for physiologic training for accident or stroke victims, for assisting with gait correction, as a means for treating depression, for entertainment, etc.

In aspects, such inputs may be coordinated across multiple subjects to orchestrate a coordinated event, collaborate on a musical or dance piece, etc. Particular movements may be used to adjust the tones of a musical stream (i e running in parallel with the activity of the subject), etc. Such tuning may be coupled with a gait analysis package so as to provide an elegant biofeedback system for the coupling of music with movement (i.e. such that the music is in tune when form of the movements matches an ideally determined structure).

Such movement may be coupled with a musical stream. In such cases, the movements may be used to reinforce aspects of the music (e.g. to reinforce beats of the music, etc.), but also to decrease particular beats, as the movements fall out of sync with the music.

In aspects, the physiologic tool may be used to determine an effort related to a given task, to map a particular movement, to a task space, etc. Such information may be useful for use in a training program (e.g. a running program to assist with training a student the biomechanics of the sport, etc.). In aspects, strategically placed patches may be used to capture electromyographic information from muscle groups during movement. In aspects, such information may be coupled to a biofeedback system to assist with the correction of movements made by the subject.

In aspects, such tools may be used to improve the gait of a subject, such as during physiotherapy, during long distance running, during athletic training, during a fitness routine, etc. In aspects, a system in accordance with the present disclosure may include a patch configured for placement over the gluteal muscle (e.g. gluteus maximus, gluteous medius, gluteus minimus) and monitoring during movement (e.g. during a running practice, during a fitness routine, etc.). The system may also include means for monitoring impact of the foot of the subject against the ground, means for determining the basic state of the gait of the subject, etc. (e.g. with a heel-strike sensor, with sensors maintained in one or more patches placed on the body of the subject, etc.). The relationship between the EMG monitored near to a gluteus muscle may be analyzed with respect to other aspects of the gait (such as timing in relation to a heel-strike event, a knee bent, a foot extension, etc.). The relationship may be used to help the subject correct their gait, so as to alleviate pain, reduce injury, recover from injury, improve performance, etc.

In aspects, a system in accordance with the present disclosure may be used to analyze, assess the quality of, and/or improve the physical output of a performance animal (e.g. a racehorse, a dog, a camel, etc.). Such a system may be advantageous for performing gait analysis, cardiopulmonary assessment, endurance assessment, etc. of the animal adapted from one or more methods in accordance with the present disclosure.

In aspects, a system in accordance with the present disclosure may be used to assess heart function (e.g. heart-rate, heart-rate variability, electrocardiographic information, respiration, etc.) of an animal, such as in the context of veterinary medicine, preventative veterinary medicine, home pet care, etc.

In aspects, one or more patches and/or patch/module pairs may include a stretch sensor, for evaluating a state of movement in the muscles underlying a patch on the subject (e.g. or across a joint, along an abdomen, along a spine, etc.). Such monitoring may be combined with EMG monitoring to give a more thorough session with a subject (e.g. so as to combine exertion with extension of muscular groups, joints, etc.). Such information may be advantageous for evaluating the extent of movement of a subject during an exercise. Feedback derived therefrom may be suitable for correcting gait, limiting such movement, thus reducing injury, as part of a treatment routine for Achilles tendonitis, etc. Such stretch sensing may be combined with general electrophysiological monitoring to remove a stretch related artifact from the signal. Such stretch related artifact may be removed by adaptively subtracting the stretch signal from the electrophysiological signal, so as to minimize the coherence between the two signals.

In aspects, a stretch sensor in accordance with the present disclosure may be embedded into a patch in accordance with the present disclosure. In aspects, a pair of interconnects may be coupled with a stretchable electrically conducting trace (optionally meandering in nature) on the patch. The stretchable electrically conducting trace may change impedance in accordance with stretch of the patch during use. Such stretch related changes in impedance may be used to determine the overall stretch to which the patch is subjected during use. In aspects, an alternative stretch sensor may embedded into a patch in accordance with the present disclosure. The alternative stretch sensor may include a pair of interconnects for communication with a corresponding module, the alternative stretch sensor including a first stretchy electrode (sized, shaped, and dimensioned to provide a stretchy electrode that responds to stretch preferably in a first direction), a soft dielectric film (e.g. a region of ink coating the first electrode), and a second stretchy electrode placed so as to sandwich the soft dielectric film between the first and second stretchy electrodes. The impedance (e.g. capacitance, ac impedance, etc.), as measured between the coupled interconnects, will change with the stretch of the patch. In aspects, the concepts provided herein for the integration of a conductivity based and impedance based stretch sensor may be combined to give a combination device, which may result in a higher sensitivity to stretch. In aspects, the baseline impedance of the stretch sensor may be measured by the module and used as a method for assessing the interconnection between a module and a correspondingly equipped patch. Such a configuration may be advantageous for monitoring one or more of tissue strain, posture, respiration, respiration depth, movement of digits, movement of joints, or the like. Such functionality may be integrated into a patch and a corresponding module for use a range of applications requiring stretch related information.

In aspects, such monitoring may be used to assist with one or more forms of exercise (e.g. any exercise that works and/or stretches the buttocks, for example). Such monitoring may be suitable for evaluating exertion, stretch, etc. during lunges, hip thrusts, climbing stairs, fencing, bicycling, rowing, squats, tennis, arabesque, aerobics, and various specific exercises for the buttock and lower limbs. The information obtained from one or more muscle groups may be used as feedback for training, biomechanics, exertions, etc. as relevant to the sport or exercise under study.

In aspects, such monitoring may be used to assist with powerlifting exercises which are known to significantly strengthen the gluteal muscles include the squat, deadlift, leg press, feet in squats, and good mornings (bend over with a bar on the shoulders with a light amount of weight). Such monitored information may be used to assist with exertion feedback, limiting movement, and the like, so as to provide a subject or trainer with information during the exercise, limit the risk of damage, optimize training, maximize performance gains, or the like.

In aspects, such monitoring may be applied to virtually any muscle group or groups on the subject. Such approaches as described herein may be adapted to serve a range of exercises and sports, so as to assist subjects, trainers, physiotherapists, and the like with improving performance, adjusting gait, monitoring progression of an injury, comparing capabilities to previous efforts, assess or assist with sexual dysfunction, etc.

In aspects, a system in accordance with the present disclosure may be configured for long-term wear by a subject. The system may include one or more patches and/or patch/modules in accordance with the present disclosure, configured to comfortably attach to the subject and remain attached for a prolonged period of time (e.g. days, weeks, greater than 3 weeks, etc.). In aspects, the patch may include a bioadhesive with suitable breathability for long term wear (i.e. with moisture vapor transmission rate (MVTR) in a range such that tissues underlying the patch do not undergo maceration but also do not sufficiently dry out so as to impede electrophysiological measurement thereupon). In aspects, the module may include a gasket arranged so as to bias towards a mating patch when the two are assembled (i.e. so as to form a substantially water tight structure).

In aspects, the module may include a moisture sensor and/or humidity sensor positioned so as to monitor the environment between the module and the patch during use. Such information may be advantageous for determining if the patch needs to be swapped out during use.

In aspects, such a system may be suitable for use as a heart-rate variability (HRV) monitor. In aspects, such a module may include circuitry or be programmed with a function to calculate HRV from an EKG or extracted heart-rate metric. Thus, physiologic signals pertaining to HRV, heart rate (HR), etc. may be conveyed from the module to the host during a monitoring session (i.e. as a means for reducing the amount of raw data to be sent from the module to the host during a session). HRV monitoring may be advantageous for gauging training recovery, for evaluating a subject who has experienced a traumatic brain injury (e.g. via a sudden impact, repeated impacts, etc.), to grossly interpret activity of the sympathetic nervous system, to evaluate an emotional state or response of a subject, or the like.

In aspects, a system in accordance with the present disclosure may be adapted to monitor impact to a subject during a monitoring session. In aspects, the system may include a patch and/or patch/module pair including an accelerometer, a gyroscope, an altimeter, a barometer, stretch sensor, and/or a magnetometer configured so as to measure a sudden impact on the patch during a monitoring session. In aspects, the module may include circuitry or be programmed to monitor data derived from the sensors so as to determine if an impact has occurred (e.g. a rapid change one or more of the sensor data streams, a change of sufficient magnitude, etc.). Such information may be directed to a trainer, a doctor, a coach, a parent, or the like to alert them to the impact. In aspects, such information may be useful to determine if an impact requires further investigation, etc.

A system in accordance with the present disclosure may be configured for analyzing traumatic brain injury of a subject. The system may include one or more patch/module pairs in accordance with the present disclosure sized, dimensioned, and configured for placement at one or more sites on the head (e.g. sites 50, 131, 137, 140 as indicated in FIG. 1a, along a neck, along a forehead, along a temple, behind an ear, etc.) forming a head mounted patch/module pair, and optionally elsewhere on the body (e.g. on the chest, over a muscle group, etc.) forming a second patch/module pair.

In aspects, the head mounted patch/module pair may include one or more electrodes for monitoring local physiologic activity (e.g. EEG, EOG, EMG, etc.), near the brain of the subject, one or more kinetic or kinematic sensors (e.g. accelerometer, gyroscope, barometer), one or more additional sensors (e.g. local bioimpedance, hydration, temperature), and one or more acoustic sensors (e.g. a down facing microphone). The head mounted patch/module pair, or a processor coupled thereto may be configured to capture signals related to the above sensors in a black box, virtual black box, rolling first in first out (FIFO) buffer, or the like. In addition a processor on or coupled with the head mounted patch/module pair may be configured to analyze the signals to determine the timing of an impact, the kinematics of an impact, etc. In aspects, the second patch/module pair may collect heart rate information, heat rate variability, further body based temperature, hydration, and/or kinematic information. Upon detection of an impact, the system may save the physiologic information captured prior to the impact so as to form a pre-impact dataset, and continue to collect physiologic and/or physical data so as to form a post-impact dataset. The system may include an algorithm configured to automatically compare the pre-impact and post-impact datasets to assess the response of the subject to the impact. In aspects, an apparent change in heart rate variability, a change in the EEG, or EMG collected by the head mounted patch/module pair, or the like may be a strong indication that the subject was adversely affected by the impact. In aspects, the system may be configured to generate an alert, a report, an alarm, etc. upon determination of such a response.

The system may include an algorithm (e.g. either incorporated into a processor on a patch/module pair, in a processor coupled thereto, etc.), configured to analyze temperature, heat transfer, hydration level, or the like from the subject. Such information may be combined to form a metric relating to dehydration, an over temperature, and/or exhaustion state of the subject from which further action may be taken (e.g. generate an alert, an alarm, a report, feedback to the subject, to a coach, to a parent, etc.).

In aspects, a system in accordance with the present disclosure may be adapted to monitor thermal stress of a subject during a monitoring session. In aspects, the system may include one or more patches and/or patch/module pairs including one or more temperature sensors, thermal gradient sensors, hydration sensors, core temperature estimating sensors or algorithms, etc. so as to capture a relevant temperature of the subject during a monitoring session. In aspects, the system may include a feedback component in accordance with the present disclosure to convey such thermal information to a coach, a trainer, a physician, a parent, a race coordinator, etc.

In aspects, one approach for forming a core temperature estimating sensor in accordance with the present disclosure includes providing a patch in accordance with the present disclosure, the patch including at least one temperature sensor (e.g. a microcircuit based temperature sensor, a thermocouple, a bimetal strip, etc.), the patch configured so as to mate with a corresponding module, the module including one or more additional temperature sensors. The combination patch/module pair thus includes a plurality of temperature sensors (e.g. included in the patch, included in the module, etc.). Heat transfer from the adjacent tissues past the plurality of temperature sensors and into the surrounding environment will follow different pathways. The patch and/or module may include a plurality of controlled pathways with known heat transfer coefficients (e.g. such that the ratio of heat transfer coefficients between the pathways can be reasonably predicted). In aspects, the heat transfer coefficient along the pathway between the skin and each sensor may be known, and the heat transfer coefficient between each sensor and the surrounding environment may be known (e.g. to within a ratio). In aspects, the patch/module pair may include an additional temperature sensor, positioned so as to monitor a temperature near that of the surrounding environment (e.g. such as exposed on the surface of the module, on the surface of the patch pointing way from the body, collected from a local hub, from a smartphone, from a local weather report, or the like).

The temperature at a site remote from the patch (e.g. deeper into the tissue), may be estimated from the plurality of temperature readings in combination with thermal pathway coefficients. In aspects, temperature measurement may be improved by single point calibration with a traditional core temperature sensor. After calibration, the temperature measurements may be sufficient to estimate changes in core temperature over time while the subject wears the patch/module pair. In aspects, a plurality of patches worn by a subject may be used to improve an estimate of core temperature thereof.

In aspects, one approach for forming an embedded hydration sensor into a patch/module pair may include, embedding a plurality of electrodes into a patch in accordance with the present disclosure (e.g. 2 or more electrodes, 4 electrodes, etc.). The corresponding module may include a signal generator and one or more bioamps (or multiplexing circuits in combination with a reduced number of bioamps, etc.), the signal generator configured so as to provide a signal between two or more of the electrodes (e.g. in a frequency range of generally between 1 hertz (Hz) and 10 GHz, 1 kHz and 10 MHz, 5 kHz and 1 MHz, or the like, at multiple frequencies, swept over a range of frequencies, etc.), while the bioamps are configured to capture one or more signals from two or more of the electrodes. The processor, gate array, digital signal processor, or an associated microcircuit, configured to analyze the captured signals to determine a bioimpedance of the nearby tissues. Such a bioimpedance may be advantageous for monitoring a change in fluid level in the adjacent tissues. Such a configuration may be advantageous for assessing the fluid level of a subject. In aspects, two or more of the electrodes may be coupled to a second bioamp (an additional amplifier, the same amplifier, etc.), the second bioamp configured to capture a biosignal (e.g. EKG, HR, EMG, EOG, EEG, ERG, or the like) from the electrodes. Assessment of the signals at a plurality of frequencies may provide sufficient data to extract electrode impedance, from the reading, to estimate tissue impedance at different frequencies, and to extract the extracellular (ECW), intracellular (ICW), and total body water (TBW) content from the tissues under analysis by the patch/module pair.

In aspects, the patch/module pair includes an antenna, the antenna coupled to convey one or more signals to an external hub, additional patch/module pair, etc. The antenna may be coupled to the adjacent body, such that during signal transfer, the impedance of the antenna varies with water concentration of the adjacent tissues. During operation, changes in the S11 parameter for the antenna may be monitored, so as to determine local fluid levels in the adjacent tissues, while also transferring data back and forth for completing other functions.

In aspects, a second approach for forming an embedded hydration sensor into a patch/module pair may include, embedding a visible, near infrared, or infrared emitter into the module such that, upon coupling of the module with a corresponding patch, the emitter is arranged such that radiation emitted therefrom is directed into the tissues of the subject, the module including a photodetector (e.g. a narrow band detector, centered generally about 510 nanometer (nm), 578 nm, 630 nm, 750 nm, 1000 nm, 1180 nm, 1040 nm, 1210 nm, 1300 nm, 1500 nm, a multi-band detector <combinations thereof>, a broad band detector, multiple detectors, etc.) to capture reflected or back scattered radiation from the skin from the emitter. In aspects, the corresponding patch may be configured with a window transparent to, or polarized so as to exclude light, such that when the module is coupled to the corresponding patch, the emitted and/or detected light pass through the window. In aspects, the module may include a corresponding cross polarized window, such that the two windows may be used in unison to exclude light from the surroundings, eliminate incident light from the emitter reaching the detector, etc. Such a configuration may be advantageous to improve signal to noise ratio in such readings.

The collected signals may be used to assess the tissues adjacent to the patch/module pair. In aspects, the patch/module pair may include or be coupled to a processor equipped with an algorithm, the algorithm configured to interpret the collected signals and determine the state, analyte concentration (e.g. oxygen, water, lipid, melanin, myoglobin, collagen, elastin, etc.), and/or composition of a fluid and/or tissue adjacent to the patch/module pair. In aspects, the algorithm may be configured to extract a metric related to water content of the tissues, the metric suitable for use as a surrogate for hydration of the subject. In aspects, the collected data may be analyzed so as to extract oxygen blood concentration, water, lipid level, or the like. Such a configuration may be advantageous for providing a consistently oriented measurement configuration, with substantially minimized external influences, highly controlled pressure on the tissues (e.g. near zero contact pressures, through to consistently controllable pressures with inclusion of a feature on the patch), exclusion of ambient light, and cost reduced measurement configuration. When placed near to an artery, the configuration may be suitable for obtaining a local pulse signal (i.e. for combination with a plurality of patch/module pairs to determine a time-of flight based blood pressure reading on the subject).

In aspects, the emitter may be pulsed with a duty cycle, and the sensory circuits may be configured so as to operate with a duty cycle. Such a configuration may be used so as to substantially conserve power during operation.

Such a configuration may be combined with one or more sensors in accordance with the present disclosure (e.g. such as electrodes into the patch, etc.), so as to provide a higher level of diagnostic information.

Such a system may be combined with one or more features in accordance with the present disclosure to provide diagnostic input relating to assessment and capture of a sleep apnea event, choking, limb status, post-operative tissue flap status, or the like (i.e. assess local blood flow to a tissue site covered by the patch/module pair).

According to aspects there is provided, a patch/module pair in accordance with the present disclosure, the patch configured for placement onto a body part after a surgical operation (e.g. after a plastic surgery, a tummy tuck, a breast augmentation, a stoma formation, a fistula repair, a wound closure, a tissue transplant, etc.), the patch configured so as to shape the tissue to which it has been attached (e.g. provide a restraining shape, so as to enhance the healing of the procedure, minimize scaring, heal in a particular configuration, under a particular stress state, etc.), the module and patch including one or more sensors in accordance with the present disclosure, the sensors arranged and oriented so as to assess the health of the tissue. In aspects, the patch/module pair may include a hydration sensor in accordance with the present disclosure, to assess the hydration state of the tissues, a change in color of the tissues, a change in oxygen saturation level, or the like. The module may include a processor equipped with an algorithm to assess changes in the tissue state and generate an alert, an early warning, etc. if the changes are not conducive to a successful surgical outcome for the patient.

In aspects, the system may include a feedback component in accordance with the present disclosure, such as a pair of HUD ready glasses, such as Google Glass™ configured to be worn by a data recipient (e.g. a trainer, a coach, the subject, a parent, a physician, a nurse, a caregiver, etc.). The feedback component may be configured to alert the wearer of the thermal state of the subject (e.g. so as to warn of heat exhaustion, dehydration, etc.). In aspects, a feedback component on a single data recipient (e.g. a trainer, a coach, a race coordinator, etc.) may be configured to display data corresponding to an entire team, a class of students, a group of competitors, etc.

In aspects, thermal monitoring, impact monitoring, and HRV monitoring may be combined within a single system to provide a heath monitor for use during physical training, sports, fitness events, etc.

In aspects, a system in accordance with the present disclosure may be configured to provide one or more of a cuff-less blood pressure monitor (e.g. via inclusion of one or more patch/module pairs equipped with an interfacial pressure sensor, local pulse assessment sensor, a compliance sensor, or the like), a modular EKG monitor (i.e. via inclusion of one or more patches or patch/module pairs configured to monitor local electrophysiological information from the torso of a subject), a modular EMG monitor (i.e. via inclusion of one or more patches or patch/module pairs configured to monitor electrophysiological information in the vicinity of functional muscle groups on the subject), an edema assessment system (i.e. via inclusion of a patch or patch/module pair configured to measure water content of tissues in the vicinity of the patch as placed onto the subject), a blood clot detection system (i.e. via inclusion of two or more patches to monitor changes in blood flow dynamics between the patches as placed along one or more appendages of a subject, e.g. flow dynamics as measured along the leg), a peripheral vasculature diagnostic system (e.g. via inclusion of one or more patches to monitor arterial flow, arterial brachial index, etc.), or utility in the monitoring of heart failure patients, patients that are short of breath, chronic obstructive pulmonary disease (COPD) patients, patients suffering or suspected of suffering from sleep apnea, valvular disease, metabolic syndrome, etc. to track cardiopulmonary parameters as indicators of disease state/progression, diagnostics, and/or therapeutic progress with the disease.

According to aspects a system for monitoring blood pressure of a subject is provided, the system including a plurality of patch/module pairs, at least one patch module pair configured to measure an electrophysiological signal in accordance with the present disclosure (i.e. an EKG patch), and at least one or more patch module pairs configured to measure a local signal relating to blood oxygen level and/or pulse in a tissue volume in the vicinity thereof (e.g. via optical methods, bioimpedance, spectroscopic, local counter pressure assessment, or the like in accordance with the present disclosure) (i.e. a local pulse patch). The EKG patch configured for placement on the torso of the subject, and one or more of the local pulse patches configured for placement at least on an extremity of the subject (e.g. on the torso and on an extremity, near a wrist, on an arm, on a leg, etc.). The system may include a time stamp in accordance with the present disclosure such that the timing of the electrophysiological signal obtained by the EKG patch may be compared to the pulse response signal(s) obtained by the local pulse patch(es). A time delay(s) between a reference wave on the electrophysiological signal (e.g. onset, peak, etc. of a QRS complex), and the pulse signal (e.g. pulse peak, valley, etc.) of the local pulse patch(es) may be generated to assess blood pressure. The time delay(s) may be combined to generate a blood pressure metric for the subject. In aspects, one or more of the patches may include a kinematic sensor, positioning sensor (e.g. a barometer, a tilt sensor, etc.), to determine a positioning between the patches in accordance with a local gravitational field (so as to calculate a head loss, etc. between the patches). The positioning between the patches may be assessed by an algorithm in combination with the time delay(s) to improve the estimate of the blood pressure of the subject. In aspects, the system may include or interface with a blood pressure measurement device (e.g. a blood pressure cuff), the measurement taken by the blood pressure measurement device used to calibrate the algorithm, so as to further improve the blood pressure estimate. In a usage case, the blood pressure reading may be calibrated daily, weekly, etc. so as to maintain an acceptable accuracy thereof. Such a configuration may be advantageous to provide a non-invasive, comfortable ambulatory blood pressure monitor for assessing real-time changes in blood pressure of a subject during a prolonged monitoring period.

In aspects, one or more patches or modules may include a microphone, optionally directed so as to collect an audio signal from an adjacent skin surface. The microphone may be used to measure an acoustic signal from the subject in the vicinity of the patch or module. In aspects, the patch or module may include acoustic isolation such that the microphone doesn't pick up substantial ambient noise. In aspects, the microphone may be suitable for capturing data relating to heart murmur, a sleep apnea event, an airway obstruction, wheezing, an asthmatic event, weeping, joint noise, or the like.

In aspects, a system in accordance with the present disclosure for assessing traumatic brain injury may include a microphone within a module and/or patch, the microphone configured to monitor an acoustic signal related to bone movement, echo, and bone on bone impact associated with a potentially concussive impact applied to the subject. Such information may be combined with electrophysiological monitoring, or the like in accordance with the present disclosure to assess the influence of an impact on a subject.

In aspects, a system in accordance with the present disclosure may be adapted for follow-up of a joint replacement surgery. In aspects, the system may include one or more patches and/or patch/module pairs configured for placement in the vicinity of the joint, or arranged so as to monitor muscle movement or exertion associated with the joint. In addition the to the physiotherapy related aspects discussed throughout the present disclosure, the patch and or module may be configured to monitor one or more aspects of the joint (e.g. joint acoustic signature, thermal changes in the joint during use, joint impacts, etc.). The system may be configured so as to analyze such data to predict a lifetime of the joint, predict patient outcome, detect early signs of grinding, or the like.

In aspects, one or more patches and/or modules in accordance with the present disclosure may include a micro compliance sensor and/or an interfacial pressure sensing element so as to assess local changes in blood pressure, pulse, arterial pressure, or the like. The microcompliance sensor can be used to assess local tissue stiffness, or placed in close proximity to vascular structures in order to measure vessel stiffness and/or pulse pressure. Arrangements of such sensors along the extremities of a subject may be advantageous for assessing blood flow (i.e. via pulse time of flight measurements), blood pressure, pulse, or the like. A microcompliance sensor may include a deformable part, and a Micro-Electro-Mechanical system (MEMs), or optoelectronic sensing element to determine the state of deformation of the deformable part. In one non-limiting example, a microcompliance sensor may include an elastomeric deformable part, configured so as to move when a pressure is applied thereto, and an optical source and detector, configured to deliver a light source into the deformable part and monitor a return signal therefrom. Changes in the return signal may be correlated to the deformation state of the deformable part, thus providing the necessary feedback. Such a patch may be advantageously applied to a blood pressure monitoring system as a local pulse patch in accordance with the present disclosure.

In aspects, a system in accordance with the present disclosure may be configured for simplified use by a subject. One or more patches or modules may include an interfacial monitor to determine if the system is attached to the subject. Upon attachment, the module may be configured to determine the quality of the attachment, and connect to the BAN to start a monitoring session. In aspects, one or more patches or modules may include a battery monitor, interface monitor, etc. to determine if the patch should be swapped out or not during a monitoring session. In aspects, a plurality of patches or patch/module pairs may be attached to the subject such that a level of redundancy in the monitoring process may be achieved. In such situations, the system may continue to effectively monitor the subject even when one or more patch/module pairs is not properly attached, low on power, etc. Such a configuration may be advantageous for reducing the number of false alarms that may be detrimental to the monitoring process in a hospital, for example.

In aspects, to further simplify use, one or more modules in accordance with the present disclosure may include one or more orientation sensor, motion sensor, barometer, or the like and/or means for determining the network topology (ex. wireless signal strength between modules in the network, user method for identifying the module, etc.). Such information may be used to automatically or at least partially determine the placement of the module on the subject.

From such an assessment, the relative positions and orientations of modules in the network and on the subject can be determined and used to improve the clinical quality of a multi-module monitoring session (i.e. by generating a standardized EKG lead configuration from the available configuration), improving the accuracy of a multi-lead EKG, identifying a heart location in comparison with the modules, and/or determining the orientation of the subject (e.g. standing, sitting, supine, etc.).

In aspects, one or more of the modules, a host, or a system coupled thereto may be programmed with a function to determine the effectiveness of the capture of the intended data by one or more of the patch/module pairs (i.e. the quality of the collected data) and to determine whether such data should be trusted in the collected data stream or not. In aspects, the data may be analyzed to determine if a particular data stream has been corrupted by movement (e.g. due to EMG interference, relative movement at the site of the patch, stretch based artifacts, etc.), by water ingress (e.g. due to moisture entrainment into the module, interface, etc.), poor connection to the subject (e.g. via determination of high electrode impedance, etc.), or the like. Upon detection of an issue, the algorithm may be configured to dismiss data collected form that patch/module pair, de-emphasis such data, etc. until the issue is resolved. The algorithm may be configured to assess whether the data collected from the remaining patches is sufficient to capture the sought after information (e.g. sufficient data to rule out a heart attack, to assess atrial fibrillation, to assess syncope, to determine if a syncope event is cardiogenic, reflex, and/or orthostatic hypertension, etc.), and continuing with monitoring if this is the case, while raising an alarm, alert, etc. if the quality of recording cannot be maintained in light of the issue. Such algorithms may be advantageously implemented to assist with managing a system in accordance with the present disclosure.

In aspects, one or more systems in accordance with the present disclosure may be coupled to a control console (e.g. a computer terminal, a system management software front end, a server, a virtual server, a cloud based service, etc.) whereby aspects of the system(s) may be assessed and altered rapidly to improve workflow therewith, or the like.

In aspects, a system in accordance with the present disclosure may be coupled with a patient management system, configured to quantitatively manage customer/patient progress, improvement, and engagement with a therapy, exercise routine, local community event, etc.

In aspects, a system in accordance with the present disclosure may be adapted for use within a home care setting. In such settings, data collected by the host (e.g. a smartphone, a WiFi® hub, a Bluetooth low Energy® hub, etc.) may be sent onto a data center for further analysis. Such information may be collected efficiently without interfering with the subject's daily routine, etc.

In aspects, a system in accordance with the present disclosure may be configured for entertainment purposes. Such a system may include one or more functions to report (e.g. notify, Tweet™, m2m text message, post, communicate, etc.) one or more aspects of a subject's physiologic and/or physical response to a peer group. In aspects, such a system may include connections to a theme park customer management system, a product evaluation feedback system, etc. In one non-limiting example, a system in accordance with the present disclosure may be configured to monitor and report the heart-rate of a subject during an amusement park ride (e.g. during a roller coaster, haunted house, etc.), during an extreme sport (e.g. sky diving, water skiing, hang gliding, etc.), or the like, and to report such metrics to a peer group associated with the subject, optionally along with one or more contextual data points (e.g. roller coaster name, subject location, etc.). Such information may be reported during peak physiologic events (e.g. during peak heart rate, during peak respiratory rate, etc.). Such information may be used to quantitatively track customer response to a product, process, to track subject "activities", or the like.

In aspects, a system in accordance with the present disclosure may be configured to communicate one or more aspects of the collected data, or signals/metrics derived therefrom, goals achieved, or the like to a social forum associated with the subject (e.g. a social network, Facebook™, Instagram™, Google+™, Patient's Like Mc™, or the like). Such information may be included in a feedback loop (e.g. so as to encourage a patient, congratulate a subject on an outcome, etc.). In aspects, one or more processors integrated with the social forum may be configured to automatically analyze the collected data and produce one or more metrics relating to disease progression, health state, performance, events (e.g. excitement, amusement park reporting, product usage feedback, intimacy assessment, stroke, physiotherapy progress, etc.).

Body Interface Aspects

A patch in accordance with the present disclosure may include a substrate, one or more interconnects fastened to the substrate, each interconnect including one or more connectors, configured, and dimensioned for interfacing with a module in accordance with the present disclosure. The patch may include one or more sensors in accordance with present disclosure coupled with the substrate, arranged so as to interface with an adjacent skin surface after placement on a subject, the sensors electrically, mechanically, and/or optically coupled with one or more interconnects. In aspects, one or more of the sensors may be an electrode. Optionally the patch may include a microcircuit embedded in or attached to the substrate or one or more interconnects, configured to convey information between the interconnect and one or more associated sensors included in the patch. In aspects, the patch may include an adhesive or attachment layer coupled with or integrated into the substrate, configured such that the patch may be applied to a surface of a subject (i.e. the skin of the subject).

In aspects, the patch may be configured such that it is sufficiently breathable to water vapor and/or oxygen that it can be worn comfortably by a subject for a prolonged period of time. In aspects, one or more regions of the patch may be configured with a moisture vapor transmission rate of greater than 200 $g/m^2/24$ hrs, greater than 500 $g/m^2/24$ hrs, greater than 2,000 $g/m^2/24$ hrs, etc. In aspects, one or more regions of the patch may be configured with a moisture vapor transmission rate of less than 20,000 $g/m^2/24$ hrs, less than 12,000 $g/m^2/24$ hrs, less than 8,000 $g/m^2/24$ hrs, or the like. Such moisture vapor transmission rate (MVTR) may be approximately determined using ASTM standard ASTM E96: Standard test methods for water vapor transmission of materials.

In aspects, the substrate or the patch in accordance with the present disclosure on the whole may be stretchable, so as to maintain operation while stretching in conjunction with the surface of the subject where it is attached (e.g. on the torso, across a joint, along a muscle, etc.). In aspects, the substrate or the patch on the whole may be highly elastic so as to easily stretch with the skin without nicking, curling, lifting from the skin surface, etc. Such a soft and thin patch may be advantageous for substantially maximizing comfort of the subject, reducing skin irritation, etc. thus improving subject compliance for long term monitoring.

In aspects, an adhesive layer in accordance with the present disclosure may include a dielectric or an electrically conducting adhesive, a biocompatible pressure sensitive adhesive, a gel layer, a hydrogel layer, or the like. In aspects, the adhesive layer may include one or more patterned features, configured so as to provide regional variation in adhesion, to isolate regions of the skin surface in one region from adhesive located in other regions, and the like. In aspects, the adhesive layer may include a biodegradable polymer.

In aspects, one or more regions of an adhesive layer in accordance with the present disclosure may be electrically and/or ionically conducting and patterned onto the substrate so as to provide adhesion thereof to a skin surface. The substrate may be patterned with one or more electrical traces configured to connect one or more electrodes with one or more connectors in an interconnect each in accordance with the present disclosure. In aspects, the electrical traces may be isolated from one or more regions of the adhesive layer (e.g. with a dielectric overcoat, via a passivation layer, etc.) so as to form regions of substantial isolation and regions of substantial connection between an attached skin surface and the electrodes and/or electrical traces in the patch.

In aspects, the patch may include an adhesive layer coupled with the substrate for making contact with the subject. To maintain a breathable, flexible interface, the thin adhesive layer may have a thickness of less than 50 um, less than 25 um, less than 12 um, less than 6 um, less than 4 um, etc. The thin adhesive layer may be formed from a pressure sensitive adhesive (e.g. an acrylic adhesive, a silicone adhesive, a hot melt pressure sensitive adhesive, a thin hydrogel adhesive, etc.), a silicone gel adhesive, a hydrogel, a biopolymer, a hot melt adhesive, combinations thereof, or the like. The thin adhesive layer may be formulated in combination with one or more salts, so as to impart suitable ionic/electrical conductivity to communicate electrically between one or more aspects of the patch and the skin surface of the subject.

In aspects, the adhesive layer may be formulated with one or more soothing constituents, such a menthol, mint, honey extract, aloe, essential oils (e.g. lavender oil, vanilla oil, camphor, cinnamon extract, orange extract, etc.). Such soothing constituents may be added to the adhesive formulation during fabrication, misted onto the patches, and/or added to the packaging of the product, etc.

In aspects, the adhesive layer may be patterned so as to form a heterogeneously distributed adhesive pattern to an adjacent skin surface, to form regions of varied MVTR, as a means for reducing the amount of adhesive required to interface with the subject, etc.

In aspects, one more elements within the adhesive layer, the substrate, or the patch may include a hydrogel, including a biocompatible click chemistry based gel (i.e. for improved strength and minimization of gel residual transfer to the subject during a monitoring session), a radiation cured gel, a high tear strength gel, an ionically conducting gel, an intrinsically conducting (e.g. combined with conjugated polymers, in situ polymerized conjugated polymers, etc.).

In aspects, the patch may include a ferromagnetic layer or patterned region, ferromagnetic layer with adhesion (i.e. for integration into the adhesive layer), ferromagnetic material with combined electrical conductivity (i.e. for combined attachment and function as an electrical interconnect), etc.

In aspects, a patch in accordance with the present disclosure may include a substrate, coupled to the thin adhesive layer. In aspects, the substrate may be formed from a sufficiently thin polymeric material (e.g. a polyester, a polyurethane, ethyl vinyl acetate, polyether block amides, an elastomer, polyisobutylene, polyisoprene, a thermoplastic elastomer, butadiene block copolymer, styrene butadiene carboxy block copolymer, vinyl methyl silicone, polysiloxane, styrene ethylene butylene styrene copolymer, styrene butadiene, polyurethane, acrylonitrile butadiene, isobutylene isoprene butyl, hydrogenated nitrile butadiene, fluorocarbon rubber, fluoro silicone, fluorinated hydrocarbon, polybutadiene, ethylene-acrylate rubber, polyester urethane, etc.). To maintain a sufficiently flexible, comfortable and/or breathable interface for a subject, the substrate may be formed from a thin polymeric material with thickness less than 50 um, less than 25 um, less than 12 um, less than 8 um, less than 4 um, etc. In aspects, the substrate may be formed at least partially from a thin polyurethane substrate with thickness less than 13 um. In aspects, the polyurethane film may exhibit an MVTR of greater than 200 $g/m^2/24$ hrs, greater than 400 $g/m^2/24$ hrs, greater than 1,000 $g/m^2/24$ hrs, greater than 4,000 $g/m^2/24$ hrs. Such a configuration may be advantageous for providing a low profile, soft, conforming disposable adhesive part that may stretch and move with the adjacent tissues of the subject during an ambulatory monitoring session.

In aspects, one or more regions of the substrate may be coated with a lubricous or otherwise low friction material so as to provide a desirable surface texture to a subject when placed during a monitoring session (so as to limit nicking of the patch during a monitoring session, etc.). In aspects, the substrate may be coated with a thin lubricious coating of a silicone and/or silicon micro/nano bead layer. Such a coating may provide a soft, lubricious feel for the substrate while maintaining a hypoallergenic quality and further limit nicking during a monitoring session.

Alternatively or in combination, the patch may include a thin ionically and/or electrically conducting adhesive, coupled to the substrate and/or the thin adhesive layer so as to make physical contact with a subject during placement on the body of the subject. The ionically and/or electrically conducting adhesive may be one or more adhesive known in the art. In aspects, the ionically and/or electrically conducting adhesive may include a hydrogel.

In aspects, the patch may include an electrically conducting member (e.g. a stud, an electrical trace, an electrical patch, a wire, a coil, a thin film conducting trace, a printed electrical trace, etc.) for interfacing an operably connected module to one or more sensors (e.g. sensors in accordance with the present disclosure, electrodes, etc.), the thin adhesive layer, and/or the ionically and/or electrically conducting adhesive. The electrically conducting member may include a ferromagnetic material (e.g. iron, nickel, etc.) so as to provide a bias force for holding the patch to an associated module including one or more mating magnetic elements. In aspects, a ferromagnetic material region may be added to the patch such that the conducting layer would be sandwiched between the ferromagnetic material region and a magnetic connector on a corresponding module. Such a configuration may be advantageous to maintain a conductive interface between the module and the patch when mated together, without the need for a large mechanically interlocking connection between the patch and the module.

In aspects, a patch in accordance with the present disclosure may include a module-patterned adhesive structure oriented so as to interface with an operably placed module in accordance with the present disclosure during placement onto the body of a subject. In aspects, the module-patterned adhesive may be formulated so as to provide a reversibly attachable adhesive option for a corresponding module. In aspects, the module-patterned adhesive may be formed from a silicone adhesive, a low tack pressure sensitive adhesive, or the like.

In aspects, the patch may include a substrate formulated so as to provide both support (e.g. to one or more interconnects, sensors, microcircuits, etc.) and means for securing the patch to a subject (i.e. attachment means to a skin surface). In aspects, the substrate may be formed from a suitably porous, hydrophilic material. The porous hydrophilic material may be configured to wick fluids from the surface of the skin during attachment, so as to form intimate contact therewith and to bond to the skin during the period of intimate contact (i.e. to establish Van der Waal bonds thereto).

In aspects, a patch in accordance with the present disclosure may include two or more electrodes, patterned so as to measure a local electric field (e.g. a bipolar, multipolar reading, a field vector, etc.) on the surface of the subject during a monitoring session. The local electric field may be used in part to construct one or more electrocardiographic signals from the subject during a monitoring session. In aspects, one or more patches may include an increased number of electrodes, and such electrodes may be monitored to glean further information related to electric field orientation and propagation over the body of the subject during the monitoring session. Such information may be advantageous in so far as obtaining diagnostic information from a subject during a monitoring session as well as to assist in constructing higher lead count EKGs from an array of patches (e.g. extracting a 12-lead EKG equivalent from an array of patches attached to the subject, etc.).

In aspects, an electrode in accordance with the present disclosure may include one or more electrode features (e.g. microfibers, barbs, microneedles, spikes, or the like), arranged and dimensioned so as to penetrate into the stratum cornium of the skin during an attachment and/or during an engagement procedure. In aspects, the electrodes may be made to puncture and/or penetrate through the stratum corneum during placement, an attachment procedure, and engagement procedure, etc. The electrodes may be forced to cause penetration of one or more of the electrodes or electrode features into the skin wall so as to enhance the electrical connection thereto during a monitoring session. In aspects, one or more electrodes may be configured for microscopic or macroscopic spatial recording. In aspects, one or more of the electrodes may include a barb to retain the electrode into the skin of the subject after engagement. Such a configuration may be advantageous to obtain a low impedance, reliable interface with the subject during a monitoring session, to assist in decreasing movement artifacts, and/or help in decreasing stretch based artifacts in an acquired electrophysiological signal.

In aspects, one or more electrode features in accordance with the present disclosure may be spring mounted, such that they do not normally engage directly with the skin surface after attachment of the corresponding patch thereto. Upon pressure application to the electrode by an external entity (e.g. a thumb, an applicator, etc.), the electrode features may be biased towards the skin, thus penetrating the stratum corneum and enhancing the electrical connection thereto during the monitoring session. In aspects, once engaged with the skin, the electrode features may remain in place for the duration of the monitoring procedure. In aspects, after removal of the biasing force (i.e. the force provided by the external entity) the electrode features may withdraw from the skin, leaving an array of micropunctures through the stratum corneum for enhanced electrical contact therewith.

In aspects, the electrode features may be coupled to a region or layer of an electrically and/or ionically conducting substance (e.g. a gel, a hydrogel, a salt laden hydrogel, an intrinsically conducting hydrogel, etc.), and penetrate through the substance when engaging with the underlying skin. In aspects, the substance region or layer may provide a biasing force to disengage the electrode features from the skin layer after a brief engagement with the skin. Such a configuration may be advantageous to provide a high quality interconnect between the patch electrodes and the skin of the subject, while maintaining a comfortable environmentally controlled contact with the skin and protecting (and optionally maintaining) any micropunctures in the stratum corneum during the monitoring session. The initial engagement of the electrode features with the skin may assist in lowering the local impedance of the stratum corneum, so as to improve contact between the electrode and the body, and reduce stretch and movement based artifacts, but a gel based intermediary may maintain the lowered impedance throughout a monitoring session, or over a prolonged period of time without causing undue irritation or discomfort for the subject.

In aspects, the electrode features may be configured and dimensioned so as to penetrate less than 2 mm into the skin, less than 1 mm, less than 0.5 mm, less than 0.2 mm, or the like during engagement. In aspects, the electrode features may include one or more microneedles with a length of greater than 0.1 mm, greater than 0.25 mm, greater than 0.5 mm, greater than 1 mm, or the like.

In aspects, one or more electrode features may be coated or impregnated with a medication (e.g. an anesthetic, a steroid, a skin care product, aloe, a therapeutic agent, a pain killer, etc.) configured to attach to or diffuse into the adjacent tissues during engagement thereof. In aspects, the electrode features may include one or more medicated tips (e.g. tips formed from a medication filled biodegradable polymer, sugar, etc.) in the form of an arrow structure, a barb, etc. so as to maintain the electrode feature in place after an initial engagement with an adjacent tissue (i.e. so as to form an indwelling electrode—tissue arrangement). Such a configuration may improve retention of the tips within the tissues. Biodegradable or soluble tips may be advantageous to provide a slowly disengaging interconnection between the electrode features and the tissues over a desired time frame.

In aspects, a patch in accordance with the present disclosure may include one or more electrically conducting and/or one or more electrically insulating features (e.g. microfibers, barbs, microneedles, spikes, or the like) arranged so as to intimately interconnect the patch to the patient during a monitoring session. Such a configuration may be advantageous for reducing and/or eliminating the need for an adhesive layer in such a patch configuration.

In aspects, an electrode including one or more features in accordance with the present disclosure may be dimensioned with an area of less than 4 centimeter $(cm)^2$, less than 1 $cm^2$, less than 0.5 $cm^2$, less than 0.25 $cm^2$, or the like for monitoring a macro signal such as is related to an EKG, an EEG, a surface EMG, etc. One or more of the electrodes (or one or more microneedle electrode features) may be dimensioned with an exposed electrode area of less than 1000 $um^2$, less than 200 um², less than 100 um², less than 50 um², less than 5 um², or the like, in the case of the microneedle electrode features optionally exposed at the tip thereof, so as to measure one or more micro-electrophysiological signals, a multi-unit nerve study, or the like. In aspects, a plurality of microneedle electrode elements may be electrically isolated from the others such that a plurality of micro electrophysiological measurements may be made therefrom. In aspects, the array may be coupled with a plurality of preamplifiers, multiplexers, analog to digital converters, comparators, or the like, so as to collectively capture micro-electrophysiological signals therefrom. In aspects, such a configuration may be advantageous for monitoring neural traffic at the surface of the skin, measuring skin sympathetic neural activity, ocular nerve activity, touch analysis, etc.

In aspects, the microneedles may be configured for providing a stimulating current into the adjacent tissues, the patch and/or module including one or more pulse generators configured to provide the stimulating current. Such a configuration may be advantageous for providing an easy to apply acupuncture system for treating a subject.

In aspects, a system in accordance with the present disclosure may include one or more patches for attachment to a subject at alternative, seemingly arbitrary locations. The patches may be attached over the body of the subject to investigate physiologic parameters related to specific regions of the body, to determine blood flow propagation, electric field propagation, local muscle response, etc. as discussed throughout the present disclosure.

In aspects, one or more sensors may be formed from one or more organic electronic elements, patterned versions thereof, semiconducting versions thereof, etc.

In aspects, other methods for rendering the skin conductive and/or for generating conductive portals on the body include subdermally implantable studs, infusions of conducting materials, infusion of hyaluronic acid and optional in situ gelation thereof in the tissues, in situ polymerization of an intrinsically conducting polymer, application of electroporation (e.g. optionally via a patch/module pair, a handheld device, etc.), abrasion, or the like.

In aspects, a wide range of functions for microcircuits in accordance with the present disclosure are envisaged, including storing identification information, configuring an inductive interface (i.e. with an antenna embedded into a patch) to provide inductive coupling of one or more patch elements to a corresponding module, etc. In aspects, one or more microcircuit may be embedded into a patch in accordance with the present disclosure, embedded into the housing of a module, etc.

In aspects, a microstud in accordance with the present disclosure may be configured to form an interconnect between a patch and a mating structure on a module as well as to provide a medium for conducting electricity between the patch and the module during use.

In aspects, a patch and/or module in accordance with the present disclosure may include means for biasing a sensor included therein towards the subject so as to maintain more intimate contact between the sensor and the subject during a monitoring session.

In aspects, a system in accordance with the present disclosure may include an isolating patch for interfacing a handheld unit monitoring device with a subject. In aspects, the isolating patch may include one or more subject side electrodes and one or more device side electrodes. Each subject side electrode coupled to one or more of the device side electrodes so as to provide a means for communicating between the skin of the subject and the handheld unit (i.e. without the handheld unit coming into direct contact with the subject). Such an isolating patch may be advantageous for interfacing a handheld EKG monitoring apparatus (e.g. a hand held unit with contact electrodes, an AliveCor™ module, etc.).

In aspects, such an isolating patch may include a z-axis conducting adhesive, formed so as to provide a conductive medium through the thickness of the isolating patch without allowing for transfer of biological species there between.

In aspects, the z-axis conductive adhesive may be patterned such that an operator of the handheld unit may observe one or more visual cues when aligning the handheld unit with the isolating patch in order to interface with the subject.

In aspects, a patch in accordance with the present disclosure may be configured and dimensioned for attachment to the bridge of a subject's nose (i.e a nasal patch configuration). Such a nasal patch may include an optical sensor and optionally a light source each in accordance with the present disclosure. The optical sensor may be configured to capture light from an adjacent skin surface (i.e. nasal tissues) for purposes of measuring local blood flow, a heart-rate, etc. therefrom. In aspects, the nasal patch may include a flexing member (e.g. a stiffened polymer element, etc.) optionally integrated into, or representing the substrate, the flexing member configured so as to pull upon the sides of the nose after placement, so as to improve airflow there through. Such a configuration may be advantageous for monitoring a subject during exercise while improving performance of the subject (i.e. via improving breathe exchange).

In aspects, the optical sensor may be arranged so as to capture blood flow readings off of the septum, tissue near the nose (philtrum, at the anterior nares), or along an intranasal wall (vestibule, alar of the nose, alar lobule, etc.). The patch may include the optical sensor coupled with a microcircuit in accordance with the present disclosure into a septum clip, an alar clip (e.g. for placement along the outside or inside of the nose, etc.)

In aspects, the optical sensor may be configured to measure sPO2, or a signal related thereto near to a line of contact between the nose and the cheek or alternatively at the root of the nose (near the bridge of the nose). In aspects, the flexing member may be configured so as to bias the sensor towards the tissue during a monitoring session. The sensor may be biased towards the tissues with a pressure of greater than 5 mmHg, greater than 15 mmHg, greater than 40 mmHg, etc. In aspects, the sensor may be biased towards the tissue with a pressure of approximately 5 mmHg, approximately 10 mmHg, approximately 25 mmHg, approximately 35 mmHg, or the like.

Module Features and Performance Enhancing Aspects

A system in accordance with the present disclosure may include one or more modules each in accordance with the present disclosure. The modules may be configured to interface with a patch in accordance with the present disclosure. In aspects, a module may include a power source, a housing, one or more interconnects, signal conditioning circuitry, communication circuitry, a processor, a transceiver, a transducer, one or more sensors, an antenna, a buzzer, a button, a light source, and/or the like, configured to generate one or more signals (e.g. physiologic, electrophysiologic, and/or physical signals) or a feedback signal in accordance with the present disclosure. The signal conditioning circuitry may be configured to amplify, de-noise, pre-filter, generate a trigger, analyze aspects, extract a metric, etc. from one or more physiologic and/or physical signals during a monitoring session, a calibration session, an attachment event, etc.

In aspects, one or more interconnects may be configured for electrically conducting interconnection, inductively coupled interconnection, capacitively coupled interconnection, between the module and a corresponding patch. In the case of an electrically conducting interconnect, each patch and module interconnect may include complimentary electrically conducting connectors, configured and dimensioned so as to conduct current there between upon attachment.

In aspects, the module may include a housing, the housing including one or more aspects of the interconnect, optionally providing a sealed cavity in which other components of the module may reside. One or more of the circuits may be integrated into the housing. In aspects, the interconnect may be integrated into one or more circuits included in the housing. The antenna may be integrated into the housing (e.g. printed onto the housing, embedded into the housing, sealed within the housing, etc.).

In aspects, an interconnect in accordance with the present disclosure may be embedded into one or more of the circuits. The interconnect may be at least partially formed from a through-hole within the circuit (i.e. formed in conjunction with a through hole interconnect on a circuit board of the module). The interconnect may include a cap configured as a surface mount component to form a hermetic seal around the interconnect itself (i.e. so as to isolate the interior of the module from the interconnect).

In aspects, an interconnect, circuit, circuit board, high density interconnect (HDI) board, or the like may include a magnetic. In aspects, the magnet may be embedded into a circuit of the module (e.g. embedded into a region, attached to, or embedded into a through-hole of the circuit). Such a configuration may be advantageous to simplify assembly of the module and reduce the form factor taken up by the interconnects within the module.

In aspects, an interconnect and/or circuit board including a magnet may be configured such that the magnet forms the electrical connection to the patch as well as maintains a bias force between the module and the patch during the attachment period.

In aspects, the module may include one or more sensors each in accordance with the present disclosure. A system in accordance with the present disclosure may include a plurality of module types (i.e. modules with differing sensing aspects). In one non-limiting example, the system includes a kinetic module including an accelerometer, a gyroscope, and/or a magnetometer, a thermal module including one or more temperature sensors, an airflow sensor, and/or a moisture sensor, and an optical module including an optical sensor configured to monitor one or more optical parameter in an associated patch or skin surface. Such module functionality may be included in addition to the communication and power aspects provided to interface with a corresponding patch (which may include one or more sensors, electrodes, etc.).

In aspects, the interconnect may include one or more snap connectors (i.e. so as to interface with a corresponding microstud based patch, etc.).

In aspects, one or more modules in accordance with the present disclosure may include one or more sensors and/or microcircuitry configured to interface with the sensor(s), the sensors configured to monitor one or more physiologic, environmental, and/or physical parameters locally on the subject. Some non-limiting examples of such sensors include electrophysiologic sensors (e.g. EKG, EMG, EEG, ERG, EOG, respiration, bioimpedance, activity, etc.), temperature sensor (e.g. near to the skin, within a module, ambient [environmental], etc.), thermal gradient sensor (e.g. so as to calculate a heat transfer vector locally on the body of the subject, to estimate a core temperature, etc.), barometer, altimeter, accelerometer, gyroscope, humidity sensor, magnetometer, inclinometer, oximeter, colorimetric monitor (e.g. color change analysis of underlying tissue, for respiration, blood flow, pulse, etc.), sweat analyte sensor (e.g. so as to measure sweat constituents, salt content, etc.), galvanic skin response, neural activity (e.g. skin sympathetic activity), interfacial pressure sensors (e.g. for contact assessment, compliance measurement, blood pressure, etc.), flow sensor (e.g. airflow over a module, etc.), surface strain sensor (e.g. via integration of stretch sensors into the patch, evaluation of stretch along one or more electrical interconnect within the patch, integrated capacitive stretch sensors, etc.), a microphone, combinations thereof, and the like.

In aspects, a module in accordance with the present disclosure may include a three dimensional antenna. The antenna may be arranged along, or embedded within a wall of the module housing (e.g. printed along the wall of the housing, embedded within the outer wall of the housing, particularly in a dome shaped, or pseudo hemi-spherically shaped module, etc.). In aspects, the antenna may be formed from a freestanding conducting structure, suspended above a ground plane situated within the module (e.g. incorporated into a circuit thereof), etc. Such a configuration may be advantageous for boosting a communication range, providing more reliable wireless connections, or the like in the context of monitoring physiologic signals on a subject. Such a configuration may be advantageous for reducing power consumption during wireless communications performed therewith.

In aspects, the three dimensional antenna may be printed along the inner wall of a suitable shaped housing (i.e. a pseudo hemispherical housing) with one or more pickups arranged along the base thereof. A module in accordance with the present disclosure may include a circuit configured and dimensioned so as to form a wall of the housing, including one or more electrical connections configured to interface with the pickups during assembly. Such a configuration may be advantageous for providing an improved wireless performance while minimizing the form factor thereof.

The module may include one or more lights, buttons, buzzers, etc. in order to interact with a user (e.g. a subject, a practitioner, a caregiver, etc.).

In aspects, a module may include a three dimensional circuit, a stacked circuit, or the like. One or more of the circuit elements may be interconnected with a high density interconnect (HDI) printed circuit board, the HDI printed circuit board optionally configured to function as part of the housing of a module in accordance with the present disclosure.

In aspects, one or more elements within the module may be encapsulated in a potting material to provide a hermetically sealed element, etc.

In aspects, a module in accordance with the present disclosure may include a power source (e.g. a battery, a rechargeable battery, an energy harvesting system, etc.). As such, each module may be a self-powered device. In aspects, a module may include a processor and an internal power source.

The microcircuit may include one or more of signal conditioning circuitry, a system on chip, a processor, a radio, a power management system, an energy harvesting system, a memory module, etc.

In aspects, the processor may be programmed to operate in a range of power states (e.g. a low power state, a diagnostic state, a monitoring state, a subject detected state, a synchronization state, a calibration state, a communicating state, a recharging state, an alert state, a troubleshooting state, etc.). The processor may operably remain in a low power state so as to improve the lifetime of the power source. The processor may switch between states based on conditions determined via the sensors, a recharge unit, a calibration unit, a host device, etc.

Each module may be configured to communicate with one or more patches, additional modules, an analysis device, and/or a host device, etc. Such communication may be performed wirelessly (e.g. acoustically, via infrared, via radio frequency communication, etc.) through the environment surrounding the subject, through the body of the subject (e.g. acoustically, optically, capacitively, resistively, and/or inductively coupled signal transmission, etc.). In aspects, one or more patches may relay a combination of an energy signal (e.g. to determine a physiologic parameter) as well as to communicate an information signal to one or more patches, modules, a host device, etc.

The processor may be programmed and configured via connection with one or more sensors to determine when a module and/or patch/module pair has been placed onto a subject. The processor via data collected from one or more sensors may be configured to determine the quality of the interface with the subject. In aspects, the patch may include two or more electrode elements to be placed into electrical contact with the subject during a monitoring session. The processor may, via the electrode elements and/or signal conditioning or test electronics attached thereto, estimate the impedance between the electrodes and the body of the subject. If the impedance levels are within acceptable ranges, the processor may initiate collection of bioelectrical information from the subject during a monitoring session. If impedance levels are deemed outside acceptable ranges, the processor may opt not to monitor the subject during the monitoring session. In this case, the module may communicate a "bad connection" signal to one or more modules, patches, an analysis device and/or a host device during a monitoring session. The module may alternatively or in combination send a compromised signal, one or more modules, patches, an analysis device and/or a host device may be used to determine as much information as possible from the signal (e.g. in relation to an EKG example, the signal measured may not be of diagnostic quality, yet detection of the QRS pulse may be adequate for timing blood flow events between patches, determining heart-rate, etc.). As such, analysis of degraded signals may be advantageous for completing a monitoring session with at least a minimum quantity of viable signal information.

In aspects, the module may include a microcircuit configured to periodically monitor an interconnect to the patch so as to determine if the module has been attached to a corresponding patch or not. Upon identification of attachment to the patch, the microcircuit may perform a wakeup function, a test function, a network communication function, etc. Such detection may be advantageous for hot swapping of monitoring units on a subject to ensure substantially continuous and/or continuous monitoring thereof during a usage scenario.

In aspects, a module in accordance with the present disclosure may be formed as a watertight and sterilizable component so as to be reused across multiple subjects (e.g. washed and/or sterilized and used across multiple patients, multiple gym members, multiple students, etc.). In such usage cases, the module may be hermetically sealed, such that fluid ingress into the module is limited. In aspects, the module may be filled with a low dielectric permittivity potting material, so as to limit the potential for fluid ingress during use.

In aspects, one or more of the patch and/or the module may include registration and/or alignment features to assist a user (e.g. the subject, a physician, a trainer, a caregiver, an emergency medical technician, etc.), with rapidly and/or reliably attaching a module to a patch to initiate a monitoring procedure (or to swap out a module during a monitoring procedure, etc.). Such registration marks and/or alignment features may be utilized by one or more multi-patch coordinating algorithms in accordance with the present disclosure (e.g. so as to assist with more accurately/precisely identifying module/patch placement on the body, identifying particular patches and modules on the subject, for identification and/or orientation purposes if cataloging placement/orientation or determining placement/orientation of modules, via photograph, etc.).

One or more modules may include electronics and/or software algorithms for detecting one or more fault conditions related to contact with the body of the subject. In aspects, the module may be configured to detect when the impedance between an electrode and the subject is within an acceptable range for measurements (e.g. less than 2 Mohm, less than 200 kohm, less than 20 kohm, less than 2 kohm, or the like). In aspects, the electronics may be configured to glean such information by measuring or estimating the impedance between two or more electrode pickups on a coupled patch. In aspects, an impedance estimate may be determined by applying a brief voltage or current pulse to a first electrode, applying a load to a second electrode, and monitoring the temporal response of the second electrode against the first. The rise time of the temporal response compared against the load may be used to indicate the collective impedance of the electrodes and tissues there between.

In aspects, one or more modules may include a signal source for imparting an energy signal (e.g. electrostatic, electromagnetic, magnetic, vibrational, thermal, optical, etc.) into the body of the subject. The energy signal may be used to communicate to the user, as a form of alert, for diagnostic purposes, to determine a physiologic and/or physical parameter, to configure an array of patches, provide sensation to the subject, etc. In aspects, the energy signal may be emitted into the body of the subject by a first patch and simultaneously monitored by one or more patches to determine a physiologic parameter of the subject, location based calibration of the patches on the body, etc. In aspects, an identification signal may be merged with the energy signal in order to identify the patch from which the signal was emitted (e.g. so as to automatically configure a patch network, to determine the health of the patch network, to determine a location parameter of a patch with respect to other patches on the body, etc.).

In aspects, one or more modules and/or patches may include an optical sensor for measuring colorimetric changes in the adjacent tissues during the monitoring process. Such information may be used, optionally in combination with an energy signal to determine one or more optically variable physical parameters and/or one or more optically variable physiologic parameters of the subject, local to the associated patch. In aspects, the optical sensor may be used in combination with one or more optical emitters (e.g. light emitting diodes, laser diodes, bulbs, etc.) to monitor a physiologic signal related to local blood perfusion on the body of the subject. A plurality of such patches may simultaneously monitor such physiologic signals at discrete locations on the body of the subject and relay such information to one or more patches, modules, a host device, and/or an analysis device. The combination of information from such patches or modules may be used to determine blood flow dynamics throughout one or more regions of the body of the subject, to characterize the underlying vasculature in one or more regions of the body of the subject, etc. In aspects, blood perfusion related signals are simultaneously measured at multiple locations on the body of the subject (e.g. the chest, arm[s], leg[s]) and the phase and/or time delays between such signals, as well as the shapes and characteristics of the signals may be used to determine an arterial brachial index of the subject. Such techniques may also be used to determine one or more regions of the subject that may suffer from arterial or venous insufficiency. In aspects, such techniques may be used to estimate the location and/or presence of a blood clot in an extremity of the subject.

In aspects, one or more modules may include a barometer and/or an altimeter to measure a local environmental parameter (e.g. local pressure, temperature, etc.) during a monitoring session. In aspects, such information may be used to determine the posture of the subject, determine if the subject has fallen, etc. In aspects, the posture of the subject may be used to determine and/or improve such physiologic measurements as those relating to blood pressure of the subject, correcting EKG data, determining positional relationships between a plurality of patches positioned on the body of the subject, etc.

In aspects, one or more modules may include an activity sensor (e.g. an accelerometer, a gyroscope, a pedometer, etc.) to measure one or more inertial parameter (e.g. local acceleration, rotation, vibration, etc.) at a location on the body of the subject during a monitoring session. In aspects, information obtained from one or more activity sensors may be used to remove movement artifacts from a physiologic signal, calculate a trajectory, determine a gravitational reference frame, orientation of the module and/or accompanying patch, etc. In aspects, one or more modules may include a tri-axis accelerometer for characterizing the local inertial vector of the body of the subject to which the module is attached. In aspects, one or more modules may include a tri-axis accelerometer, a gyroscope, and optionally a magnetometer. Information from one or more such sensors may be used to calculate an improved local trajectory of the body part of the subject during a monitoring session.

In aspects, an optical sensor housed within a patch or module may be tailored to monitor a blood flow parameter. In aspects, the optical sensor may be used to monitor a real-time blood perfusion parameter in a tissue of the subject, in the immediate vicinity of the optical sensor. The blood pressure measurement device may include a plurality of such sensors, each sensor configured to monitor a local blood perfusion parameter in the tissue of the subject. Such information may be collected from each sensor in real-time. Correlation of delays, waveform changes, and the like over the body of the subject may be used to generate a correlated signal. In aspects, the correlated signal may be used to create a diagnostic signal (e.g. blood flow volume, blood ejection rate, peripheral vascular parameter, blood oxygen saturation, blood oxygen partial pressure, blood carbon dioxide partial pressure, blood pressure, etc.).

In aspects, a barometer and/or altimeter housed within a module may be configured with an absolute pressure sensor and optionally a temperature sensor. The altimeter may be sufficiently sensitive to determine local changes in altitude, preferably in the range of decimeters, centimeters, millimeters, etc. The blood pressure measurement device may include a plurality of modules and corresponding patches, one or more modules including a barometer and/or altimeter, the differences between which may be used to algorithmically coordinate the location of each patch for further measurement analysis. In aspects, information from each altimeter may be used to determine the vertical distance between altimeters on the subject. Such information may be used to determine the posture of the subject, the heart location relative to the sensors, etc.

In aspects, a module in accordance with the present disclosure may include a recharging connector (or series of contacts), a wireless recharging antenna, or the like for communicating with a recharging bay in accordance with the present disclosure. The recharging connector or antenna may be used to communicate with the recharging bay for purposes of recharging a power source on the module, applying firmware updates, performing diagnostics, or the like.

Algorithm Aspects

A method for monitoring one or more physiologic and/or physical signals from the body of a subject in accordance with the present disclosure includes applying one or more patches each in accordance with the present disclosure to the body of the subject, and attaching a corresponding number of modules each in accordance with the present disclosure to the patches (i.e. so as to form one or more patch/module pairs in accordance with the present disclosure), establishing a body area network among the modules, and collecting physiologic and/or physical signals from the subject using the patches and modules during a monitoring session (i.e. for a period of time suitable for the desired purpose of the method, e.g. 10 seconds, 1 minute (min), 1 hr, 8 hrs, 24 hrs, 1 week, 1 month, 3 months, chronically, etc.).

In aspects, the method may include storing the collected signals on a memory device (e.g. a memory location on the patches, the modules, a host device, a user device, a datacenter, etc.). In aspects, the body area network may be extended to include a host device in accordance with the present disclosure. The method may include transferring the signals and/or one or more signals and/or metrics derived therefrom from the patches and/or modules to the host device, in real-time, intermittently, in a time synchronous fashion, or the like, during and/or after the monitoring session. In a range of applications, the system may be configured to monitor for an event (e.g. a change in heart function, a change in EMG, a change in posture, an impact, a change in breathing rate, etc.).

In aspects, there may be applications where real-time or even pseudo real-time data collection is not necessary (i.e. during aspects of a home sleep study, etc.). In such scenarios, a module in accordance with the present disclosure may be configured to store the collected data locally on a memory device. The module may be configured to download the data to a recharging bay in accordance with the present disclosure at the conclusion of the monitoring session, periodically throughout the monitoring session, or the like in order to transfer the data to a processor for analysis, review, etc.

In aspects, a method for interacting with a subject with one or more patch/module pairs in accordance with the present disclosure may include measuring one or more physiologic signals therefrom. The method may include deriving a feedback signal, a command, an alert, a metric, a diagnostic value, a schedule, an augmented reality overlay, etc. from one or more of the signals. The method may include identifying when one of the modules requires attention (e.g. the battery is low, a poor interconnection has been made with a corresponding patch, or between a corresponding patch and the subject, a malfunction has occurred, a poor signal quality is being obtained therefrom, etc.). Attention may include swapping the module with a new module, swapping the module out without interrupting the monitoring procedure, removing the module and corresponding patch from the subject, etc.

In aspects, the method may include providing feedback to a user (e.g. the subject, a physician, a therapist, an officer, a soldier, a group leader, a teacher, a student, an emergency medical technician (EMT), a coach, a trainer, a partner, etc.) relating to the physiologic and/or physical signals. The method may include representing a signal, value, metric, graphic, etc. related to the signals on a feedback component in accordance with the present disclosure (e.g. on a display, a HUD, a wristwatch, an earpiece, a loudspeaker, a tactile display, etc.).

In aspects, the method may include coordinating the monitoring session across multiple subjects, and optionally synchronizing data collection across the subjects for purposes of calibration, comparative analysis, etc.

In aspects, a method for identifying a patch/module pair participating in a body area network (BAN) on a subject in accordance with the present disclosure includes placing an object (e.g. a hand, a phone, etc.), over a patch/module pair on the subject while listening to the wireless signal strength of all patches within range, and identifying the patch/module pair by a change in the wireless signal strength measured at a receiving hub (e.g. the phone, a hub, one or more modules, etc.), witnessed during the placing process. Such a configuration may be advantageous for establishing a communication link (i.e. pairing) one or more patch/module pairs on a subject with a host device within an environment with a large number of wireless devices or significant wireless signal clutter (e.g. a gym, a spin class, a conference, an airport, etc.).

In aspects, one or more steps in the method may be included as part of a BAN initiation routine, to identify placement of one or more modules on a subject, etc. The method may include prompting a user to place a hand over each module in order to identify it on the subject. The method may include prompting the subject with an image, showing where to place the patch/module pairs. In aspects, the method may include assessing the accuracy of the placement of a patch on the subject (e.g. by assessing the physiologic signal obtained therefrom, comparing such readings against a reference, prompting the subject to perform a test routine such as moving an arm, transitioning the subject from a sitting to a standing position, etc.).

In aspects, a method for identifying a patch/module pair on a subject in accordance with the present disclosure irrespective of the number of patches placed in the vicinity thereof may include, applying one or more patches to the subject (e.g. in a predetermined pattern, substantially random pattern, etc.). Once the system is in communication with and optionally sending data to a host device (e.g. via a wireless link), the host device or a feedback component may prompt the user (e.g. the subject, the care giver, the nurse, the physician, etc.) to place a hand over a patch, a preselected patch, the patch generally nearest to the heart. Upon placement of the hand over the patch, the RF signal power strengths from the patch in question may change appreciably compared with other RF signal power strengths within communication range and thus a positive identification (ID) can be attained without additional hardware requirements.

Such a method may be adapted for simplifying the pairing process between a host device (e.g. a smartphone, a wireless local area network (WLAN), etc.), and one or more patches arranged on the subject. In one non-limiting example, such a method may be used to determine which module a user's hand is placed over during a pairing procedure (e.g. perhaps within range of 100s of other wireless devices, modules, etc.). Such a method may be advantageous for use within a gym setting, a fitness class setting, etc.

In aspects, a system may, at least roughly, determine the general location of one or more patch/module pairs with respect to a host device, by assessing the RF signal strength as received by the host device from one or more of the patch/module pairs in comparison with those received from the other patches in the system.

In aspects, a modular physiologic monitoring system in accordance with the present disclosure may include a plurality of patches (e.g. patches, patch/module pairs, etc.). In a method of monitoring a subject with such a system, the positioning of the patch/module pairs onto a subject may be visually assessed during placement. One or more patches, modules, or both may include an orientation marker and/or an identifying marker that may be visually assessed from a local observer after placement on the body of the subject. In aspects, the precise placement of the patch/module pairs on the subject may be calculated post attachment by taking an image of the subject after the patches have been placed on the subject. The image may be taken with a coordination device (e.g. a smartphone, a camera, a Kinect™ camera, a HUD ready pair of glasses, Google Glass™, etc.), a host device, etc. In aspects, the orientation markers may be segmented, identified, and extracted from the images to calculate one or more calibration parameters from the orientation of the patches over the body of the subject. In aspects, one or more features associated with the subject (e.g. neck, shoulders, arms, legs, torso, etc.) may be detected and categorized, so as to be incorporated into a patch placement calculation or assessment algorithm.

In aspects, the coordination device may be used by a user (e.g. the subject, a practitioner, a clinician, a trainer, a coach, a friend, etc.) to take an image of the subject or a portion thereof after placement of the patches. Patch locations and orientations on the subject (e.g. position vectors, positions with respect to anatomical features on the subject, etc.) may be calculated from the image and used to produce a corrected or standard EKG output, calibrate an EMG based physiotherapy assessment system, automatically assign muscular group behavior to corresponding patches, etc. The system, the host device, the coordination device, etc. may alert a user as to the adverse placement of a patch, the need for more patches, etc. in order to determine a particular cardiovascular function. In aspects, the user may be directed to place one or more additional patches and/or adjust the position of an already placed patch in order to favorably adjust the physiologic data obtained therefrom.

In aspects, the coordination device may also be used to direct the user to properly place patches on the subject dependent upon the goal of the particular monitoring session. In aspects, an augmented reality display may be employed to direct a clinician to properly place electrodes on the body given the goal of the particular monitoring session (e.g. to assist with placement for EKG, EMG, to match placements from previous sessions, etc.). The augmented reality display may overlay orientation markings onto a camera generated display, highlighting where on the subject the user should place one or more patches in order to better achieve the goals of the indicated monitoring session.

In aspects, a method for removing a physiologic monitoring system in accordance with the present disclosure may include spraying or wiping an adhesive removing solution onto one or more of the patches, waiting for the adhesive in the patches to disengage from the subject and to remove the patches.

In aspects, a method in accordance with the present disclosure may include generating one or more metrics from a captured signal (e.g. within a patch, a module, or a patch/module pair in accordance with the present disclosure), prior to wirelessly sending information to another entity in an associated BAN.

In aspects, data transfer from a module may occur only when a valid physiologic and/or physical signal has been captured from the subject. A module and/or processor coupled thereto may include a function configured to analyze the captured signal in order to determine if a valid reading has been obtained (e.g. such as via detection of a heart-beat, via validation of such signals with those obtained from one or more alternative patches in the system, via detection of substantial movement artifacts, via detection of a low quality electrical interface with the body).

In aspects, a module in accordance with the present disclosure may include one or more algorithms (e.g. implemented on a processor, SoC, etc.) configured to analyze the signals obtained from the subject. In aspects, an algorithm in accordance with the present disclosure may be configured to extract a metric from the signal including a heart-beat, time-stamping of a QRS complex, etc. (or other metrics as described herein). In aspects, to save on wireless bandwidth and associated power consumption, a module may include an algorithm to efficiently extract such metrics from the raw data and send the metrics rather than the raw data. In aspects, the modules may include multiple modes of operation (e.g. a low priority mode, a high priority mode). Some modes may be configured so as to send small amounts of data (i.e. such as when a heart-rate or monitored function of a subject is within a 'normal' range), or metrics extracted from the raw data (e.g. a simple heart-rate, etc.) so as to maintain a low wireless bandwidth. Some modes may be configured so as to send all available data (i.e. such as when an 'event' is occurring, when a previously 'normal' signal changes) so as to provide a user with as much information as possible during the 'event'. Such a configuration may be advantageous to balance power consumption of hardware within the modules with the depth of the monitored signal.

In aspects, when configured for monitoring of an electrocardiographic signal, a module may be configured to adjust the sampling rate thereof with an adaptive sampling algorithm (e.g. a local adaptive sampling algorithm, etc.). In aspects, an adaptive sampling algorithm may be constructed to use a timestamp associated with the QRS complex. In aspects, the sampling algorithm may be configured to increase sampling rate to just beyond the frequency determined by the Nyquist-Shannon sampling theorem for the given heart-rate of the subject (i.e. adjustable with heart-rate), and the other samples obtained within a single heart-beat, may be taken at a much lower rate (i.e. as the signal generally does not include the same high frequency content in those regions of the beat). Such a configuration may be advantageous to reduce power consumption within a module, decrease the amount of data sent wirelessly from the module, etc.

In aspects, the BAN may implicitly extend to a recognized user device (e.g. a HUD ready pair of glasses worn by a user, a coach's wrist watch, etc.) when that entity enters the range of the BAN. Thus one or more signals, metrics, identification records, etc. relating to the subject or monitoring session may automatically start streaming to the user device upon recognition. In aspects, such a configuration may be advantageous for seamlessly brining new users into a monitoring session without requiring extensive effort on the part of the user.

In aspects, a method in accordance with the present disclosure may include determining a priority metric for one or more signals captured by a module in the system (e.g. via assigning a priority level, determining a degree of redundancy, etc.). Such a priority metric may be used in an algorithm to determine the type and urgency of an "alert" generated by a failure on one or more modules in the system. In one non-limiting example, a system including 5 modules is deployed onto a subject to monitor a 3 lead equivalent EKG in accordance with the present disclosure. A priority metric for the system is determined based on the number of modules that would have to fail in order to risk obtaining a low quality EKG from the subject. In aspects, the priority may be more or less affected by the removal of one or more modules in the system (i.e. based upon the location of the module on the subject), etc. If a module on the subject fails or indicates that it is about to fail (i.e. a battery low alert). The system may be configured to assess how such a failure will affect the priority metric, thus adjusting a potential alert accordingly (i.e. from "do nothing" through to "needs immediate attention"). Such a configuration may be advantageous for reducing false alarms within a hospital setting, thus reducing alarm fatigue, or the like while providing more robust monitoring of EKG.

A method for managing a monitoring session with a system in accordance with the present disclosure may include, mounting one or more modules on a recharge bay. Diagnosing function of and/or recharging one or more modules with the recharge bay. Indicating to a user when a module in the recharge bay is ready for use. Swapping a module from the body to the recharge bay and vice versa. Integrating a newly placed module into the BAN and initiating the streaming of signals therefrom.

In aspects, a method in accordance with the present disclosure may include generating a local field vector from a patch/module pair including three or more electrodes. The method may include calculating a vector electrocardiogram from a collection of local field vectors, or the like. The method may include displaying one or more field vectors over an image of the subject to assist with the assessment thereof.

Aesthetic Design Aspects

In aspects, the patch may be shaped so as to contour a specific region of the body so as to better capture signals there from during a monitoring session. In aspects, the modules may be designed so as to maintain a low profile and with no sharp edges, etc. in order to better hide the modules and/or reduce snags during a procedure.

In aspects, the modules may be formed as hemispheres or pseudo hemispheres for purposes disclosed herein. In aspects, the modules may include one or more low profile interconnects arranged along an underside thereof, to interface with a corresponding patch for purposes of monitoring.

The modules may include one or more orientation markings to assist with alignment of the modules onto one or more patches on the body, automatically determine orientation and positioning of the modules one the subject (e.g. with a camera, a video system, etc.).

Monitoring Kit Aspects

A system in accordance with the present disclosure may be provided as part of a monitoring kit. In aspects, a monitoring kit in accordance with the present disclosure may include one or more modules, a recharging bay, one or more patches, or set of patches (i.e. a series of patches configured and dimensioned to perform a particular type of monitoring on a subject), and (optionally) one or more accessories such as an adhesive removal wipe/spray, skin preparation tools, instructions, software access, etc.

In aspects, the recharging bay may be configured to hold one or more modules each in accordance with the present disclosure. The recharging bay may be configured so as to act as a host device (e.g. as a wireless hub, etc.) so as to provide multiple functions for a user.

The recharging bay may include one or more connectors to interface with each module. The connectors may be configured to provide recharging services for the modules, to interface with a processor on the module, to transfer data (e.g. stored session data, etc.), to perform firmware updates, to assess functionality of the module (i.e. to test interconnects of the module, onboard circuitry, etc.). The recharging bay may include one or more status or diagnostic indicators there upon, to identify if a held module is ready for use, recharging, if there is an error with the module, etc.

The recharging bay may be configured for mounting to a wall, such as near to the bed of a subject, etc. so as to facilitate simplified hot swapping of modules to the subject, etc.

The recharging bay may be configured to interface with a host device, a user device, etc. for purposes of monitoring the subject, and/or providing alerts, assisting with configuration of a system in accordance with the present disclosure, etc.

In aspects, the kit may include a patch set configured for providing specific functionality on a subject, or sized to fit the subject (e.g. small, medium, large, custom, etc.). In aspects, the patch set may be configured to perform a 3 lead EKG, a redundant 12 lead EKG, a biomechanic assessment (e.g. for a leg, a hand, an arm, a foot, etc.), a sleep lab assessment, an impact study, a sport specific application, a heart-rate monitoring session, a thermal overload monitoring session (e.g. for monitoring for heat exhaustion, etc.), a weight lifting workout, etc.

In aspects, there is provided, an adhesive test kit for determining preferences of a user prior to performing a monitoring session in accordance with the present disclosure. The adhesive test kit may include a series of patches, each patch with identification markings and an associated adhesive (i.e. each with an alternative type of adhesive). The adhesive test kit may be provided to a perspective customer, so as to choose the adhesive type that best suits their needs (e.g. the adhesive with the best long-term wear ability for their skin type, for their diet, adhesive with the lowest irritation for that person, etc.).

In aspects, the adhesive test kit may include a plurality of test patches with a range of adhesive options for potential customers to test during a workout, in a shower, during rest, etc. in order to determine which best suits their needs, best limit skin irritation, best adhere to their skin, etc. In aspects, a customer to a service plan in accordance with the present disclosure may receive periodic adhesive test kits to determine if alternative adhesives would better serve their changing needs, etc.

In aspects, one or more adhesive samples in the kit may include polyacrylate, polyisobutylene, polysiloxane, polyurethane, pressure sensitive adhesive, amphiphilic adhesive, polyvinylpyrrolidone (PVP), polyvinyl Alcohol (PVA), polyethylene glycol (PEG), or poly (2-acrylamido-2-methyl propyl sulfonic acid) (PAMPS) based hydrogel adhesives, combinations thereof, or the like.

As part of a service plan, an adhesive test kit may be provided to a customer. The customer may wear the samples provided in the kit for a suitable period of time depending on the intended application, to determine which adhesive is best for them (e.g. most compatible with their skin, wearable, reliable, etc.).

The test patches may be configured with additional weight, etc. to simulate the attachment of a module thereto. One or more test patches may include an impedance monitoring circuit to assess the reliability of a monitoring process provided therewith.

The recharging bay may be integrated into a display (e.g. into the chassis of a signal display system, etc.). Such a display may provide a means for a user to interact with the recharging bay, provide data, metrics, or visualization of the signals, etc. Such a display may be advantageous for use within a hospital setting, as a monitor and/or analyzer in an intensive care unit (ICU), an operating room (OR), etc. with a cluster of modules, patient interfaces and hand-held coordination devices.

Business Method Aspects

According to aspects, there is provided a service (i.e. optionally embodied in the form of a service system) for managing the collection of physiologic data from a customer, including a subscription service in which a customer is assigned a profile including usage related information (e.g. purposes for monitoring, billing, etc.), an automated patch delivery system configured to provide a customer with a timely series of patches for use in one or more associated monitoring sessions, a datacenter configured to store, analyze, etc. the data obtained from the customer during one or more monitoring sessions, a report generating service configured to generate one or more monitoring reports based upon the data obtained during one or more monitoring sessions, and a recurrent billing system configured to bill the customer based upon the number or patches consumed, the data stored, the reports generated, or the like.

The service may include a module replacement system configured to identify from the data when a customer may require additional modules and to include such modules along with a replacement patch set delivery, for immediate delivery, etc. depending on the particular needs of the customer.

The service may include one or more application programming interfaces (APIs) whereby one or more $3^{rd}$ parties (e.g. a data repositories, government agencies, pharmaceutical companies, health data providers, EHRs, a social network, an employer, a healthcare provider, etc.) may access the data, reports generated therefrom, etc.

In aspects, the service may include an automated adhesive selection algorithm configured to assign a customer preference for adhesives in a patch set based upon the outcome of an adhesive test (i.e. performed via an adhesive test kit in accordance with the present disclosure).

In aspects, the service may include an automated algorithm for assessing the performance of a patch set on a customer from the data. Such an algorithm may be configured to identify if a customer is experiencing irregular, erratic, problematic, shortened, wear times, etc. and may issue an alert to contact the customer, issue an alternative adhesive preference, issue for delivery of a complimentary adhesive test kit to the customer, etc.

In aspects, the service may include one or more algorithms for providing remote coaching, stress management, physiotherapy, and/or related services to a customer, hospital, clinic, etc.

General Discussion on Host Devices

In aspects, the host device may be operably worn/held by the subject, located near to the subject, integrated into a bedside alarm clock, or housed in an accessory (e.g. a purse, a backpack, a wallet, etc.). In aspects, the host device may be a mobile computing device (e.g. a smartphone, a tablet computer, a pager, etc.). In aspects, the host device may be a local router, a data recorder, a network hub, a server, a secondary mobile computing device, a router, a repeater, etc.

In aspects, the host device may be a dongle or accessory for a mobile computing device. In such aspects, the host device may be configured to coordinate communication with one or more patches/modules, analyze incoming patch data, fuse sensor information from one or more patches, condition and/or de-noise information signals obtained from one or more patches, correlate connectivity of one or more patches, to reconstruct signals from parameters sent by one or more patches/modules, or the like. In aspects, the host device may be configured to generate one or more physiologic signals, alerts, etc. therefrom.

In aspects, one or more patches, modules, a host device, user device, and/or an analysis device may fuse sensory information from one or more patches during a monitoring session. If sensory information is missing from a particular patch, module, etc. or if it is in some way compromised, etc. the one or more patches, modules, the host device and/or the analysis device may ignore, remove, de-emphasize, etc. the information. As such, the system may be advantageous for providing a robust, fault tolerance means for monitoring one or more physiologic parameters of a subject.

In aspects, one or more patches, modules, a host device, a user device, and/or an analysis device may generate various levels of alerts for maintaining the monitoring session during a long-term monitoring session on a subject. Such alerts may be related to a subject emergency (e.g. a fall, a heart arrhythmia, a neurological arrhythmia [e.g. due to a seizure], an elevated heart-rate, syncope, an accident, an impact, a sleep apnea event, respiratory arrhythmia, choking, a drop in arterial carbon dioxide ($CO_2$), hypercapnia, a missing heart-rate, etc.), a moderate priority maintenance need (e.g. a high number of compromised signals, a high number of low or depleted power sources, etc.), a low priority maintenance need (e.g. a limited number of compromised signals, one or more low battery indications, etc.).

In aspects, one or more patches, modules, a host device and/or an analysis device may generate an "information quality" signal related to the overall quality of one or more signals (e.g. individual information signals, a collective signal, a physiologic parameter, etc.) related to one or more patches on the subject, and/or the overall system. Such an "information quality" signal may be used to determine and/or convey the degree of confidence that the system has in the physiologic parameters of a subject being measured during a monitoring session. The signal may be good, average, compromised, poor, unacceptable and/or the like. An alert may be advantageously constructed from the information quality signal so as to optimally compromise between functionality (e.g. basic quality of the monitoring session) and productivity (e.g. number of alerts requiring attention) during a monitoring session.

A modular physiologic monitoring system in accordance with the present disclosure may include a host device in communication with one or more patches. The host device may coordinate the monitoring network, etc. One or more patches, and/or the host device may be configured in operable electrical communication with each other. In aspects, the patches and/or the host may be configured to communicate with each other during a calibration procedure (e.g. so as to calibrate the altimeters). Such calibration may be advantageous for improving the quality of the monitoring session.

The host device may communicate with an external network (e.g. a WiFi network, a cellular network, a LAN, etc.). In aspects, the host device may be a stationary device wired to a local area network (LAN), configured to communicate one or more signals and/or information derived therefrom to another device, via the LAN.

In aspects, the host device may be configured to monitor the wireless signal strength received from one or more patch/module pairs in an associated BAN and coordinate signal transfer from patch/module pairs to the hub, or between each other, so as to maximize the strength of the BAN+hub network (i.e. in the case that the hub is not situated on the body of the subject). In aspects, the hub may coordinate that a module with a poor signal transfer data to high signal strength module on the subject, and the high signal strength module relay the data to the hub (if the hub communicates that the data was not received, if a signal could not be obtained directly from the module, etc.).

Discussion related specifically to the Figures follows, the discussion above may be applied where ever applicable to a particular Figure reference.

FIGS. 1a-d show aspects of modular physiologic monitoring systems in accordance with the present disclosure. FIG. 1a shows a subject 1 with a series of patches and/or patch/module pairs 5-137 each in accordance with the present disclosure, a host device 145 in accordance with the present disclosure, a feedback/user device 147 in accordance with the present disclosure displaying some data 148 based upon signals obtained from the subject 1, an one or more feedback devices 135, 140, in accordance with the present disclosure configured to convey to the subject one or more aspects of the signals or information gleaned therefrom. The host device 145, the user device 147 the patches and/or patch module pairs 5-137, and/or the feedback devices 135, 140 may be configured for wireless communication 146, 149 during a monitoring session.

In aspects, a patch/module pair may be adapted for placement almost anywhere on the body of a subject 1. As shown in FIG. 1a, some sites may include attachment to the cranium or forehead 131, the temple, the ear or behind the ear 50, the neck, the front, side, or back of the neck 137, a shoulder 105, a chest region with minimal muscle mass 100, integrated into a piece of ornamental jewelry 55 (may be a host, a hub, a feedback device, etc.), arrangement on the torso 110*a-c*, arrangement on the abdomen 80 for monitoring movement or breathing, below the rib cage 90 for monitoring respiration (generally on the right side of the body to substantially reduce EKG influences on the measurements), on a muscle such as a bicep 85, on a wrist 135 or in combination with a wearable computing device 60 on the wrist (e.g. a smart watch, a fitness band, etc.), on a buttocks 25, on a thigh 75, on a calf muscle 70, on a knee 35 particularly for proprioception based studies and impact studies, on a shin 30 primarily for impact studies, on an ankle 65, over an Achilles tendon 20, on the front or top of the foot 15, on a heel 5, or around the bottom of a foot or toes 10. Other sites for placement of such devices are envisioned. Selection of the monitoring sites is generally determined based upon the intended application of the patch/module pairs described herein.

Figure 1B:
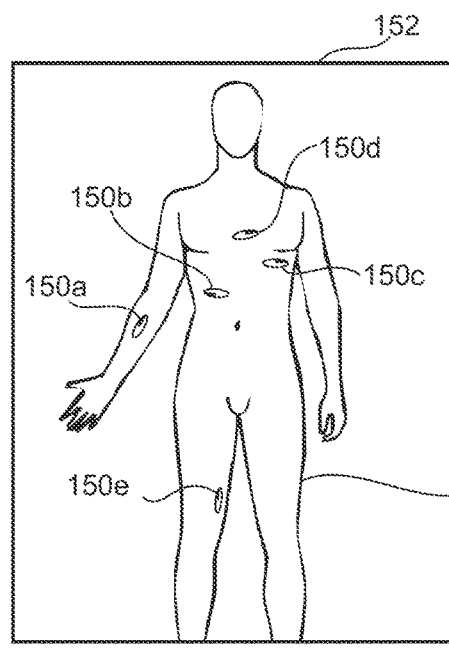

FIG. 1*b* shows a series of patch/module pairs 150*a-e* each in accordance with the present disclosure placed upon a subject 2 as part of a monitoring session in accordance with the present disclosure, in this case an EKG monitoring session. An image 152 of the subject 2 has been taken and may be analyzed in accordance with the present disclosure to calculate one or more standard lead configurations from the arrangement of patch/modules 150*a-e* shown.

Figure 1C:
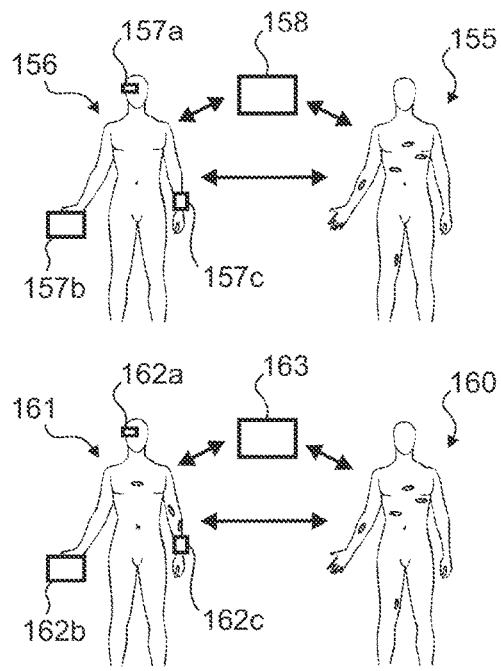

FIG. 1*c* shows aspects of communication between subjects 155, 160 and non-subject users 156, 161 partaking in a monitoring session in accordance with the present disclosure. In a first aspect, the subject 155 is wearing a series of patches and modules each in accordance with the present disclosure configured to communicate with one or more of a host device 158, a display 157*b*, a HUD, a pair of virtual reality goggles, a Google Glasses™ based feedback device 157*a* (i.e. potentially via a smartphone hub), and/or a wristwatch 157*c* to communicate one or more feedback signals in accordance with the present disclosure to the user 156.

In a second aspect, the subject 160 is wearing a series of patches and modules each in accordance with the present disclosure configured to communicate with one or more of a host device 163, a display 162*b*, a virtual reality headset, a HUD, a Google Glasses™ based feedback device 162*a* (i.e. via a smartphone hub), a wristwatch 162*c*, and/or one or more patches and/or modules configured upon the body of the user 161 to communicate one or more feedback signals in accordance with the present disclosure to the user 161 or to convey one or more sensations to the body of the user 161 (i.e. via the attached patches).

In aspects, the communication between the subjects 155, 160 and the users 156, 161 may be bidirectional (i.e. the subject 155, 160 may also receive information corresponding to physiologic and/or physical information obtained from the user 156, 161).

Figure 1D:
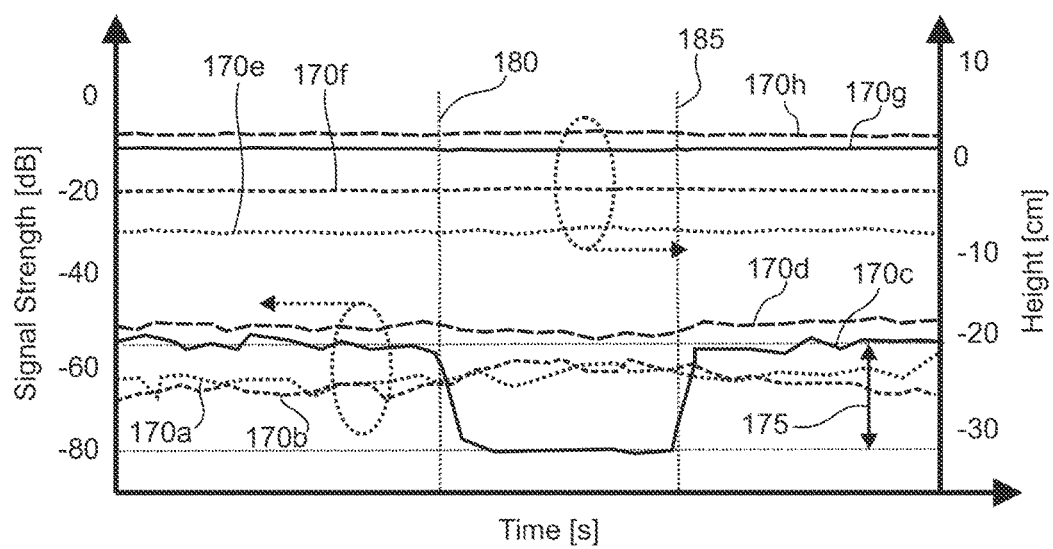

FIG. 1*d* shows a time series example of an identification process for a patch/module pair in accordance with the present disclosure. In the non-limiting example shown, the modules are equipped with radios, each radio capable of sending a signal with a predetermined signal strength (left vertical axis) and equipped with a barometer or altimeter calibrated to give a relative height signal (right vertical axis). In aspects, a user, a program on a feedback device, on a host device, on a user device, etc. may prompt a subject or user to cover a particular patch on the body of the subject (e.g. communicated to the subject or user via an instruction pamphlet, via a screen prompt, etc.). When the prompted module is covered (period between timestamps 180, 185) the signal strength of the module is changed by a substantially identifiable amount 175. Thus a simple procedure may be used to identify a module in the BAN, correlate a module on a particular site on the subject with a corresponding ID received by the host device, etc. Other aspects and variants of a localization and/or orientation procedure are discussed throughout this disclosure.

Figure 2A:
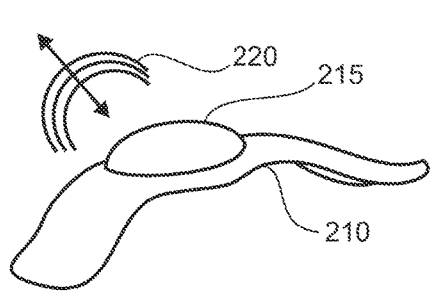
FIGS. 2a-d show aspects of a patch and a corresponding module in accordance with the present disclosure.

FIGS. 2*a-d* show aspects of a patch and a corresponding module in accordance with the present disclosure. FIG. 2*a* shows aspects of a patch 210 in accordance with the present disclosure coupled to a module 215 in accordance with the present disclosure.

The patch 210 may include a substrate formed from a flexible, stretchable material. In aspects, the patch 210 may be stretchy, elastically deformable, or the like. In aspects, once interfaced with a subject, the patch 210 may continue to function (i.e. provide working interfaces between an interconnect provided thereupon and one or more sensors/electrodes provided thereupon) at a stretch of greater than 25%, greater than 50%, greater than 80%, etc.

Figure 2B:
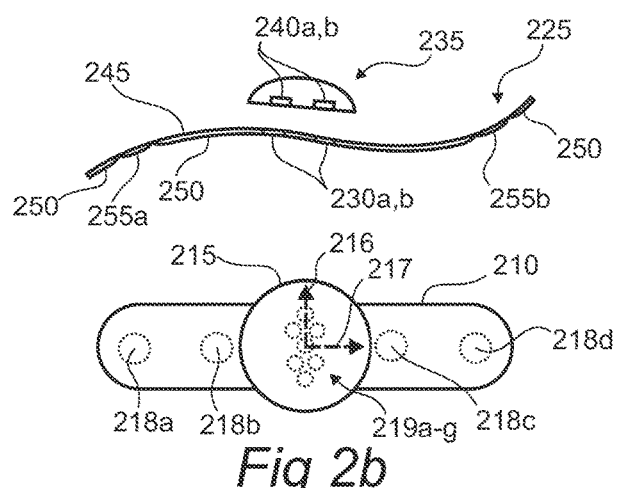

FIG. 2*b* shows aspects of a patch 225 and a corresponding module 235 each in accordance with the present disclosure. The patch includes a substrate 245, an adhesive layer 250, multiple patch interconnects 230*a, b*, and multiple electrodes 255*a, b*, each in accordance with the present disclosure. The patch interconnects 230*a,b* and the electrodes 255*a,b* are electrically coupled together via one or more conducting traces located on the substrate 245, embedded into the substrate 245, etc.

The module 235 includes multiple module interconnects 240*a,b* in accordance with the present disclosure configured, dimensioned, and arranged so as to mate with the corresponding patch interconnects 230*a,b*. The interconnects 230*a,b* 240*a,b* may include snap elements, magnetic elements, etc. as discussed throughout the present disclosure.

FIG. 2*b* also shows a module 215 coupled to a corresponding patch 210, the module and patch containing a series of mating interconnects 219*a-g*, the patch including one or more sensors and/or electrodes 218*a-d* (e.g. here shown as circular electrode elements spaced along the length of the patch 210). Also shown are two axes, a lengthwise axis 217 oriented along a direction of expected stretch for the patch 210 during use, and a substantially perpendicular axis 216 oriented along a directly substantially perpendicular to the direction of expected stretch for the patch 210. In aspects, the mating interconnects 219*a-g* may be oriented along the patch, such that they are aligned with the perpendicular axis 216 when the module 215 is mated with the patch 210 during use. Such a configuration may be advantageous for limiting stress and/or movement around one or more of the interconnects 219*a-g* during a typical usage case.

Figure 2C:
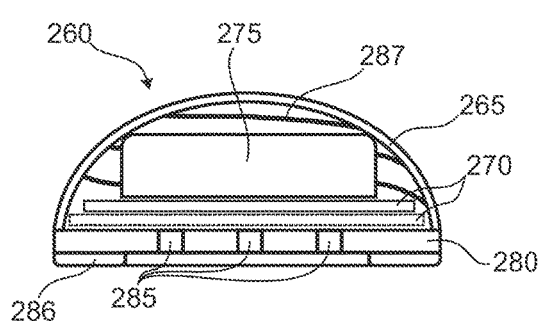

FIG. 2*c* shows aspects of a module 260 in accordance with the present disclosure. The module 260 includes a housing 265, a portion of which is provided by a printed circuit board 280 in accordance with the present disclosure. The housing 265 includes a dome shaped component upon which a three dimensional antenna 287 is formed, embedded, printed upon, etc. In aspects, the antenna 287 may be formed in the shape of a helical structure, a multipolar structure, a curved dipole structure, a monopolar structure etc. In aspects, the antenna 287 may include one or more interconnects which may be patterned so as to mate with corresponding connectors on the printed circuit board 280 during an assembly procedure. In aspects, the antenna 287 may be formed from a free standing electrically conducting structure and attached to the printed circuit board 280 during assembly.

In aspects, the antenna 287 may be formed as a curved dipolar antenna. The trace of the antenna 287 arranged so as to extend from contacts on the circuit board 280 onto the housing 265 and outward to form an airplane wing-like shape. Such a configuration may be advantageous for simplifying interface between the antenna and an amplifier, for shaping the RF waves emitted from the module 260 when adjacent to a subject, as well as for decoupling the RF circuitry from a ground plane of the circuit board 280, so as to minimize DC charge accumulation during RF transmissions from the module 260.

The module 260 in accordance with the present disclosure may include one or more components 270 (e.g. microcircuits, sensors, transducers, etc. optionally stacked/embedded into PCBs, etc.), interconnects 285, and a power source 275 each in accordance with the present disclosure.

The module 260 may be hermetically sealed, etc. so as to isolate components 270 therein from the surroundings. The module 260 may include gasket 285 in accordance with the present disclosure to minimize transfer of fluids into the region of contact between the module 260, the interconnects 285, and a corresponding patch in accordance with the present disclosure.

Figure 2D:
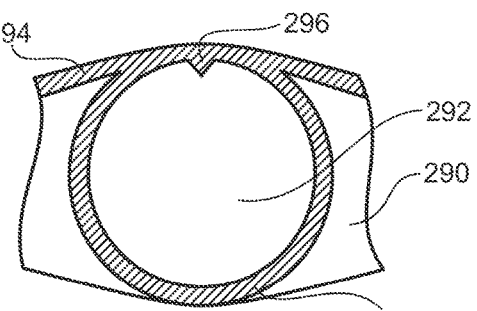

FIG. 2d shows aspects of orientation markings 294, 296, 298 on a module 292 and a patch 290 in accordance with the present disclosure. Such markings 294, 296, 298 may be advantageous to assist a user with alignment and attachment of a module 292 to a patch 290 as well as may be useful for a vision algorithm to extract orientation, functional (e.g. by color or pattern of the markings 294, 296, 298), and/or identification information from an image of the patch 290 and module 292 as placed onto a subject as part of a monitoring session.

FIGS. 3a-f show aspects of patches in accordance with the present disclosure.

Figure 3A:
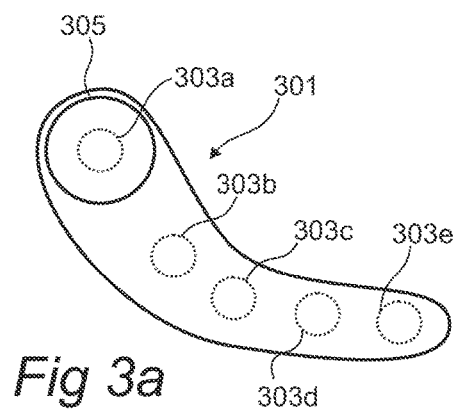
FIGS. 3a-f show aspects of patches in accordance with the present disclosure.

FIG. 3a shows a patch 301 coupled to a module 305 each in accordance with the present disclosure. The patch 301 includes a plurality of electrodes 303a-e for interfacing with a subject. The electrodes 303a-e are arranged in a somewhat linear fashion along the patch 301, perhaps for assessing electrocardiographic signals at sites in the vicinity of the heart of a subject.

Figure 3B:
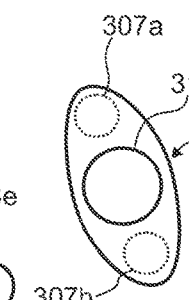

FIG. 3b shows a patch 306 coupled to a module 310 each in accordance with the present disclosure. The patch 306 includes a bipolar electrode arrangement 307a,b for interfacing with a subject. Such an arrangement may be advantageous for monitoring heart-rate, a signal channel EKG, EMG, respiration rate, acoustic monitoring coupled with EMG of one or more neck or facial muscles, EEG monitoring coupled with kinematic sensors behind the ear, etc. of a subject as part of a monitoring session.

Figure 3C:
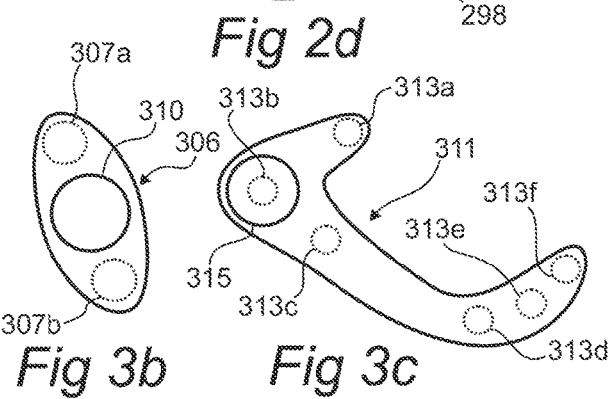

FIG. 3c shows a patch 311 coupled to a module 315 each in accordance with the present disclosure. The patch 311 includes multiple electrodes 313a-f for interfacing with a subject. The electrodes 313a-f may be arranged so as to interface with one or more muscle groups along an appendage of a subject, as part of an EMG study in accordance with the present disclosure. The patch 311 may be formed so as to maintain an electrical interface between the electrodes and the module 315 while undergoing stretch during the monitoring session (e.g. in aspects where the length between the electrodes may change substantially during the monitoring session, etc.). In aspects, such a configuration may be advantageous for spanning the length of a muscle, crossing a joint, wrapping around the curvature of a limb, a foot, etc. of a subject as part of a monitoring session.

Figure 3D:
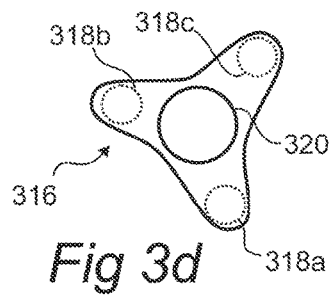

FIG. 3d shows a patch 316 coupled to a module 320 each in accordance with the present disclosure. The patch 316 includes three electrodes 318a-c for interfacing with a subject. The electrodes 318a-c may be arranged so as to provide multi-site capture of electrophysiological activity on the subject. Such an arrangement may be advantageous for generating a field vector in the vicinity of the patch 316. In aspects, the module 320 may include an algorithm configured to analyze incoming data from the electrodes 318a-c (i.e. perhaps with a signal electrode in the set selected as a reference etc.) and to calculate field vector with orientation and magnitude in relationship to the orientation of the electrodes on the patch 316. In aspects, such a configuration may be advantageous for calculating a vector electrocardiogram on a subject, calculating muscle action potential vectors, muscle signal orientation, calculating electric field propagation directions along the surface of the subject, or the like.

Figure 3E:
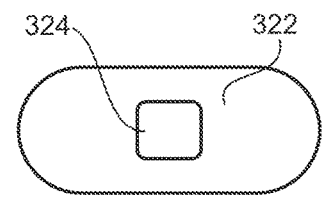

FIG. 3e shows a patch 322 in accordance with the present disclosure. The patch 322 includes a window 324 through which a sensor (e.g. an optical sensor, etc.) included in an associated module (not explicitly shown) may interface with the subject during a monitoring procedure. The patch 322 may include further electrodes, sensors, etc. (not explicitly shown) to enable additional monitoring functionality from the same module. Such a configuration may be advantageous for monitoring local blood flow optically, perform colorimetric assessment of underlying tissues, provide seamless entry of radiation into the tissues, etc. during a monitoring session in accordance with the present disclosure.

Figure 3F:
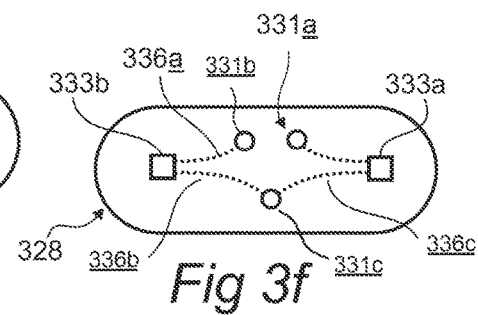
Figure 4A:
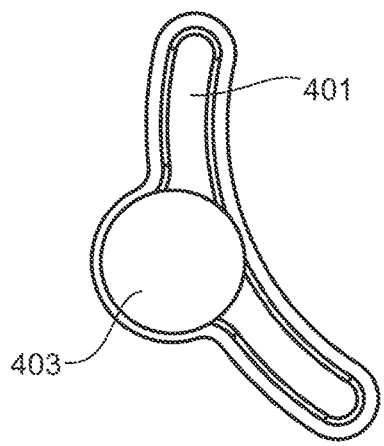
FIGS. 4a-f show top, side, and isometric views of a mated patch and module in accordance with the present disclosure.
Figure 4B:
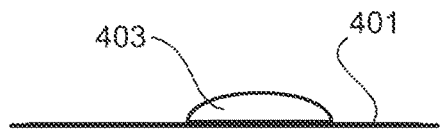
Figure 4C:
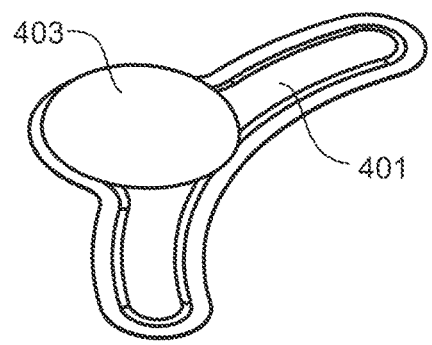
Figure 4D:
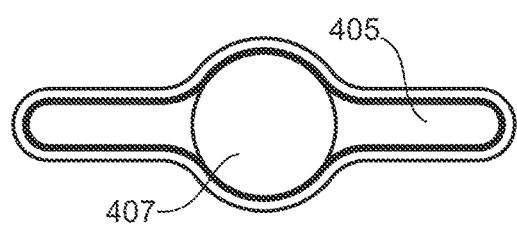
Figure 4E:
Figure 4F:
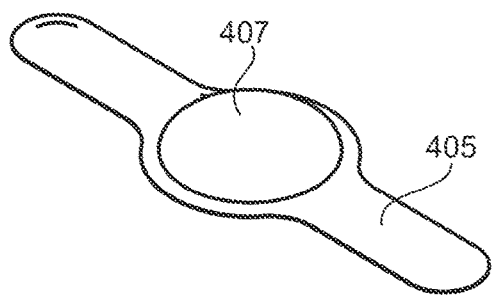

FIG. 3f shows a patch 328 in accordance with the present disclosure. The patch 328 includes multiple sensors 333a,b, coupled with a plurality of conducting members (e.g. electrical traces, printed conductors, spun nanotube fibers, stretchable conducting traces, etc.) 336a-c, and a plurality of interconnects 331a-c each in accordance with the present disclose. The sensors 333a,b may be arranged, configured, and dimensioned so as to interface with and/or monitor an underlying tissue structure, property, and/or tissue or fluid analyte (such as tissue composition, fat content, water content, blood oxygen saturation levels, etc.), of a subject during a monitoring procedure.

FIGS. 4a-f show top, side, and isometric views of a mated patch 401, 405 and module 403, 407 each in accordance with the present disclosure. Such a configuration may be advantageous for providing robust, comfortable monitoring of a subject in accordance with the present disclosure.

Figure 5:
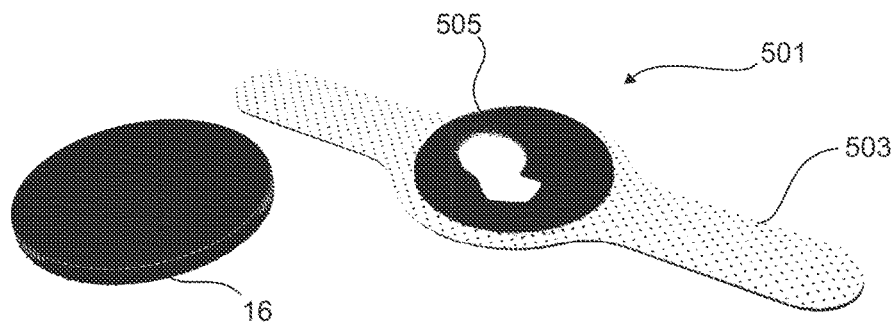
FIG. 5 shows a perspective view of aspects of a mated patch and module in accordance with the present disclosure.

FIG. 5 shows a perspective view of aspects of a mated patch 503 and module 505 forming a patch/module pair 501 each in accordance with the present disclosure. The patch/module pair 501 is shown beside a coin 16 (a US quarter) for perspective.

Figure 6:
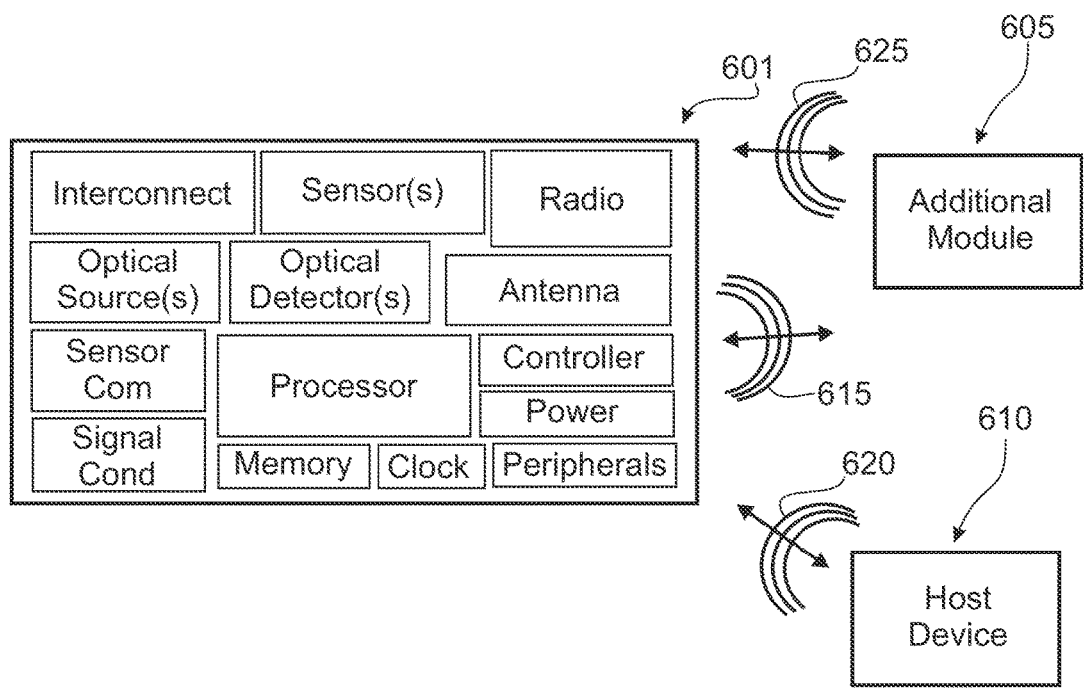
FIG. 6 shows a schematic of aspects of a module in accordance with the present disclosure.

FIG. 6 shows a schematic of aspects of a module 601 in accordance with the present disclosure. The module 601 includes one or more of interconnects, sensors, optical source(s), optical detector(s), a radio, an antenna, a sensor communication circuit, a signal conditioning circuit, a processor, a memory device, a controller, a power supply, power management circuit, and/or energy harvesting circuit, and one or more peripherals each in accordance with the present disclosure. The module 601 is shown in wireless communication 615, 625, 620 with an additional module 605 (e.g. perhaps situated in the same monitoring system, on the same subject, etc.), and a host device 610. Further aspects of the module 601 are discussed throughout this disclosure.

FIG. 7 shows a schematic of a patch/module pair 701 attached to a subject 3 in accordance with the present disclosure. The patch/module pair 701 includes a module 705 coupled to a corresponding patch 710, the patch includes multiple electrodes 720a-c arranged for interfacing with the skin of the subject 3. The patch/module pair 701 is shown in wireless communication 725 with a host device (not explicitly shown). Such a configuration may highlight how a stretchy patch 710 may be able to maintain monitoring of the subject in light of movements, changes in shape or stretching along the surface of the skin of the subject 3, etc. Such a configuration may be advantageous to provide a soft comfortable monitor, with a low cost disposable patch 710 and a miniature reusable module 705.

FIGS. 8a-e show aspects of non-limiting examples of patch electrode layouts in accordance with the present disclosure.

FIG. 8a shows a patch 801 coupled to a module 803 each in accordance with the present disclosure. The patch 801 includes a plurality of electrodes 805a-b for interfacing with a subject. The electrodes 805a-b are arranged in a very tight bipolar arrangement suitable for obtaining a bipolar electrical reading from the surface of a subject with a very small profile. In aspects, one or more of the electrodes 805a,b may include an electrode feature in accordance with the present disclosure for enhancing the electrical coupling between the module 803 and the underlying tissues of a subject. In aspects, pressure applied to the top of an attached module 803 may be suitable for engaging an electrode feature with the underlying tissue of the subject. Such an arrangement may be advantageous for providing an ultra-miniature heart-rate monitor, a pediatric heart-rate monitor, an EMG sensor for placement near a sexual organ, an electrophysiological monitor behind an ear, on a neck, etc.

FIG. 8b shows a patch 807 coupled to a module 809 each in accordance with the present disclosure. The patch 807 includes a bipolar electrode arrangement 811a,b for interfacing with a subject. Such an arrangement may be advantageous for monitoring heart-rate, a signal channel EKG, respiration rate, etc. of a subject as part of a monitoring session. A plurality of such patches 807 may be applied to a subject to simultaneously extract a higher level or spatially distributed electrical field over the body of the subject.

FIG. 8c shows a patch 813 coupled to a module 815 each in accordance with the present disclosure. The patch 813 includes three electrodes 817a-c for interfacing with a subject. The electrodes 817a-c may be arranged so as to allow for multi-site capture of electrophysiological activity on the subject. Such an arrangement may be advantageous for generating a field vector in the vicinity of the patch 813.

FIG. 8d shows a patch 819 coupled to a module 821 each in accordance with the present disclosure. The patch 819 includes a quadripolar electrode arrangement 823a-d for interfacing with a subject. The quadripolar electrodes 823a-d may be arranged so as to allow for multi-site capture of electrophysiological activity on the subject. Such an arrangement may be advantageous for generating a field vector in the vicinity of the patch 819, for mapping electric field propagation across the surface of the subject, etc.

FIG. 8e shows a patch 825 coupled to a module 827 each in accordance with the present disclosure. The patch 825 includes a plurality of electrodes 829a-b for interfacing with a subject. The electrodes 829a-b are shown in a bipolar arrangement connected to stretchable conducting elements 831a,b. In aspects, such a configuration may be advantageous to freely flex and stretch 833 along with the nearby tissues of the subject during a monitoring session. The stretchable conducting elements 831a,b may be arranged so as to repeat ably change impedance during stretch. Such a configuration may be advantageous for assessing movement under the patch (e.g. due to muscle movement, breathing, etc.) in conjunction with one or more physiologic signals (e.g. such as electrophysiological signals, stretch related artifact, etc.) in accordance with the present disclosure. Such a configuration may be suitable for physiotherapy monitoring sessions (e.g. combined proprioceptive monitoring in conjunction with EMG, assessing breathing in conjunction with EKG, gait assessment, a running gait correction system, etc.).

In aspects, such a configuration may be advantageous for a training and/or physiotherapy system. Dual implementation of movement (e.g. across joints, cross-wise to a joint, etc.) in conjunction with EMG related information (e.g. exertion, muscle fatigue, etc.) may be advantageous to detect risk of injury, map progression of therapy, etc.

FIG. 9 shows aspects of an impact sensing patch 900 and a feedback component 925 in accordance with the present disclosure. The impact sensing patch 900, here shown integrated into a knee brace on a subject 4, may include one or more piezoresistive materials (i.e. materials that change electrical properties or charge storage thereupon in relation to strains placed thereupon), a capacitive stretch sensor in accordance with the present disclosure, a pressure sensitive nano-composite structure, or the like. Upon impact 905 of the patch 900 with an object 5, a coupled module 910 may send one or more signals 915 to a feedback device 925, a host device, etc. in accordance with the present disclosure. In aspects, the feedback device 925 may accept the signal 935 and produce a feedback signal (e.g. an audio signal, a vibration signal, a tactile signal, a visual signal, etc.) for delivery to a user in accordance with the present disclosure. In this non-limiting example, the feedback device 925 produces an audible feedback signal in the ear 6 of the subject via a loudspeaker 930. Such a system may be advantageous for monitoring impacts on a subject with neuropathy (e.g. lack of sensation in an extremity, for assistance with gait analysis, for providing feedback during exercise, etc.) so as to provide the subject with a transferred sensation of touch in a region of their body that still has sensation (e.g. via a tactile feedback component, audible cue, visual cue, etc.), or for formation of a feedback loop to a touch related event.

FIGS. 10a-c show aspects of a patch in accordance with the present disclosure.

FIG. 10a shows a patch including a substrate 1005 (or adhesive layer) formed from a conducting, self-adhering material (i.e. so as to provide combined electrical and mechanical coupling to an adjacent body), a conducting trace 1010 configured to electrically couple a region of the substrate 1005 to a corresponding interconnect (not explicitly shown), and including a dielectric layer 1015 configured to isolate one or more regions of the substrate 1005 from one or more regions of the conducting trace 1010. In aspects, the substrate 1005 may initiate charge transfer 1025 with an adjacent surface during use (e.g. so as to electrically couple thereto, to form a suitable sensory interface thereto, to provide electroporation thereto, to provide current flow thereto, to monitor aspects thereof, etc.). The substrate 1005 is shown with a predetermined thickness 1020 in accordance with the present disclosure. In aspects, to maintain a breathable, flexible interface, the thickness 1020 may be less than 200 um, less than 100 um, less than 50 um, less than 25 um, less than 12 um, less than 6 um, etc. In aspects, the thickness 1020 may be sufficiently thick so as to retain a tear strength sufficient to allow for removal of the patch from the subject without tearing. The tear strength may be greater than 0.5 N/mm, greater than 1 N/mm, greater than 2 N/mm, etc. (i.e. as measured in accordance with ASTM standard ASTM-D-624 DIE tear strength).

FIG. 10b shows aspects of a patch in accordance with the present disclosure including an adhesive layer 1035 coupled with a substrate 1030 each in accordance with the present disclosure. The patch includes a microstud 1040 interconnect coupled through the thickness of the substrate 1030. In the non-limiting example shown the microstud 1040 also includes an electrode 1050 and corresponding electrode features 1055 for interfacing with the body of a subject. The microstud 1040 may also provide a top side interconnect for interfacing with a module, etc.

In aspects, the electrode 1050 may be suitable for providing charge transfer 1055 with an adjacent surface during use (e.g. so as to electrically couple thereto, to provide electroporation thereto, to provide current flow thereto, to monitor aspects thereof, etc.). The patch is shown with a predetermined thickness 1045 in accordance with the present disclosure. In aspects, to maintain a breathable, flexible interface, the thickness 1045 may be less than 200 um, less than 100 um, less than 50 um, less than 25 um, less than 12 um, less than 6 um, etc.

FIG. 10c shows aspects of a patch in accordance with the present disclosure including an adhesive layer 1060 coupled with a substrate 1065 each in accordance with the present disclosure. The patch includes a rivet style stud 1070 coupled through the thickness of the substrate 1065. In the non-limiting example shown the rivet style stud 1070 also includes an electrode and a cap 1075 to hold it tightly to the substrate 1065 in use. The patch includes a conducting layer 1080 (in this case shown coating the stud 1070 but may alternatively be applied between the cap 1075 and the substrate 1065) for communicating with an interconnect (not explicitly shown). The patient side of the stud 1070 is shown coated with a thin electroconducting gel 1085 in accordance with the present disclosure. In aspects, the rivet style stud 1070 may include a button top, a snap interconnect, etc. for directly interfacing with a corresponding module or the like.

In aspects, the gel 1085 may be suitable for providing charge transfer 1095 with an adjacent surface during use (e.g. so as to electrically couple thereto, to provide electroporation thereto, to provide current flow thereto, to monitor aspects thereof, etc.). The patch is shown with a predetermined thickness 1090 in accordance with the present disclosure. In aspects, to maintain a breathable, flexible interface, the thickness 1090 may be less than 200 um, less than 100 um, less than 50 um, less than 25 um, less than 12 um, less than 6 um, etc.

FIGS. 11a-b show aspects of patches and modules in accordance with the present disclosure.

FIG. 11a shows aspects of a patch 1105 and a module 1115 in accordance with the present disclosure. The patch 1105 includes an adhesive layer 1107, a substrate 1109, and electrodes 1110a,b. In the non-limiting example shown, the electrodes are configured to directly interface with a corresponding module 1115. The module 1115 is shown with a plurality of corresponding interconnects 1120a,b each including caps to isolate one or more regions of the module 1115 from the elements. The module 1115 may be configured for wireless communication 1130 in accordance with the present disclosure.

FIG. 11b shows aspects of a patch 1140 and a corresponding module 1160 each in accordance with the present disclosure. The patch 1140 may include a substrate 1145 coupled to a patient facing adhesive layer 1155, and a module interfacing adhesive 1150 (i.e. patterned over a region thereof so as to interface with a module 1160 placed thereupon). The module 1160 includes an optical source 1165 for emitting energy towards 1172 a subject, and an optical sensor 1170 for receiving energy from 1175 a subject. The module 1160 may be configured and dimensioned for placement onto the corresponding patch 1140. One or more layers of the patch 1140 may be transparent to the radiation, so as to facilitate interaction of the module 1160 with an adjacent subject. The module 1160 may be configured for wireless communication 1180 in accordance with the present disclosure.

FIGS. 12a-c show aspects of patches and modules in accordance with the present disclosure.

FIG. 12a shows aspects of a patch 1201 in accordance with the present disclosure including a substrate 1203 and an adhesive layer 1205 coupled thereto (in this case, optionally an ionically conducting adhesive). The patch 1201 includes an optional sensor 1207 embedded into the substrate 1203 and a patch interconnect 1211a,b for coupling to a module 1215 and provided in electrical communication with the sensor 1207 (e.g. via electrical interconnects coupled to the substrate 1203, optionally printed along the face of the substrate 1203 facing the adhesive layer 1205). The sensor 1207 is configured for delivery of energy 1209a into and sensing of energy 1209b received from a subject during use (e.g. such as an optical sensor, a spectrometer, etc.). FIG. 12a shows a module 1215 in accordance with the present disclosure configured and dimensioned to mate with the patch 1201. The module 1215 includes a module interconnect 1217a,b arranged to mesh with the corresponding patch interconnect 1211a,b. In the non-limiting example shown, the patch interconnect 1211a,b may include a ferromagnetic material and the module interconnect 1217a,b may include magnetic materials configured such than a substantially strong magnetic field 1219a,b is formed there between when placed in close proximity to each other (i.e. during assembly). The interconnects 1211a,b, 1217a,b may be configured to form an electrically conducting interface between the patch 1201 and the module 1215 upon assembly, alternatively an inductive interface, or a capacitive interface in accordance with the present disclosure.

Also shown, the patch 1201 includes a plurality of electrodes 1208a,b each in accordance with the present disclosure. The electrodes 1208a,b are coupled to the patch interconnect 1211a,b with one or more stretchy electrically conducting traces each in accordance with the present disclosure (e.g. in this case provided by a stretchable electrically conducting ink, printed onto a surface 1212 of the substrate 1203 so as to be sandwiched between the substrate 1203 and the adhesive 1205). The electrodes 1208a,b may include one or more electrically conducting and/or ionically conducting substances each in accordance with the present disclosure for interfacing with an adjacent subject during use.

FIG. 12b shows aspects of a patch 1227 coupled to a module 1225 in accordance with the present disclosure. The patch 1227 includes a substrate 1230 and adhesive 1235 for interfacing with a subject, each of which are substantially transparent to energy transferred to and/or from 1245 the module 1225 into the subject during use. Such energy transfer 1245 may be completed by a transducer 1240 and may be monitored by the same or an equivalent sensitive transducer 1240.

FIG. 12c shows aspects of a patch 1251 and a corresponding module 1265 each in accordance with the present disclosure. The patch 1251 includes a substrate 1253 and electrodes 1255*a-c* for interfacing with a subject. The patch 1251 includes multiple microstuds 1271*a-c* in accordance with the present disclosure. The studs 1271*a-c* may be electrically coupled with the electrodes 1255*a-c* via traces included in the substrate 1253 (e.g. patterned on, coated on, printed onto, embedded into the substrate 1253, etc.). The studs 1271*a-c* may coated with an insulating layer 1260, in this case configured so as to both insulate the studs 1271*a-c* from the subject but also to add local rigidity to the region of the patch 1251 in the vicinity of the interconnect (i.e. the collection of microstuds 1271*a-c*).

The module 1265 may include a plurality of corresponding connectors 1275*a-c* for interfacing with the microstuds 1271*a-c*. The connectors 1275*a-c* may be integrated into a printed circuit board 1270, which duals as a portion of the housing of the module 1265. In aspects, the connectors 1275*a-c* may include solderable components for securement to the PCB 1270. In aspects, the connectors 1275*a-c* may be substantially formed from through hole interconnects in the PCB 1270 (i.e. so as to simplify the assembly process thereof). In aspects, the PCB 1270 may include an undercoating, gasket, etc. in order to substantially isolate the interconnects 1271*a-c*, 1275*a-c* from the surroundings during use.

Figure 13:
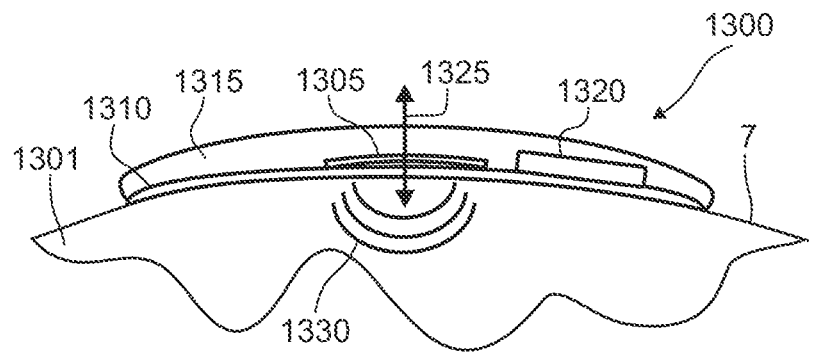
FIG. 13 shows a module configured to apply energy to a subject in accordance with the present disclosure.

FIG. 13 shows a schematic of a patch/module pair 1300 configured to apply energy 1325 (in this case vibrational energy) to the surface 7 a subject 1301 in accordance with the present disclosure. The patch/module pair 1300 includes an adhesive layer 1310 (i.e. potentially formed from a patch coupled to the module) for securement to the subject 7. The module 1315 includes a transducer 1305 configured to for generate vibrational energy 1325 for transfer 1330 into the subject 1301. The transducer 1305 may be controlled and/or powered by an electronics unit 1320 included in the module 1315. In the non-limiting example shown, the transducer 1305 may be piezoelectric material (e.g. polymer, ceramic, etc.).

Figure 14:
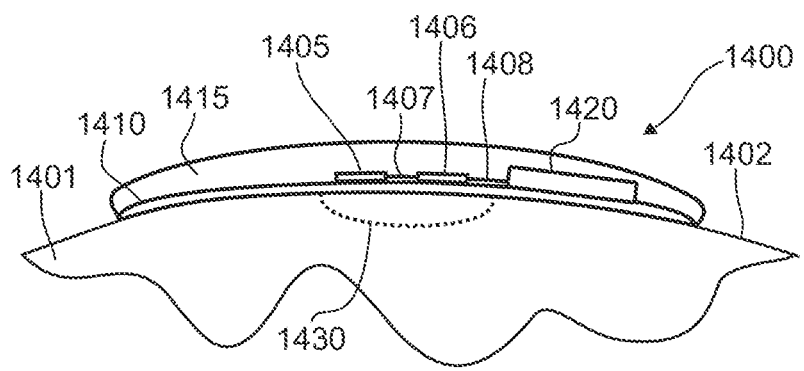
FIG. 14 shows a module for interrogating a subject in accordance with the present disclosure.

FIG. 14 shows a patch/module pair 1400 for applying thermal energy 1430 to a subject 1402 in accordance with the present disclosure. The patch/module pair 1400 includes an adhesive layer 1410 for attachment to a skin surface 1402 of the subject 1401. The module 1415 includes one or more heater bands 1405 or RF heating circuits, and thermocouples 1406 coupled to an electronics unit 1420 including a power source, a microcircuit, etc. via one or more electronic interconnects 1408.

Figure 15:
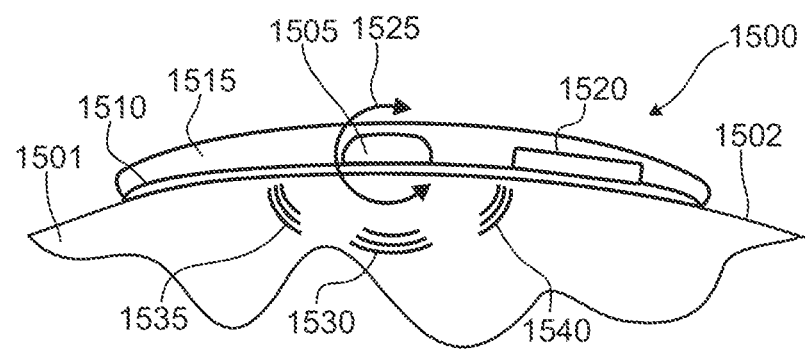
FIG. 15 shows a vibrating module configured to apply a tactile input to a subject in accordance with the present disclosure.

FIG. 15 shows a vibrating patch/module pair 1500 configured to apply a tactile input 1525 to the surface 1502 of a subject 1501 in accordance with the present disclosure. The patch/module pair 1500 includes an adhesive layer 1510 (i.e. potentially formed from a patch coupled to the module) for securement to the subject 1501. The module 1515 includes a transducer 1505 configured to for generate the torsional energy 1525 for transfer 1530, 1535, 1540 into the subject 1501. The transducer 1505 may be controlled and/or powered by an electronics unit 1520 included in the module 1515. In the non-limiting example shown, the transducer 1505 may be an electric motor with an eccentricity on the output shaft thereof. The transfer 1530, 1535, 1540 of energy into the surface 1502 of the subject 1501 may induce a range of sensations, from poking, to rubbing, dependent upon the amplitude, frequency, duration, duty cycle of the transducer 1505 as well as the physical configuration of the patch/module pair 1500 and the choice of adhesive layer 1510, if such a layer is used in the embodiment in question.

FIGS. 16*a-c* show arrangements of patches on a subject 2 for generating an EKG in accordance with the present disclosure. FIG. 16*a* shows an arrangement of three patches 1610*a-c* in accordance with the present disclosure arranged on the torso of a subject 2 so as to cover equilateral vectors passing out from the heart of the subject 2.

FIG. 16*b* shows an arrangement of four patches 1620*a-d* in accordance with the present disclosure arranged on the torso of a subject so as to cover vectors with trajectories leading away from the heart (patches 1620*a,c,d*) and to capture one or more signals near to the heart 1620*c* of the subject 2.

FIG. 16*c* shows an arrangement of three patches 1630*a-c* in accordance with the present disclosure arrange on the torso of the subject forming roughly a linear arrangement spanning from the sternum of the subject 2 across the left torso thereof.

The patches 1610*a-c*, 1620*a-d*, 1630*a-c* may include bipolar, tripolar, quadripolar, and/or multipolar electrode arrangements in accordance with the present disclosure. In aspects, the patches 1610*a-c*, 1620*a-d*, 1630*a-c* may include optical sensors positioned so as to determine local blood flow dynamics below each patch 1610*a-c*, 1620*a-d*, 1630*a-c* and may include one or more physical sensor (e.g. accelerometer, gyroscope, etc.) for purposes of addressing movement artifacts in the captured signals, etc.

FIGS. 17*a-c* show aspects of electrode features and methods for engaging such features with skin in accordance with the present disclosure.

FIG. 17*a* shows aspects of a patch 1701 in accordance with the present disclosure including a conductor 1710 and an electrode with one or more electrode features 1715 in accordance with the present disclosure thereupon. The electrode features 1715 may be forced into engagement with an adjacent tissue surface via a bias force 1716 (i.e. as may be applied by a thumb over top thereof).

FIG. 17*b* shows a 3 part sequence for engaging a series of electrode features 1721 with a skin surface 13 in accordance with the present disclosure. Initially (in frame 1), the electrode features 1721 are included on a conducting surface, in this case a bistable structure 1719 (i.e. a snap dome in this example). The bistable structure 1719 and the electrode features 1721 are electrically and mechanically connected into a substrate 1717 in accordance with the present disclosure, thus forming part of a patch in accordance with the present disclosure.

After placement onto the skin 13 of a subject, referring to frame 2, a bias force 1723 may be applied to the bistable structure 1719 causing the electrode features 1721 to engage with the skin 13 (e.g. to embed into the skin 13, penetrating 1725 one or more of the electrode features 1721 into the stratum corneum thereof).

Referring to frame 3, upon release of the bias force 1723, depending on the nature of the bistable structure 1719 the electrode features 1721 may disengage from the skin 13 leaving behind a series of micropunctures 1727, thus lowering the impedance of the electrical connection between the patch and the subject (i.e. via the skin 13). In aspects, the bistable structure 1719 may be configured to remain in the deformed position (i.e. plastically deform so as to engage one or more of the electrode features 1721 with the skin 13 long term during the monitoring process).

In aspects, the patch may include a hydrogel (not explicitly shown) located in and around the electrode features 1721 to maintain conductivity after retraction of the electrode features 1721 from the skin 13. The hydrogel may be intrinsically and/or ionically conducting, and may be patterned underneath the electrode, printed onto the electrode features 1721, etc.

FIG. 17c shows a 3 part sequence for engaging a series of electrode features 1747 with a skin surface 14 in accordance with the present disclosure. Initially (in frame 1), the electrode features 1747 are included on a conducting surface, in this case a conducting trace 1745 coupled with a substrate 1741 in accordance with the present disclosure, thus forming part of a patch 1740 in accordance with the present disclosure. The patch further includes a gel adhesive 1743 (such as an intrinsically or ionically conducting gel adhesive, hydrogel adhesive, etc. in accordance with the present disclosure). In aspects, the gel adhesive 1743 may be patterned, formed, or foamed so as to provide compressible aspects (i.e. so as to allow for volumetric changes during compression thereof). In aspects, the gel adhesive 1743 may be patterned onto the substrate 1741 and conducting trace 1745 so as to embed the electrode features 1747 within the gel adhesive 1743 (i.e. so as to just cover the electrode features 1747 such that upon placement of a skin surface 14, the electrode features 1747 do not engage with the skin surface 14).

After placement onto the skin 14 of a subject, referring to frame 2, a bias force 1749 may be applied to patch 1740 in the general vicinity of the electrode features 1747 causing the electrode features 1747 to engage with the skin 14 (e.g. to embed into the skin 14, penetrating 1753 into the stratum corneum thereof). During application of the bias force 1749, the gel adhesive 1743 may deform 1751 allowing for the electrode features 1747 to penetrate into the skin 14.

Referring to frame 3, upon release of the bias force 1749, the gel adhesive 1743 may (may be slowly) return 1757 to a somewhat undeformed state and thus the electrode features 1747 embedded therein may disengage from the skin 14 leaving behind a series of micropunctures 1759, thus lowering the impedance of the electrical connection between the patch and the subject (i.e. via the skin 14). In aspects, the gel adhesive 1743 may be configured to maintain a relatively humid and biofriendly environment in the vicinity of the micropunctures 1759, thus maintaining the micropunctures for a prolonged monitoring period without irritating the skin 14.

Figure 18:
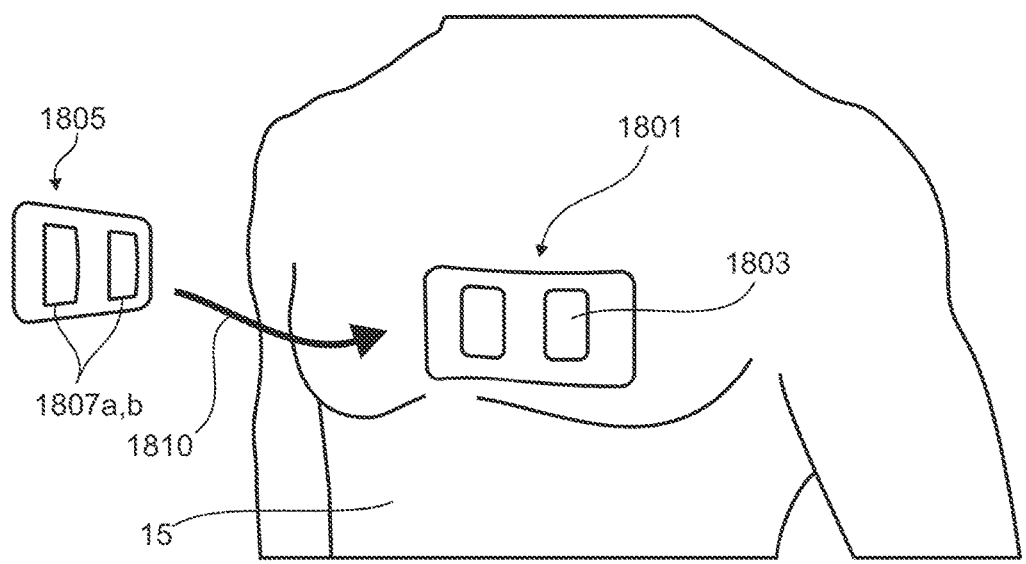
FIG. 18 illustrates an isolation patch in accordance with the present disclosure.

FIG. 18 illustrates an isolation patch 1801 in accordance with the present disclosure. The isolation patch 1801 may be configured to allow a user to electrically interface a handheld monitoring device 1805 (e.g. a handheld EKG monitor, an Alivecor™ device, etc.) with a plurality of electrodes 1807a,b with a subject 15 without bringing the device 1805 into physical contact therewith. In aspects, the isolation patch 1801 may include a substrate in accordance with the present disclosure and include one or more patterned regions 1803 thereupon through which a conduction adhesive layer patterned on the substrate of patch 1801 may be accessed from the surface of the substrate 1801 facing away from the subject 15 upon placement. To monitor the patient, the user may position the handheld monitoring device 1805 against the isolation patch 1801 such that electrodes 1807a,b touch the patch 1801 on the regions 1803.

In aspects, the adhesive layer may be formed from a conducting hydrogel adhesive, from a z-axis adhesive, etc. in accordance with the present disclosure.

Figure 19:
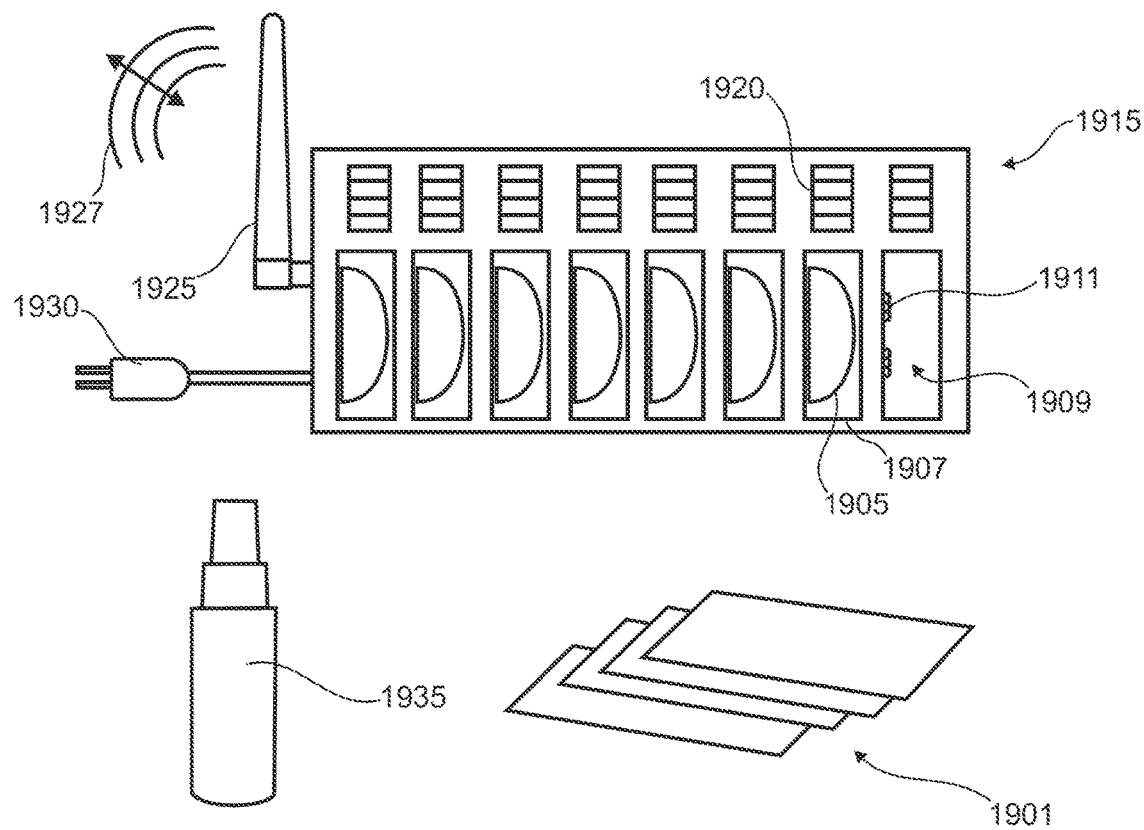
FIG. 19 shows aspects of a modular physiologic monitoring kit in accordance with the present disclosure.

FIG. 19 shows aspects of a modular physiologic monitoring kit in accordance with the present disclosure. The kit includes one or more modules 1905, patches 1901 (or equivalently sets of patches provided for implementation in specific monitoring functions), a recharging bay 1915 and optionally one or more accessories (e.g. such as a substantially pain free patch remover 1935, skin prep pads, etc.) each in accordance with the present disclosure. In aspects, the recharging bay 1915 may also provide functionality of a host device 1915. As a host device 1915, the recharging bay 1915 may include an antenna 1925 for communicating 1927 with one or more modules 1905 during a monitoring session.

To interface with the modules 1905, the recharging bay 1915 may include one or more docking receptacles 1907 each including a connector 1911 for interfacing with a module 1905 docked therein.

In aspects, the recharging bay 1915 may include one or more diagnostic indicators 1920 and a power supply 1930 in accordance with the present disclosure. In aspects, the recharging bay 1915 may be integrated into a monitoring display (e.g. a bedside monitor for placement within an ICU, OR, hospital, hospice, or homecare setting), etc.

In aspects, the recharging bay 1915 may include an alarm clock, for placement beside the bed of a subject (e.g. for easy swap out of modules 1905 during a prolonged monitoring session, for ease of use during sleep studies, etc.).

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A patch interface, comprising:
    a substrate comprising a flexible and stretchable material, the substrate having a first surface and a second surface opposite the first surface;
    an adhesive comprising a first surface and a second surface, the first surface of the adhesive being coupled to the second surface of the substrate, the second surface of the adhesive being formulated for attachment to the skin of a subject;
    one or more patch interconnects embedded into the substrate for attachment of the patch interface to a module comprising one or more microcircuits;
    at least one of: one or more sensors embedded in the substrate; and one or more electrodes attached to the second surface of the substrate, the one or more sensors and one or more electrodes being arranged, configured, and dimensioned to interface with the subject when the second surface of the adhesive is attached thereto; and
    one or more stretchable electrically conducting traces comprising an electrically conducting ink printed onto the second surface of the substrate between the substrate and the first surface of the adhesive, the one or more stretchable electrically conducting traces being arranged to couple one or more of the sensors and electrodes with one or more of the patch interconnects;
    wherein the patch interface is configured to monitor one or more physiologic signals, physical signals, and electrophysiological signals from the subject; and
    wherein the one or more patch interconnects provide an electrically conducting interface between the patch interface and the one or more microcircuits of the module.

2. The patch interface in accordance with claim 1, wherein the adhesive is patterned onto the second surface of the substrate so as to form one or more exposed regions of the second surface of the substrate, at least one of the one or more of the sensors and one or more electrodes arranged within the exposed regions; and wherein at least one of the one or more electrodes comprises one of an inherently conducting and an ionically conducting gel adhesive.

3. The patch interface in accordance with claim 2, wherein the gel adhesive is configured to maintain an improved electrical connection to the skin for one of more than one hour, more than one day, and more than three days after one of: the electrode contacts the skin; and pressure is applied to the electrode.

4. The patch interface in accordance with claim 1, wherein at least one of the one or more electrodes comprises an electrode feature comprising one or more microfibers, barbs, microneedles, and spikes to penetrate into a stratum corneum of the skin.

5. The patch interface in accordance with claim 4, wherein the electrode feature is configured to penetrate into the skin during engagement therewith one of less than 2 mm, less than 1 mm, less than 0.5 mm, and less than 0.2 mm.

6. The patch interface in accordance with claim 1, wherein the one or more patch interconnects comprise a plurality of connectors, the connectors physically connected to each other through the substrate; and wherein the patch interface comprises an isolating region arranged so as to isolate one or more of the connectors from the skin while the patch interface is engaged therewith.

7. The patch interface in accordance with claim 1, wherein the patch interface is sufficiently physically frail such that it cannot retain a predetermined shape in a free standing state.

8. The patch interface in accordance with claim 7, further comprising a temporary stiffening member attached to the substrate, the temporary stiffening member configured to provide retention of the shape of the patch interface prior to attachment to the subject, the stiffening member being removable from the substrate after attachment to the subject.

9. The patch interface in accordance with claim 7, wherein removal of the patch interface from the skin of the subject results in a permanent loss in shape of the patch interface without tearing of the patch interface.

10. The patch interface in accordance with claim 1, wherein the adhesive has a peel tack to mammalian skin of one of greater than 0.02 N/mm, greater than 0.1 N/mm, greater than 0.25 N/mm, greater than 0.50 N/mm, and greater than 0.75 N/mm.

11. The patch interface in accordance with claim 1, wherein the substrate is formed from a soft pseudo-elastic material and the patch interface is configured to maintain operation when stretched to one of more than 25%, more than 50%, and more than 80%.

12. The patch interface in accordance with a claim 1, wherein the patch interface is configured with a moisture vapor transmission rate of one of between 200 g/m2/24 hrs and 20,000 g/m2/24 hrs, between 500 g/m2/24 hrs and 12,000 g/m2/24 hrs, and between 1,000 g/m2/24 hrs and 8,000 g/m2/24 hrs.

13. The patch interface in accordance with claim 1, wherein the patch interface comprises a direction of expected stretch, and wherein the one or more patch interconnects are oriented on the substrate of the patch interface along an axis substantially perpendicular to the direction of expected stretch.

14. The patch interface in accordance with claim 1, wherein the one or more patch interconnects comprise one or more ferromagnetic regions formed from a stretchable pseudo elastic material, the one or more ferromagnetic regions being printed onto the first surface of the substrate.

15. The patch interface in accordance with claim 1, wherein at least one of the one or more stretchable electrically conducting traces is configured to change impedance based at least in part on stretch of the patch interface.

16. A module, comprising:
a housing;
a circuit board comprising one or more microcircuits; and
one or more module interconnects coupled to one or more of the microcircuits configured for placement and coupling of a device onto a patch interface, the patch interface comprising:
a substrate comprising a flexible and stretchable material, the substrate having a first surface and a second surface opposite the first surface;
an adhesive comprising a first surface and a second surface, the first surface of the adhesive being coupled to the second surface of the substrate, the second surface of the adhesive being formulated for attachment to the skin of a subject;
one or more patch interconnects embedded into the substrate for attachment of the patch interface to the module;
at least one of: one or more sensors embedded in the substrate; and one or more electrodes attached to the second surface of the substrate, the one or more sensors and one or more electrodes being arranged, configured, and dimensioned to interface with the subject when the second surface of the adhesive is attached thereto; and
one or more stretchable electrically conducting traces comprising an electrically conducting ink printed onto the second surface of the substrate between the substrate and the first surface of the adhesive, the one or more stretchable electrically conducting traces being arranged to couple one or more of the sensors and electrodes with one or more of the patch interconnects;
wherein the module is configured to monitor one or more physiologic signals, physical signals, and electrophysiological signals from the subject; and
wherein the one or more patch interconnects provide an electrically conducting interface between the patch interface and the one or more microcircuits of the module.

17. The module in accordance with claim 16, wherein the one or more module interconnects are embedded into the circuit board and the circuit board constitutes at least a portion of the housing.

18. The module in accordance with claim 16, further comprising a three dimensional antenna coupled to at least one of the one or more microcircuits, the one or more microcircuits comprising a transceiver or transmitter coupled to the antenna.

19. The module in accordance with claim 16, further comprising a sensor coupled with at least one of the one or more microcircuits, the sensor configured to interface with the subject upon attachment of the module to the patch interface.

20. The module in accordance with claim 19, wherein the module comprises at least one of: one or more sensors; and one or more microelectronics, configured to interface with a sensor included on the patch interface, at least one of the one or more sensors comprising: an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, and a microphone.

21. The module in accordance with claim 16, wherein the module is hermetically sealed.

22. The module in accordance with claim 16, further comprising a gasket coupled to the circuit board, the gasket formed so as to isolate the region formed by the one or more module interconnects and the patch interconnects from a surrounding environment when the module is coupled with the patch interface.

23. A device, comprising:
a patch interface; and
a module comprising:
   a housing;
   a circuit board comprising one or more microcircuits; and
   one or more module interconnects coupled to one or more of the microcircuits configured for placement and coupling of the module onto the patch interface;
wherein the one or more module interconnects are sized and dimensioned to interface with one or more patch interconnects within the patch interface, and the patch interface is coupled to a subject to form an operable interconnection between the patch interface and the module;
wherein the device is configured to monitor one or more physiologic signals, physical signals, and electrophysiological signals from the subject;
wherein the patch interface comprises one or more stretchable electrically conducting traces arranged to couple at least one of one or more sensors and one or more electrodes of the patch interface with one or more of the patch interconnects;
wherein the one or more stretchable electrically conducting traces comprise an electrically conducting ink printed onto a surface of the substrate between an adhesive and the surface of the substrate;
wherein the one or more patch interconnects provide an electrically conducting interface between the patch interface and the one or more microcircuits of the module.

24. The device in accordance with claim 23:
wherein the one or more patch interconnects comprise one or more ferromagnetic regions formed from a stretchable pseudo elastic material, the one or more ferromagnetic regions being printed on a flexible and stretchable substrate of the patch interface; and
wherein the one or more module interconnects comprise one or more electrically conducting magnetic elements, the one or more magnetic elements arranged so as to physically and electrically couple the module to the patch interface when the one or more magnetic elements are aligned with the one or more ferromagnetic regions.

25. The device in accordance with claim 23, wherein at least one of the module and the patch interface comprises one or more fiducial markings to visually assist with alignment of the module to the patch interface during coupling thereof.

* * * * *